United States Patent
Kalluri et al.

(10) Patent No.: US 10,959,952 B2
(45) Date of Patent: Mar. 30, 2021

(54) USE OF EXOSOMES FOR THE TREATMENT OF DISEASE

(71) Applicant: Board of Regents, The University of Texas System, Austin, TX (US)

(72) Inventors: Raghu Kalluri, Houston, TX (US); Sónia Melo, Maia (PT)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/203,265

(22) Filed: Nov. 28, 2018

(65) Prior Publication Data

US 2019/0117570 A1  Apr. 25, 2019

Related U.S. Application Data

(63) Continuation of application No. 15/735,186, filed as application No. PCT/US2016/037018 on Jun. 10, 2016, now abandoned.
(Continued)

(51) Int. Cl.
*A61K 48/00* (2006.01)
*C12N 15/11* (2006.01)
(Continued)

(52) U.S. Cl.
CPC ........ *A61K 9/1271* (2013.01); *A23C 19/0904* (2013.01); *A23L 9/10* (2016.08); *A23L 23/10* (2016.08); *A23L 25/10* (2016.08); *A23L 27/60* (2016.08); *A23L 29/20* (2016.08); *A23L 29/212* (2016.08); *A23L 29/231* (2016.08); *A23L 29/238* (2016.08); *A23L 29/25* (2016.08); *A23L 29/256* (2016.08); *A23L 29/262* (2016.08); *A23L 29/269* (2016.08); *A23L 33/185* (2016.08); *A23L 33/40* (2016.08); *A61K 9/0019* (2013.01); *A61K 45/06* (2013.01); *A61P 35/00* (2018.01);
(Continued)

(58) Field of Classification Search
CPC .... A61K 9/1271; A61K 9/0019; A61K 9/127; A61K 9/5068; C12N 15/113; C12N 15/1135; C12N 2310/14
See application file for complete search history.

(56) References Cited

U.S. PATENT DOCUMENTS 6,391,582 B2    5/2002  Luo et al.
6,812,023 B1   11/2004  Lamparski et al.
(Continued)

FOREIGN PATENT DOCUMENTS

CN    1265038 A    8/2000
CN    1325441 A    12/2001
(Continued)

OTHER PUBLICATIONS

Blanc et al. (Blood, 2009 vol. 114, No. 18:3928-3934).*
(Continued)

*Primary Examiner* — Terra C Gibbs
(74) *Attorney, Agent, or Firm* — Parker Highlander PLLC

(57) ABSTRACT

The present invention provides lipid-based nanoparticles (e.g., liposomes or exosomes) having CD47 on their surface and comprising a therapeutic agent (e.g., a therapeutic protein, an antibody, an inhibitory RNA, and/or a small molecule drug). Furthermore, the present invention provides for use of such lipid-based nanoparticles in therapy.

10 Claims, 25 Drawing Sheets

Specification includes a Sequence Listing.

Related U.S. Application Data

(60) Provisional application No. 62/173,838, filed on Jun. 10, 2015.

(51) Int. Cl.

| | | |
|---|---|---|
| *C07H 21/02* | (2006.01) |
| *C07H 21/04* | (2006.01) |
| *A61K 9/127* | (2006.01) |
| *A23L 29/20* | (2016.01) |
| *A23L 29/238* | (2016.01) |
| *A23L 29/25* | (2016.01) |
| *A23L 33/185* | (2016.01) |
| *A23L 29/231* | (2016.01) |
| *A23L 29/256* | (2016.01) |
| *A23L 29/262* | (2016.01) |
| *A23L 29/212* | (2016.01) |
| *A23L 29/269* | (2016.01) |
| *A23L 33/00* | (2016.01) |
| *A23L 23/10* | (2016.01) |
| *A23L 25/10* | (2016.01) |
| *A23L 27/60* | (2016.01) |
| *A23L 9/10* | (2016.01) |
| *A23C 19/09* | (2006.01) |
| *A61P 35/00* | (2006.01) |
| *A61K 9/00* | (2006.01) |
| *A61K 45/06* | (2006.01) |
| *C12N 15/113* | (2010.01) |
| *C12N 15/88* | (2006.01) |
| *A61K 9/50* | (2006.01) |

(52) U.S. Cl.
CPC ........ *C12N 15/113* (2013.01); *C12N 15/1135* (2013.01); *C12N 15/88* (2013.01); *A23V 2002/00* (2013.01); *A61K 9/127* (2013.01); *A61K 9/5068* (2013.01); *C12N 2310/14* (2013.01)

(56) References Cited

U.S. PATENT DOCUMENTS

| | | |
|---|---|---|
| 7,056,704 B2 | 6/2006 | Tuschl et al. |
| 7,198,923 B1 | 4/2007 | Abrignani et al. |
| 7,405,292 B2 | 7/2008 | Finkel et al. |
| 7,659,389 B2 | 2/2010 | McSwiggen et al. |
| 9,085,778 B2 | 7/2015 | Lotvall et al. |
| 9,469,876 B2 | 10/2016 | Kuslich et al. |
| 9,518,125 B2 | 12/2016 | Yong et al. |
| 9,629,929 B2 | 4/2017 | Lotvall et al. |
| 9,856,477 B2 | 1/2018 | Lotvall et al. |
| 9,889,210 B2 | 2/2018 | Lotvall et al. |
| 9,921,223 B2 | 3/2018 | Kalluri et al. |
| 2003/0064949 A1 | 4/2003 | Nielsen et al. |
| 2004/0028692 A1 | 2/2004 | Zitvogel et al. |
| 2004/0197314 A1 | 10/2004 | Delcayre et al. |
| 2004/0224893 A1 | 11/2004 | Wang et al. |
| 2005/0119215 A1 | 6/2005 | Al-Mahmood et al. |
| 2007/0298118 A1 | 12/2007 | Lotvall et al. |
| 2009/0041807 A1 | 2/2009 | Gorringe et al. |
| 2009/0252749 A1 | 10/2009 | Leister et al. |
| 2010/0196426 A1 | 8/2010 | Skog et al. |
| 2011/0054009 A1 | 3/2011 | Croce et al. |
| 2011/0237450 A1 | 9/2011 | Klass et al. |
| 2012/0196285 A1 | 8/2012 | Okamoto et al. |
| 2012/0238467 A1 | 9/2012 | Taylor et al. |
| 2013/0156801 A1 | 6/2013 | Bond et al. |
| 2013/0209544 A1 | 8/2013 | Zhang et al. |
| 2013/0273544 A1 | 10/2013 | Vlassov et al. |
| 2014/0044647 A1 | 2/2014 | Gho et al. |
| 2014/0179006 A1 | 6/2014 | Zhang |
| 2014/0234263 A1 | 8/2014 | Shiels |
| 2015/0079631 A1 | 3/2015 | Breakefield et al. |
| 2015/0232883 A1 | 8/2015 | Dahlman et al. |
| 2015/0290343 A1 | 10/2015 | Lotvall et al. |
| 2015/0301058 A1 | 10/2015 | Schettini et al. |
| 2016/0024503 A1 | 1/2016 | Kalluri et al. |
| 2016/0113966 A1 | 4/2016 | Klingemann |
| 2016/0168572 A1 | 6/2016 | Lotvall et al. |
| 2016/0245812 A1 | 8/2016 | Rak et al. |
| 2017/0059572 A1 | 3/2017 | Kalluri et al. |
| 2017/0137892 A1 | 5/2017 | Taylor et al. |
| 2018/0045728 A1 | 2/2018 | Kalluri et al. |
| 2018/0135056 A1 | 5/2018 | Lotvall et al. |
| 2018/0177727 A1 | 6/2018 | Kalluri et al. |
| 2018/0236104 A1 | 8/2018 | Lotvall et al. |

FOREIGN PATENT DOCUMENTS

| | | |
|---|---|---|
| CN | 101869715 A | 10/2010 |
| CN | 105051192 A | 11/2015 |
| CN | 105264092 A | 1/2016 |
| CN | 105821081 A | 8/2016 |
| CN | 105838739 A | 8/2016 |
| CN | 105886535 A | 8/2016 |
| CN | 107980004 A | 5/2018 |
| EP | 2578236 A1 | 4/2013 |
| EP | 2010663 B1 | 3/2015 |
| EP | 2905339 A1 | 8/2015 |
| EP | 2971162 A1 | 1/2016 |
| EP | 3076949 A1 | 10/2016 |
| EP | 3307890 A1 | 4/2018 |
| EP | 2920306 B1 | 6/2018 |
| EP | 3378942 A1 | 9/2018 |
| HK | 1227707 | 10/2017 |
| JP | 2016502404 A | 1/2016 |
| JP | 2016520803 A | 7/2016 |
| JP | 2017501694 A | 1/2017 |
| JP | 2018520125 A | 7/2018 |
| WO | WO 2000-028001 | 5/2000 |
| WO | WO 2001-036601 | 5/2001 |
| WO | WO 2001-093836 | 10/2002 |
| WO | WO 2002-082904 | 10/2002 |
| WO | WO 2003-011330 | 2/2003 |
| WO | WO 2003-016522 | 2/2003 |
| WO | WO 2003-044166 | 5/2003 |
| WO | WO 2004-014954 | 2/2004 |
| WO | WO 2005-121369 | 12/2005 |
| WO | WO 2007-126386 | 11/2007 |
| WO | WO 2009-015357 | 1/2009 |
| WO | WO 2009-147519 | 12/2009 |
| WO | WO 2010-056337 | 5/2010 |
| WO | WO 2010-119256 | 10/2010 |
| WO | WO 2011-133504 | 10/2011 |
| WO | WO 2011-147175 | 12/2011 |
| WO | WO 2012-048372 | 4/2012 |
| WO | WO 2012-125471 | 9/2012 |
| WO | WO 2012/131733 A2 | 10/2012 |
| WO | WO 2013-022995 | 2/2013 |
| WO | WO 2013-185032 | 12/2013 |
| WO | WO 2014-076137 | 5/2014 |
| WO | WO 2014-152622 | 9/2014 |
| WO | WO 2014-168548 | 10/2014 |
| WO | WO 2015-085096 | 6/2015 |
| WO | WO 2016-057755 | 4/2016 |
| WO | WO 2016-077639 | 5/2016 |
| WO | WO 2016-201323 | 12/2016 |
| WO | WO 2017/072744 A1 | 5/2017 |
| WO | WO 2017-161010 | 9/2017 |
| WO | WO 2018-039119 | 3/2018 |

OTHER PUBLICATIONS

Luga et al. (Cell, 2012 vol. 151:1542-1556).*
Kamerkar et al. (Nature, 2017 vol. 546:498-503, plus Supplementary Data).*
Ha et al. (Acta Pharmaceutica Sinica B, 2016 vol. 6:287-296).*
Chao et al. (Curr Opin Immunol., 2012 vol. 24:225-232).*
Braasch et al. (Biochemistry, 2003 vol. 42:7967-7975).*
Ghayad et al. (Scientific Reports, 2016 vol. 6:1-15).*

(56) References Cited

OTHER PUBLICATIONS

"DeliverX™ and DeliverX Plus siRNA Transfection Kits: User Manual," Panomics, Inc., 2003, 20 pages.
Adamczyk et al., "Characterization of soluble and exosomal forms of the EGFR released from pancreatic cancer cells," *Life Sciences*, 89:304-312, 2011.
Admyre et al., Abstract of "Exosomes with Major Histocompatibility Complex Class II and Co-Stimulatory Molecules are Present in Human BAL Fluid," *Eur. Respir. J.*, 4:578-583.
Almoguera et al., "Most human carcinomas of the exocrine pancreas contain mutant c-K-ras genes," *Cell*, 53:549-554, 1988.
Al-Nedawi et al., "Intercellular transfer of the oncogenic receptor EGFRvIII by microvesicles derived from tumour cells," *Nat. Cell Biol.*, 10:619-624, 2008.
Alvarez-Ervetti et al., "Delivery of siRNA to the mouse brain by systemic injection of targeted exosomes," *Nature Biotechnol.*, 29(4):341-345, 2011.
Ambros, "The functions of animal microRNAs," *Nature*, 431:350-355, 2004.
Andre et al., "Malignant effusions and immunogenic tumour-derived exosomes," *Lancet*, 360:295-305, 2002.
Arroyo et al., "Argonaute2 complexes carry a population of circulating microRNAs independent of vesicles in human plasma," *Proceedings of the National Academy of Sciences of the United States of America*, 108:5003-5008, 2011.
Baietti et al., "Syndecan-syntenin-ALIX regulates the biogenesis of exosomes," *Nat. Cell Biol.*, 14(7):677-685, 2012.
Baj-Krzyworzeka et al., "Tumour-Derived Microvesicles Carry Several Surface Determinants and mRNA of Tumour Cells and Transfer Some of These Determinants to Monocytes," *Cancer Immunol. Immunother.*, 55:808-818, 2006.
Balaj et al., "Tumour microvesicles contain retrotransposon elements and amplified oncogene sequences," *Nature Communications*, 2:180, 2011.
Ballehaninna and Chamberlain, "Biomarkers for pancreatic cancer: promising new markers and options beyond CA 19-9," *Tumour Biology*, 34:3279-3292, 2013.
Baran et al., "Circulating tumour-derived microvesicles in plasma of gastric cancer patients," *Cancer Immunology, Immunotherapy*, 59:841-850, 2010.
Bartel, "MicroRNAs: target recognition and regulatory functions," *Cell*, 136:215-233, 2009.
Bartels and Tsongalis, "MicroRNAs: novel biomarkers for human cancer," *Clinical Chemistry*, 55:623-631, 2009.
Beckler et al., "Proteomic analysis of exosomes from mutant KRAS colon cancer cells identifies intercellular transfer of mutant KRAS," *Molecular & Cellular Proteomics: MCP*, 12:343-355, 2013.
Bellavia et al. "Interleukin 3-receptor targeted exosomes inhibit in vitro and in vivo Chronic Myelogenous Leukemia cell growth," *Theranostics*, 7:1333-1345, 2017.
Belov et al., "Extensive Surface Protein Profiles of Extracellular Vesicles from Cancer Cells May Provide Diagnostic Signatures from Blood Samples," *Journal of Extracellular Vesicles*, 5:1-12, 2016.
Bernstein et al., "Dicer is essential for mouse development," *Nature Genetics*, 35:215-217, 2003.
Biankin et al., "Pancreatic cancer genomes reveal aberrations in axon guidance pathway genes," *Nature*, 491:399-405, 2012.
Cai et al., "Extracellular vesicle-mediated transfer of donor genomic DNA to recipient cells is a novel mechanism for genetic influence between cells," *J. Mol. Cell Biol.*, 5(4):227-238, 2013.
Chang et al., "Pancreatic cancer genomics," *Curr. Opin. Genetics Develop.*, 24:74-81, 2014.
Chaput et al., "The potential of exosomes in immunotherapy," *Expert Opinion on Biological Therapy*, 5:737-747, 2005.
Chen et al., "BEAMing and Droplet Digital PCR Analysis of Mutant IDH1 mRNA in Glioma Patient Serum and Cerebrospinal Fluid Extracellular Vesicles," *Molecular Therapy. Nucleic Acids*, 2:e109, 2013.
Chen et al., "Reversal of the phenotype by K-rasval12 silencing mediated by adenovirus-delivered siRNA in human pancreatic cancer cell line PANC-1," World J. Gastroenterol., 11(6):831-838, 2005.
Chendrimada et al., "TRBP recruits the Dicer complex to Ago2 for microRNA processing and gene silencing," *Nature*, 436:740-744, 2005.
Choi et al., "The protein interaction network of extracellular vesicles derived from human colorectal cancer cells," *Journal of Proteome Research*, 11:1144-1151, 2012.
Ciravolo et al., "Potential role of HER2-overexpressing exosomes in countering trastuzumab-based therapy," *Journal of Cellular Physiology*, 227:658-667, 2012.
Clayton et al., "Antigen-presenting cell exosomes are protected from complement-mediated lysis by expression of CD55 and CD59," *Eur. J. Inununol.*, 33:522-531, 2003.
Cocucci et al., "Shedding microvesicles: artefacts no more," *Trends Cell Biol*, 19:43-51, 2009.
Collins et al., "Metastatic pancreatic cancer is dependent on oncogenic Kras in mice," *PLoS One*, 7:e49707, 2012.
Collins et al., "Oncogenic Kras is required for both the initiation and maintenance of pancreatic cancer in mice," *J. Clin. Invest.*, 122:639-653, 2012.
Cooper et al., "Systemic exosomal siRNA delivery reduced alpha-synuclein aggregates in brains of transgenic mice," *Movement Disorders*, 29:1476-1485, 2014.
Couzin, "The Ins and Outs of Exosomes," *Science*, 308:1862-1863, 2005.
Crowley et al., "Liquid biopsy: monitoring cancer-genetics in the blood," *Nature Reviews, Clinical Oncology*, 10:472-484, 2013.
De Laurentiis et al., "Mass spectrometry-based identification of the tumor antigen UN1 as the transmembrane CD43 sialoglycoprotein," *Mol Cell Proteomics*, 10(5):M111.007898, 2011.
Del Villano et al., "Radioimmunometric assay for a monoclonal antibody-defined tumor marker, CA 19-9," *Clinical Chemistry*, 29:549-552, 1983.
Delcayre et al., "Exosomes as Novel Therapeutic Nanodevices," *Current Opinion in Molecular Therapeutics*, 8:31-38, 2006.
Du et al., "A systematic analysis of the silencing effects of an active siRNA at all single-nucleotide mismatched target sites," *Nucleic Acids Res.*, 33:1671-1677, 2005.
El Andaloussi et al., "Exosomes for Targeted siRNA Delivery Across Biological Barriers," *Advanced Drug Delivery Reviews*, 65:391-397, 2013.
Eldh et al., "Exosomes Communication Protective Messages During Oxidative Stress; Possible Role of Exosomal Shuttle RNA," *PLoS One*, 5:e15353, 2010.
Escola et al., "Selective enrichment of tetraspan proteins on the internal vesicles of multivesicular endosomes and on exosomes secreted by human B-lymphocytes," *The Journal of Biological Chemistry*, 273:20121-20127, 1998.
Escudier et al., "Vaccination of metastatic melanoma patients with autologous dendritic cell (DC) derived-exosomes: results of the first phase 1 clinical trial," *J. Transl. Med.*, 3(10):1-13, 2005.
Eser et al., "Oncogenic KRAS signalling in pancreatic cancer," *Br. J. Cancer*, 111:817-822, 2014.
European Patent Office, European Examination Report and Supplementary Search Report, European Patent Application No. 07748459.0, dated Oct. 8, 2010, 7 pages.
European Patent Office, European Examination Report, European Application No. 15158949.6, dated Oct. 19, 2016, 6 pages.
European Patent Office, European Examination Report, European Application No. 15158949.6, dated Mar. 13, 2018, 3 pages.
European Patent Office, European Examination Report, European Application No. 15158949.6, dated Jun. 7, 2016, 4 pages.
European Patent Office, European Examination Report, European Application No. 15158949.6, dated Jun. 2, 2017, 4 pages.
European Patent Office, European Examination Report, European Application No. 13789802.9, dated Sep. 23, 2016, 5 pages.
European Patent Office, European Extended Search Report, European Application No. 15158949.6, dated Jul. 13, 2015, 9 pages.
European Patent Office, European Extended Search Report, European Application No. 07748459.0, dated Oct. 18, 2010, 8 pages.

(56) References Cited

OTHER PUBLICATIONS

European Patent Office, European Second Examination Report, European Application No. 13789802.9, dated Jul. 6, 2017, 3 pages.
European Patent Office, European Summons to Attend Oral Proceedings Pursuant to Rule 115(1) EPC, European Application No. 07748459.0, Apr. 24, 2014, 7 pages.
European Patent Office, Extended European Search Report, European Application No. 18158203.2, dated Aug. 21, 2018, 12 pages.
European Patent Office, Office Action, European Patent Application No. 07748459.0, dated Jun. 27, 2012, 5 pages.
European Patent Office, Office Action, European Patent Application No. 07748459.0, dated Jun. 17, 2013, 4 pages.
European Patent Office, Office Action, European Patent Application No. 07748459.0, dated Jul. 6, 2011, 6 pages.
European Patent Office, Partial Supplementary European Search Report, European Application No. 14867768.5, dated Jul. 17, 2017, 15 pages.
Extended European Search Report issued in corresponding European Patent Application No. 14867768.5, dated Oct. 19, 2017.
Extended European Search Report issued in European Application No. 14770497.7, dated Oct. 14, 2016.
Filipowicz, "RNAi: the nuts and bolts of the RISC machine," *Cell*, 122:17-20, 2005.
Fleming et al., "Molecular consequences of silencing mutant K-ras in pancreatic cancer cells: justification for K-ras-directed therapy," *Mol. Cancer Res.*, 3(7):413-423, 2005.
Fukagawa et al., "Dicer is essential for formation of the heterochromatin structure in vertebrate cells," *Nature Cell Biology*, 6:784-791, 2004.
Gallo et al., "The majority of microRNAs detectable in serum and saliva is concentrated in exosomes," *PloS One*, 7:e30679, 2012.
Gehl, "Electroporation: theory and methods, perspectives for drug delivery, gene therapy and research," *Acta Physiologica Scandinavica*, 177:437-447, 2003.
Gibbings et al., "Multivesicular bodies associate with components of miRNA effector complexes and modulate miRNA activity," *Nature Cell Biology*, 11:1143-1149, 2009.
Gomes-da-Silva et al., "Lipid-based nanoparticles for siRNA delivery in cancer therapy: paradigms and challenges," *Acc. Chem. Res.*, 45:1163-1171, 2012.
Grange et al., "Microvesicles released from human renal cancer stem cells stimulate angiogenesis and formation of lung premetastatic niche," *Cancer Research*, 71:5346-5356, 2011.
Grelier et al., "Prognostic value of Dicer expression in human breast cancers and association with the mesenchymal phenotype," *British Journal of Cancer*, 101:673-683, 2009.
Groth et al., "ATP Synthase from Bovine Heart Mitochondria: Reconstitution into Unilamellar Phospholipid Vesicles of the Pure Enzyme in a Functional State," *Biochemical Journal*, 318:351-357, 1996.
Guermonprez et al., "Antigen presentation and T cell stimulation by dendritic cells," *Annu Rev Immunol*, 20:621-667, 2002.
Guescini et al., "Astrocytes and Glioblastoma cells release exosomes carrying mtDNA," *J Neural Transm*, 117:1-4, 2010.
Guescini et al., "C2C12 myoblasts release micro-vesicles containing mtDNA and proteins involved in signal transduction," *Experimental Cell Research*, 316:1977-1984, 2010.
Gyorgy et al., "Membrane vesicles, current state-of-the-art: emerging role of extracellular vesicles," *Cell Mol Life Sci*, 68:2667-2688, 2011.
Gysin et al., "Therapeutic strategies for targeting ras proteins," *Genes & Cancer*, 2:359-372, 2011.
Hingorani et al., "Trp53R172H and KrasG12D cooperate to promote chromosomal instability and widely metastatic pancreatic ductal adenocarcinoma in mice," *Cancer Cell*, 7:469-483, 2005.
Hirata et al., "Oncogenic miRNA-182-5p targets Smad4 and RECK in human bladder cancer," *PloS One*, 7:e51056, 2012.
Hood et al., "Exosomes released by melanoma cells prepare sentinel lymph nodes for tumor metastasis," *Cancer research*, 71:3792-3801, 2011.
Hruban et al., "K-ras oncogene activation in adenocarcinoma of the human pancreas. A study of 82 carcinomas using a combination of mutant-enriched polymerase chain reaction analysis and allele-specific oligonucleotide hybridization," *Am. J. Pathol.*, 143:545-554, 1993.
Iglehart et al., "Synthetic lethality—a new direction in cancer-drug development," *New Engl. J. Med.*, 361(2):189-191, 2009.
International Preliminary Report on Patentability issued in corresponding PCT Application No. PCT/US2016/037018, dated Dec. 12, 2017.
International Search Report and Written Opinion issued in corresponding PCT Application No. PCT/US2016/037018, dated Oct. 14, 2016.
Ismail et al., "Macrophage microvesicles induce macrophage differentiation and miR-223 transfer," *Blood*, 121:984-995, 2013.
Japan Patent Office, Japanese Office Action, Japanese Application No. 2015-542258, dated Nov. 8, 2017, 10 pages.
Jazieh et al., "The clinical utility of biomarkers in the management of pancreatic adenocarcinoma," *Seminars in Radiation Oncology*, 24:67-76, 2014.
Ji et al., "Proteome profiling of exosomes derived from human primary and metastatic colorectal cancer cells reveal differential expression of key metastatic factors and signal transduction components," *Proteomics*, 13:1672-1686, 2013.
Ji et al., "Ras activity levels control the development of pancreatic diseases," *Gastroenterology*, 137:1072-1082, 82 e1-6, 2009.
Johnsen et al., "A comprehensive overview of exosomes as drug delivery vehicles—Endogenous nanocarriers for targeted cancer therapy," *Biochim. Biophys. Acta, Rev. Cancer*, 1846(1):75-87, 2014.
Kahlert and Kalluri, "Exosomes in tumor microenvironment influence cancer progression and metastasis," *J. Mol. Med. (Berl.)*, 91:431-437, 2013.
Kahlert et al., "Identification of double-stranded genomic DNA spanning all chromosomes with mutated KRAS and p53 DNA in the serum exosomes of patients with pancreatic cancer," *The Journal of Biological Chemistry*, 289:3869-3875, 2014.
Karube et al., "Reduced expression of Dicer associated with poor prognosis in lung cancer patients," *Cancer science*, 96:111-115, 2005.
Khvalevsky et al., "Mutant KRAS is a druggable target for pancreatic cancer," *Proc. Natl. Acad. Sci. USA*, 110:20723-20728, 2013.
King et al., "Hypoxic enhancement of exosome release by breast cancer cells," *BMC Cancer*, 12:421, 2012.
Kleeff et al., "The cell-surface heparan sulfate proteoglycan glypican-1 regulates growth factor action in pancreatic carcinoma cells and is overexpressed in human pancreatic cancer," *The Journal of Clinical Investigation*, 102:1662-1673, 1998.
Kogure et al., "Intercellular nanovesicle-mediated microRNA transfer: a mechanism of environmental modulation of hepatocellular cancer cell growth," *Hepatology*, 54:1237-1248, 2011.
Kooijmans et al., "Modulation of tissue tropism and biological activity of exosomes and other extracellular vesicles: New nanotools for cancer treatment," *Pharmacological Research*, 111:487-500, 2016.
Kosaka et al., "Neutral sphingomyelinase 2 (nSMase2)-dependent exosomal transfer of angiogenic microRNAs regulate cancer cell metastasis," *The Journal of Biological Chemistry*, 288:10849-10859, 2013.
Kosaka et al., "Trash or Treasure: extracellular microRNAs and cell-to-cell communication," *Frontiers in Genetics*, 4:173, 2013.
Kovacs Bagdan et al., "Reconstitution of the Mitochondrial Calcium Uniporter in Yeast," *Proc. Natl. Acad. Sci. U.S.A.*, 111:8985-8990, 2014.
Kumar et al., "Impaired microRNA processing enhances cellular transformation and tumorigenesis," *Nature genetics*, 39:673-677, 2007.
Lai et al., "Mesenchymal Stem Cell Exosome: a Novel Stem Cell-Based Therapy for Cardiovascular Disease," *Regenerative Medicine*, 6:481-492, 2011.
Lakshmikuttyamma et al., "Stable and Efficient Transfection of siRNA for Mutated KRAS Silencing Using Novel Hybrid Nanoparticles," *Mol. Pharm.*, 11(12):4415-4424, 2014.

(56) References Cited

OTHER PUBLICATIONS

Lasser, "Exosomes in Diagnostic and Therapeutic Applications: Biomarker, Vaccine and RNA Interference Delivery Vehicle," *Expert Opinion on Biological Therapy*, 15:103-117, 2015.

Lau et al., "Role of Pancreatic Cancer-derived Exosomes in Salivary Biomarker Development," with Supplemental material, *The Journal of Biological Chemistry*, 288:26888-26897, 2013.

Lederberg, "The Transformation of Genetics by DNA: an Anniversary Celebration of Avery, Macleod and McCarty (1944)," *Genetics*, 136: 423-426, 1994.

Lee et al., "Exosomes and microvesicles: extracellular vesicles for genetic information transfer and gene therapy," *Human Molecular Genetics*, 21:R125-R134, 2012.

Lee et al., "Microvesicles as mediators of intercellular communication in cancer—the emerging science of cellular 'debris'," *Semin Immunopathol*, 33:455-467, 2011.

Lener et al., "Applying Extracellular Vesicles Based Therapeutics in Clinical Trials—an ISEV Position Paper," *Journal of Extracellular Vesicles*, 4:30087, 2015.

Li et al., "Argonaute 2 complexes selectively protect the circulating microRNAs in cell-secreted microvesicles," *PLoS One*, 7:e46957, 2012.

Li et al., "Claudin-containing exosomes in the peripheral circulation of women with ovarian cancer," *BMC Cancer*, 9(1):244, 2009.

Lin et al. "Biodegradable nancapsules as siRNA carriers for mutant K-Ras gene silencing of human pancreatic cancer cells," *Small*, 9(16):2757-2763, 2013.

Lin et al., Abstract of "Human Small Intestinal Epithelial Cells Constitutively Express the Key Elements for Antigen Processing and the Production for Exosomes," *Blood Cells Mol. Dis.*, 35:122-128, 2005.

Liu et al., "MicroRNA expression profiling using microarrays," *Nat Protoc*, 3:563-578, 2008.

Logozzi et al., "High levels of exosomes expressing CD63 and caveolin-1 in plasma of melanoma patients," *PloS one*, 4:e5219, 2009.

Lotvall et al., "Cell to Cell Signaling Via Exosomes Through esRNA," *Cell Adhesion & Migration*, 1:156-158, 2007.

Lotvall et al., "Minimal Experimental Requirements for Definition of Extracellular Vesicles and Their Functions: a Position Statement from the International Society for Extracellular Vesicles," *Journal of Extracellular Vesicles*, 3:26913, 2014.

Lu et al., "MicroRNA expression profiles classify human cancers," *Nature*, 435:834-838, 2005.

Luga et al., "Exosomes Mediate Stromal Mobilization of Autocrine Wnt-PCP Signaling in Breast Cancer Cell Migration," *Cell*, 151:1542-1556, 2012.

Luo et al., "Immunotherapy of Dendritic Cells and Its Exosomes Transfected with mRNA of Gastric Cancer Cells in Tumor-Carried Mice," *World Chin. J. Digestol.*, 12:9-12, 2004.

Luzio et al., "The delivery of endocytosed cargo to lysosomes," *Biochemical Society transactions*, 37:1019-1021, 2009.

Ma et al., "Structural basis for overhang-specific small interfering RNA recognition by the PAZ domain," *Nature*, 429:318-322, 2004.

Ma et al., "Tumour invasion and metastasis initiated by microRNA-10b in breast cancer," *Nature*, 449:682-688, 2007.

Macfarlane et al., "MicroRNA: biogenesis, function and role in cancer," *Current Genomics*, 11(7):537-561, 2010.

Maehama, "PTEN: its deregulation and tumorigenesis," *Biological & pharmaceutical bulletin*, 30:1624-1627, 2007.

Maniataki and Mourelatos, "A human, ATP-independent, RISC assembly machine fueled by pre-miRNA," *Genes & development*, 19:2979-2990, 2005.

Mao et al., "Serum miR-21 is a diagnostic and prognostic marker of primary central nervous system lymphoma," *Neurological Sciences*, 35(2):233-238, 2014.

Marcus and Leonard, "FedExosomes: Engineering Therapeutic Biological Nanoparticles that Truly Deliver," *Pharmaceuticals*, 6(5):659-680, 2013.

Martello et al., "A MicroRNA targeting dicer for metastasis control," *Cell*, 141:1195-1207, 2010.

Mathivanan et al., "Exosomes: extracellular organelles important in intercellular communication," *Journal of proteomics*, 73:1907-1920, 2010.

Matsuda et al., "Glypican-1 is overexpressed in human breast cancer and modulates the mitogenic effects of multiple heparin-binding growth factors in breast cancer cells," *Cancer Research*, 61:5562-5569, 2001.

Mavel et al., "Synthesis of imidazo[2,1-a]phthalazines, potential inhibitors of p38 MAP kinase. Prediction of binding affinities of protein ligands," *Arch Pharm (Weinheim)*, 335:7-14, 2002.

McCready et al., "Secretion of extracellular hsp90alpha via exosomes increases cancer cell motility: a role for plasminogen activation," *BMC cancer*, 10:294, 2010.

McMahon et al., "Biomimetic High Density Lipoprotein Nanoparticles for Nucleic Acid Delivery," *Nano Letters*, 11:1208-1214, 2011.

Mears et al., "Proteomic analysis of melanoma-derived exosomes by two-dimensional polyacrylamide gel electrophoresis and mass spectrometry," *Proteomics*, 4:4019-4031, 2004.

Medici and Kalluri, "Endothelial-mesenchymal transition and its contribution to the emergence of stem cell phenotype," *Semin. Cancer Biol.*, 22:379-384, 2012.

Melo et al., "A genetic defect in exportin-5 traps precursor microRNAs in the nucleus of cancer cells," *Cancer cell*, 18:303-315, 2010.

Melo et al., "A TARBP2 mutation in human cancer impairs microRNA processing and DICER1 function," *Nature genetics*, 41:365-370, 2009.

Melo et al., "Cancer exosomes perform cell-independent microRNA biogenesis and promote tumorigenesis," *Cancer Cell*, 26(5):707-721, 2014.

Melo et al., "Glypican-1 identifies cancer exosomes and detects early pancreatic cancer," *Nature*, 523:177-182, 2015.

Melo et al., "Small molecule enoxacin is a cancer-specific growth inhibitor that acts by enhancing TAR RNA-binding protein 2-mediated microRNA processing," *Proceedings of the National Academy of Sciences of the United States of America*, 108:4394-4399, 2011.

Merritt et al., "Dicer, Drosha, and outcomes in patients with ovarian cancer," *The New England journal of medicine*, 359:2641-2650, 2008.

Mittelbrunn et al., "Unidirectional transfer of microRNA-loaded exosomes from T cells to antigen-presenting cells," *Nature communications*, 2:282, 2011.

Miyata, "Hsp90 inhibitor geldanamycin and its derivatives as novel cancer chemotherapeutic agents," *Current pharmaceutical design*, 11:1131-1138, 2005.

Montecalvo et al., "Mechanism of transfer of functional microRNAs between mouse dendritic cells via exosomes," *Blood*, 119:756-766, 2012.

Moore et al., "Genetic profile of 22 pancreatic carcinoma cell lines. Analysis of K-ras, p53, p16 and DPC4/Smad4," *Virchows Arch.*, 439:798-802, 2001.

Morris et al., "KRAS, Hedgehog, Wnt and the twisted developmental biology of pancreatic ductal adenocarcinoma," *Nature Reviews, Cancer*, 10:683-695, 2010.

Moss et al., "Shedding of Membrane Proteins by ADAM Family Proteases," *Essays in Biochemistry*, 38:141-154, 2002.

Mouliere and Thierry, "The importance of examining the proportion of circulating DNA originating from tumor, microenvironment and normal cells in colorectal cancer patients," *Expert Opinion on Biological Therapy*, 12(Suppl. 1):S209-215, 2012.

Murtaza et al., "Non-invasive analysis of acquired resistance to cancer therapy by sequencing of plasma DNA," *Nature*, 497:108-112, 2013.

Nabel et al., "Immune response in human melanoma after transfer of an allogeneic class I major histocompatibility complex gene with DNA-liposome complexes," *Proc. Natl. Acad. Sci. U.S.A.*, 93:15388-15393, 1996.

Narayanan et al., "Exosomes derived from HIV-1-infected cells contain trans-activation response element RNA," *The Journal of biological chemistry*, 288:20014-20033, 2013.

(56) References Cited

OTHER PUBLICATIONS

Nicoloso et al., "MicroRNAs—the micro steering wheel of tumour metastases," *Nature reviews Cancer*, 9:293-302, 2009.
Nolte-'t Hoen et al., "Deep sequencing of RNA from immune cell-derived vesicles uncovers the selective incorporation of small non-coding RNA biotypes with potential regulatory functions," *Nucleic Acids Research*, 40:9272-9285, 2012.
O'Brien et al., "Converting cancer mutations into therapeutic opportunities," *EMBO Mol. Med.*, 1:297-299, 2009.
Office Action issued in Chinese Application No. 201480022292.7, dated Dec. 4, 2017, and English language translation thereof.
Office Action issued in European Application No. 14770497.7, dated Oct. 20, 2017.
Ohno et al., "Systemically injected exosomes targeted to EGFR deliver antitumor microRNA to breast cancer cells," *Mol. Ther.*, 21(1):185-191, 2013.
Ohshima et al., "Let-7 MircoRNA Family Is Selectively Secreted into the Extracellular Environment via Exosomes in a Metastatic Gastric Cancer Cell Line," *PLoS One*, 5:e13247, 2010.
Okita et al., "A more efficient method to generate integration-free human iPS cells," *Nature Methods*, 8:409-412, 2011.
Oldenborg, "Role of CD47 as a Marker of Self on Red Blood Cells," *Science*, 288(5473):2051-2054, 2000.
Ostrowski et al., "Rab27a and Rab27b control different steps of the exosome secretion pathway," *Nature cell biology*, 12:19-30; sup pp. 11-13, 2010.
Ozen et al., "Widespread deregulation of microRNA expression in human prostate cancer," *Oncogene*, 27:1788-1793, 2008.
Pant et al., "The multifaceted exosome: biogenesis, role in normal and aberrant cellular function, and frontiers for pharmacological and biomarker opportunities," *Biochemical pharmacology*, 83:1484-1494, 2012.
Park et al., "Neuroprotective effect of human mesenchymal stem cells in an animal model of double toxin-induced multiple system atrophy parkinsonism," *Cell Transplant*, 20:827-835, 2011.
Partial Supplementary European Search Report issued in European Application No. 14867768.5, dated Jul. 17, 2017.
PCT International Preliminary Report on Patentability, PCT Application No. PCT/US2016/037018, dated Dec. 12, 2017, 9 pages.
PCT International Search Report and Written Opinion, PCT Application No. PCT/US2016/037018, dated Oct. 14, 2016, 17 pages.
PCT International Preliminary Report on Patentability issued in International Application No. PCT/US2014/027541, dated Sep. 15, 2015.
PCT International Preliminary Report on Patentability issued in International Application No. PCT/US2014/068630, dated Jun. 7, 2016.
PCT International Preliminary Report on Patentability, PCT Application No. PCT/EP2013/073740, dated May 28, 2015, 10 pages.
PCT International Search Report and Written Opinion issued in International Application No. PCT/US2014/027541, dated Jul. 21, 2014.
PCT International Search Report and Written Opinion issued in International Application No. PCT/US2014/068630, dated Feb. 23, 2015.
PCT International Search Report and Written Opinion, PCT Application No. PCT/SE2007/050298, dated Sep. 14, 2007, 15 pages.
PCT International Search Report and Written Opinion, PCT Application No. PCT/EP2013/073740, dated Apr. 24, 2014, 7 pages.
PCT International Search Report and Written Opinion, PCT Application No. PCT/US2017/022544, dated Jun. 16, 2017, 16 pages.
PCT International Search Report and Written Opinion, PCT Application No. PCT/US2018/048026, dated Oct. 30, 2018, 23 pages.
Pecot et al., "Therapeutic Silencing of KRAS Using Systemically Delivered siRNAs," *Mol. Cancer Ther.*, 13(12):2876-2885, 2014.
Pegtel et al., "Functional delivery of viral miRNAs via exosomes," *Proc. Natl. Acad. Sci. U.S.A.*, 107:6328-6333, 2010.
Peinado et al., "Melanoma exosomes educate bone marrow progenitor cells toward a pro-metastatic phenotype through MET," *Nat. Med.*, 18:883-891, 2012.
Pisitkun et al., "Identification and proteomic profiling of exosomes in human urine," *Proc. Natl. Acad. Sci. U.S.A.*, 101:13368-13373, 2004.
Ponsaerts et al., "Editorial: Modulation of Cellular Behavior by Exogenous Messenger RNA," *Leukemia*, 20:767-769, 2006.
Properzi et al., "Exosomes: the future of biomarkers in medicine," *Biomarkers in Medicine*, 7(5):769-778, 2013.
Rachagani et al., "Activated KrasG12D is associated with invasion and metastasis of pancreatic cancer cells through inhibition of E-cadherin," *Br. J. Cancer*, 104:1038-1048, 2011.
Ramachandran et al., "Horizontal transfer of RNAs: exosomes as mediators of intercellular communication," *Wiley Interdiscip Rev RNA*, 3(2):286-293, 2012.
Raposo and Stoorvogel, "Extracellular vesicles: exosomes, microvesicles, and friends," *The Journal of Cell Biology*, 200:373-383, 2013.
Raposo et al., "B Lymphocytes Secrete Antigen-Presenting Vesicles," *J. Exp. Med.*, 183:1161-1172, 1996.
Ratajczak et al., "Embryonic stem cell-derived microvesicles reprogram hematopoietic progenitors: evidence for horizontal transfer of MRNA and protein delivery," *Leukemia*, 20:847-856, 2006.
Razi and Futter, "Distinct roles for Tsg101 and Hrs in multivesicular body formation and inward vesiculation," *Molecular Biology of the Cell*, 17:3469-3483, 2006.
Razin et al., "Interleukin 3: a Differentiation and Growth Factor for the Mouse Mast Cell That Contains Chondroitin Sulfate E Proteoglycan," *The Journal of Immunology*, 132:1479-1486, 1984.
Rejiba et al., "K-ras oncogene silencing strategy reduces tumor growth and enhances gemcitabine chemotherapy efficacy for pancreatic cancer treatment," *Cancer Sci.*, 98:1128-1136, 2007.
Roccaro et al., "BM mesenchymal stromal cell-derived exosomes facilitate multiple myeloma progression," *The Journal of clinical investigation*, 123(4):1542-1555, 2013.
Rodriguez, "Minimal "self" peptides that inhibit phagocytic clearance and enhance delivery of nanoparticles," *Science*, 339:971-975, 2013.
Ronquist et al., "Human prostasomes contain chromosomal DNA," *Prostate*, 69(7):737-746, 2009.
Ronquist et al., "Prostasomes are heterogeneous regarding size and appearance but affiliated to one DNA-containing exosome family," *Prostate*, 72(16):1736-1745, 2012.
Ronquist et al., "Prostasomal DNA characterization and transfer into human sperm," *Mol. Reprod. Dev.*, 78(7):467-476, 2011.
Rottiers et al., "MicroRNAs in metabolism and metabolic disorders," *Nat. Rev. Mol. Cell Biol.*, 13(4):239-250, 2012.
Runz et al., "Malignant ascites-derived exosomes of ovarian carcinoma patients contain CD24 and EpCAM," *Gynecologic Oncology*, 107:563-571, 2007.
Russian Federal Service for Intellectual Property, Russian Office Action, Russian Application No. 2015144212/10 (068090), dated Jun. 19, 2017, 6 pages (with concise explanation of relevance).
Russian Federal Service for Intellectual Property, Russian Office Action, Russian Application No. 2015144212/10 (068090), dated Feb. 1, 2017, 12 pages.
Savina et al., "Exosome release is regulated by a calcium-dependent mechanism in K562 cells," *The Journal of Biological Chemistry*, 278:20083-20090, 2003.
Sen et al., "A brief history of RNAi: the silence of the genes," *The FASEB Journal*, 20(9):1293-1299, 2006.
Shen et al., "Biogenesis of the posterior pole is mediated by the exosome/microvesicle protein-sorting pathway," *The Journal of Biological Chemistry*, 286:44162-44176, 2011.
Shen et al., "EGFR modulates microRNA maturation in response to hypoxia through phosphorylation of AGO2," *Nature*, 497:383-387, 2013.
Shen et al., "Protein targeting to exosomes/microvesicles by plasma membrane anchors," *The Journal of Biological Chemistry*, 286:14383-14395, 2011.
Sherer et al., "Visualization of retroviral replication in living cells reveals budding into multivesicular bodies," *Traffic*, 4:785-801, 2003.

(56) References Cited

OTHER PUBLICATIONS

Shi et al., "Combined silencing of Kras and Akt2 oncogenes achieves synergistic effects in inhibiting pancreatic cancer cell growth in vitro and in vivo," *Cancer Gene Ther.*, 16(3):227-236, 2009.

Shin et al., "BIG2, a guanine nucleotide exchange factor for ADP-ribosylation factors: its localization to recycling endosomes and implication in the endosome integrity," *Molecular Biology of the Cell*, 15:5283-5294, 2004.

Shurtleff et al., "A Broad Role for YBX1 in Defining the Small Non-Coding RNA Composition of Exosomes," bioRxiv Preprint, First Posted Jul. 7, 2017, 42 pages.

Siegel et al., "Cancer statistics, 2014," *CA Cancer J. Clin.*, 64:9-29, 2014.

Siegel et al., "Cancer treatment and survivorship statistics, 2012," *CA Cancer J. Clin.*, 62:220-241, 2012.

Silva et al., "Analysis of exosome release and its prognostic value in human colorectal cancer," *Genes, Chromosomes & Cancer*, 51:409-418, 2012.

Simoes et al., "Cationic liposomes for gene delivery," *Exp. Opin. Drug Deliv.*, 2:237-254, 2005.

Simons and Raposo, "Exosomes—vesicular carriers for intercellular communication," *Curr Opin Cell Biol*, 21:575-581, 2009.

Simpson et al., "Extracellular Microvesicles: the Need for Internationally Recognised Nomenclature and Stringent Purification Criteria," *Proteomics & Bioinformatics*, 5:1, 2012.

Simpson et al., "Proteomic profiling of exosomes: current perspectives," *Proteomics*, 8:4083-4099, 2008.

Skog et al., "Glioblastoma microvesicles transport RNA and proteins that promote tumour growth and provide diagnostic biomarkers," *Nature Cell Biology*, 10:1470-1476, 2008.

Smakman et al., "Dual effect of Kras(D12) knockdown on tumorigenesis: increased immune-mediated tumor clearance and abrogation of tumor malignancy," *Oncogene*, 24:8338-8342, 2005.

Stoorvogel et al., "The Biogenesis and Functions of Exosomes," *Traffic*, 3:321-330, 2002.

Su et al., "Glypican-1 is frequently overexpressed in human gliomas and enhances FGF-2 signaling in glioma cells," *The American Journal of Pathology*, 168:2014-2026, 2006.

Tagami et al., "Argonaute2 is a potential target for siRNA-based cancer therapy for HT1080 human fibrosarcoma," *Drug Deliv and Transl. Res.*, 1:277-288, 2011.

Tang, "siRNA and miRNA: an insight into RISCs," *Trends Biochem Sci*, 30:106-114, 2005.

Taylor and Gercel-Taylor, "Exosomes/microvesicles: mediators of cancer-associated immunosuppressive microenvironments," *Semin Immunopathol*, 33:441-454, 2011.

Taylor and Gercel-Taylor, "MicroRNA signatures of tumor-derived exosomes as diagnostic biomarkers of ovarian cancer," *Gynecologic Oncology*, 110:13-21, 2008.

Thailand Patent Office, Office Action, Thai Application No. 1501005286, dated May 30, 2017, 2 pages.

The State Intellectual Property Office of the People's Republic of China, Office Action, CN Patent Application No. 2007800154690, dated Oct. 30, 2012, 8 pages.

The State Intellectual Property Office of the People's Republic of China, Office Action, CN Patent Application No. 201511027801.8, dated Apr. 23, 2018, 19 pages.

The State Intellectual Property Office of the People's Republic of China, Office Action, CN Patent Application No. 201511027801.8, dated Jun. 13, 2017, 22 pages.

The State Intellectual Property Office of the People's Republic of China, Office Action, CN Patent Application No. 201511027801.8, dated Dec. 7, 2016, 21 pages.

The State Intellectual Property Office of the People's Republic of China, Office Action, CN Patent Application No. 201511027801.8, dated Dec. 22, 2017, 20 pages.

The State Intellectual Property Office of the People's Republic of China, Office Action, CN Patent Application No. 201480022292.7, dated Apr. 5, 2017, 37 pages.

The State Intellectual Property Office of the People's Republic of China, Office Action, CN Patent Application No. 201380069683.X, dated Oct. 10, 2016, 12 pages (with concise explanation of relevance).

The State Intellectual Property Office of the People's Republic of China, Office Action, CN Patent Application No. 201380069683.X, dated Mar. 13, 2018, 13 pages (with concise explanation of relevance).

The State Intellectual Property Office of the People's Republic of China, Office Action, CN Patent Application No. 201380069683.X, dated Aug. 18, 2017, 16 pages (with concise explanation of relevance).

Thery and Casas, "Predator and prey views of spider camouflage," *Nature*, 415:133, 2002.

Thery et al., "Exosomes: composition, biogenesis and function," *Nat. Rev. Immunol.*, 2:569-579, 2002.

Thery et al., "Indirect activation of naive CD4+ T cells by dendritic cell-derived exosomes," *Nat. Immunol.*, 3:1156-1162, 2002.

Thery et al., "Isolation and characterization of exosomes from cell culture supernatants and biological fluids," *Current Protocols in Cell Biology*, Chapter 3, Unit 3.22, 2006.

Thery et al., "Membrane vesicles as conveyors of immune responses," *Nature Reviews, Immunology*, 9:581-593, 2009.

Thomson et al., "On measuring miRNAs after transient transfection of mimics or antisense inhibitors," *PloS One*, 8:e55214, 2013.

Tse and Kalluri, "Waking up dormant tumors," *Breast Cancer Research*, 13:310, 2011.

Turchinovich et al., "Characterization of extracellular circulating microRNA," *Nucleic Acids Research*, 39:7223-7233, 2011.

United States Office Action, U.S. Appl. No. 14/442,578, dated Jun. 8, 2017, 13 pages.

United States Office Action, U.S. Appl. No. 14/442,578, dated Nov. 22, 2016, 9 pages.

United States Office Action, U.S. Appl. No. 14/750,457, dated Mar. 25, 2016, 9 pages.

United States Office Action, U.S. Appl. No. 14/750,457, dated Nov. 3, 2016, 13 pages.

United States Office Action, U.S. Appl. No. 15/476,844, dated Oct. 19, 2017, 14 pages.

United States Office Action, U.S. Appl. No. 11/799,148, dated Sep. 3, 2009, 6 pages.

United States Office Action, U.S. Appl. No. 11/799,148, dated Sep. 29, 2010, 7 pages.

United States Office Action, U.S. Appl. No. 11/799,148, dated Nov. 7, 2014, 13 pages.

United States Office Action, U.S. Appl. No. 11/799,148, dated Mar. 26, 2014, 21 pages.

United States Office Action, U.S. Appl. No. 11/799,148, dated Dec. 17, 2010, 3 pages.

United States Office Action, U.S. Appl. No. 11/799,148, dated Apr. 2, 2010, 8 pages.

Vaishnaw et al., "A status report on RNAi therapeutics," *Silence*, 1:14-26, 2010.

Valadi et al., "Exosome-mediated transfer of mRNAs and microRNAs is a novel mechanism of genetic exchange between cells," *Nature cell biology*, 9:654-659, 2007.

Van Balkom et al., "Endothelial cells require miR-214 to secrete exosomes that suppress senescence and induce angiogenesis in human and mouse endothelial cells," *Blood*, 121:3997-4006, 2013.

Van den Boorn et al., "Exosomes as nucleic acid nanocarriers," *Adv. Drug Deliv. Rev.*, 65:331-335, 2013.

Van der Meel et al., "Extracellular vesicles as drug delivery systems: Lessons from the liposome field," *J. Control. Release*, 195:72-85, 2014.

Van der Pol et al., "Classification, Functions, and Clinical Relevance of Extracellular Vesicles," *Pharmacol. Rev.*, 64(3):676-705, 2012.

Van Dommelen et al., "Microvesicles and Exosomes: Opportunities for Cell-Derived Membrane Vesicles in Drug Delivery," *Journal of Controlled Release*, 161:635-644, 2012.

Vickers et al., "Efficient Reduction of Target RNAs by Small Interfering RNA and Rnase H-dependent Antisense Agents," *The Journal of Biological Chemistry*, 278:7108-7118, 2003.

(56) References Cited

OTHER PUBLICATIONS

Vickers et al., "MicroRNAs are transported in plasma and delivered to recipient cells by high-density lipoproteins," *Nature cell biology*, 13:423-433, 2011.
Vita et al., "The Myconcoprotein as a therapeutic target for human cancer," *Seminars in Cancer Biology*, 16:318-330, 2006.
Volinia et al., "A microRNA expression signature of human solid tumors defines cancer gene targets," *Proc. Natl. Acad. Sci. U.S.A.*, 103:2257-2261, 2006.
Wahlgren et al., "Plasma exosomes can deliver exogenous short interfering RNA to monocytes and lymphocytes," *Nucleic Acids Res.*, 40:e130, 2012.
Walker et al., "Encapsulation of bilayer vesicles by self-assembly," *Nature*, 387:61-64, 1997.
Wang et al., "c-Myc depletion inhibits proliferation of human tumor cells at various stages of the cell cycle," *Oncogene*, 27:1905-1915, 2008.
Wang et al., "Identification of effective siRNA against K-ras in human pancreatic cancer cell line MiaPaCa-2 by siRNA expression cassette," *Wolrd J. Gastroenterol.*, 11(13):2026-2031, 2005.
Whipple et al., "KrasG12D-driven genetic mouse model of pancreatic cancer requires glypican-1 for efficient proliferation and angiogenesis," *Oncogene*, 31:2535-2544, 2012.
Wiesen and Tomasi, "Dicer is regulated by cellular stresses and interferons," *Mol Immunol*, 46:1222-1228, 2009.
Xu et al., "Delivery systems for siRNA drug development in cancer therapy," *Asian J. Pharm. Sci.*, 10(1):1-12, 2015.
Xue et al., "Small RNA combination therapy for lung cancer," *Proc. Natl. Acad. Sci., U.S.A.*, 111(34):E3553-E3561, 2014.
Yan et al., "Knockdown of miR-21 in human breast cancer cell lines inhibits proliferation, in vitro migration and in vivo tumor growth," *Breast Cancer Research*, 13(1):R2, 2011.
Yan et al., "MicroRNA miR-21 overexpression in human breast cancer is associated with advanced clinical stage, lymph node metastasis and patient poor prognosis," *RNA*, 14:2348-2360, 2008.
Yang and Robbins, "The roles of tumor-derived exosomes in cancer pathogenesis," *Clin Dev Immunol*, 2011:842849, 2011.
Yang et al., "Systemic Delivery of siRNA via LCP Nanoparticle Efficiently Inhibits Lung Metastasis," *Molecular Therapy*, 20:609-615, 2012.
Yang et al., "Exosomes derived from immature bone marrow dendritic cells induce tolerogenicity of intestinal transplantation in rats," *J Surg Res*, 171:826-832, 2011.
Yang et al., "Exosome Mediated Delivery of miR-124 Promotes Neurogenesis after Ischemia," *Molecular Therapy Nucleic Acids*, 7:278-287, 2017.
Yeo et al., "Mesenchymal Stem Cell: an Efficient Mass Producer of Exosomes for Drug Delivery," *Advanced Drug Delivery Reviews*, 65:336-341, 2013.
Yi et al., "Exportin-5 mediates the nuclear export of pre-microRNAs and short hairpin RNAs," *Genes & Development*, 17:3011-3016, 2003.
Ying et al., "Oncogenic Kras maintains pancreatic tumors through regulation of anabolic glucose metabolism," *Cell*, 149:656-670, 2012.
Yong, "Cancer biomarkers: Written in blood," *Nature*, 511:524-526, 2014.
Yuan et al., "Development of siRNA payloads to target KRAS-mutant cancer," *Cancer Discov.*, 4:1182-1197, 2014.
Zeelenberg et al., "Targeting tumor antigens to secreted membrane vesicles in vivo induces efficient antitumor immune responses," *Cancer Research*, 68:1228-1235, 2008.
Zeng et al., "Combination of siRNA-directed Kras oncogene silencing and arsenic-induced apoptosis using a nanomedicine strategy for the effective treatment of pancreatic cancer," *Nanomedicine*, 1-(2):463-472, 2014.
Zernecke et al., "Delivery of microRNA-126 by apoptotic bodies induces CXCL12-dependent vascular protection," *Sci. Signal.*, 2(100):ra81, 2009.
Zhang et al., "Secreted monocytic miR-150 enhances targeted endothelial cell migration," *Mol. Cell*, 39:133-144, 2010.
Zomer et al., "Exosomes: Fit to Deliver Small RNA," *Communicative & Integrative Biology*, 3:447-450, 2010.
Lobb, R.J. et al. "Optimized Exosome Isolation Protocol for Cell Culture Supernatant and Human Plasma," Journal of Extracellular Vesicles, Jul. 17, 2015, vol. 4, No. 27031, pp. 1-11.
Pachler, K. et al., "A Good Manufacturing Practice-Grade Standard Protocol for Exclusively Human Mesenchymal Stroma• Cell-Derived Extracellular Vesicles," Cytotherapy, Apr. 1, 2017, vol. 19, No. 4, pp. 458-472.
PCT International Search Report and Written Opinion, PCT Application No. PCT/US2018/052074, dated Dec. 4, 2018, 14 pages.
Office Action issued in Chinese Application No. 201680033436.8, dated Dec. 31, 2019, and English language translation thereof.
Office Action issued in Japanese Application No. 2017-564011, dated Jun. 30, 2020, and English language machine translation thereof.
Takahashi et al., "In vivo fate of exogenously-administered exosomes," *Drug Delivery System*, 29-2:116-124, 2014 (Japanese with English abstract).

* cited by examiner

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
guuggagcug auggcguagt t                                                21

<210> SEQ ID NO 2
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 2
ccgggttgga gctgatggcg tagttctcga gctacgccat cagctccaac tttttt        57

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
acttgtggta gttggagcag a                                                21

<210> SEQ ID NO 4
<211> LENGTH: 21
<212> TYPE: DNA
<213> ORGANISM: Artificial Sequence
<220> FEATURE:
```

```
<223> OTHER INFORMATION: Synthetic oligonucleotide

<400> SEQUENCE: 4
ttggatcata ttcgtccaca a                                              21

<210> SEQ ID NO 5
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 5
attgtgaatg ttggtgt                                                   17

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
gaaggtctca actgaaatt                                                 19

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gtaacccgtt gaaccccatt                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ccatccaatc ggtagtagcg                                                20
```

USE OF EXOSOMES FOR THE TREATMENT OF DISEASE

The present application is a continuation of U.S. application Ser. No. 15/735,186, filed Dec. 10, 2017, which is a national phase application under 35 U.S.C. § 371 of International Application No. PCT/US2016/037018, filed Jun. 10, 2016, which claims the priority benefit of U.S. provisional application No. 62/173,838, filed Jun. 10, 2015, the entire contents of each of which are incorporated herein by reference.

INCORPORATION OF SEQUENCE LISTING

The sequence listing that is contained in the file named "UTSCP1216USC1.txt", which is 2 KB (as measured in Microsoft Windows®) and was created on Nov. 28, 2018, is filed herewith by electronic submission and is incorporated by reference herein.

BACKGROUND OF THE INVENTION

1. Field of the Invention

The present invention relates generally to the field of medicine and oncology. More particularly, it concerns the use of exosomes in methods of treatment.

2. Description of Related Art

Exosomes are small (40-150 nm) membrane vesicles with a lipid bilayer of endosomal origin that are released by all cells of the body (Kowal et al., 2014; El-Andaloussi et al., 2013; Thery et al., 2002). Exosomes contain proteins, lipids, mRNA, microRNAs (miRNAs) and genomic DNA (Valadi et al., 2007; Peinado et al., 2012; Luga et al., 2012; Kahlert et al., 2014). Unlike liposomes and other synthetic drug nanoparticle carriers, exosomes contain many transmembrane and membrane anchored proteins that likely enhance endocytosis and/or direct fusion with the plasma membrane of the recipient cells, thus enhancing cargo delivery (Marcus et al., 2013; van den Boom et al., 2013; Johnsen et al., 2014). The exosomes natural plasma membrane-like phospholipid composition (including phosphatidylserine on the cytosolic side and cholesterol) and membrane-associated protein composition may also offer superior stability in systemic circulation when compared to synthetic nanoparticles (such as liposomes) by reducing clearance from the circulation (in part via their lack of interaction with opsonins and coagulation and complement factors recognized by macrophage for phagocytosis) and minimizing immunogenic response (Clayton et al., 2003; van der Meel et al., 2014; Gomes-da-Silva et al., 2012). These features would likely also minimize cytotoxic effects observed when synthetic nanoparticles were used in vivo (Simoes et al., 2005). Finally, the endosomal and intercellular vesicle trafficking machinery involved in the generation of exosomes may also be used in exosomes uptake by recipient cells, possibly enhancing cargo release (and incorporation into the RNAi gene silencing machinery) thereby augmenting efficacy of any therapeutic agent (e.g., gene targeting). Recent studies evaluated the efficacy of exosomes as RNAi carriers for therapy, and indicated that systemic injection of exosomes enabled the delivery of siRNA into the brain, leading to robust downregulation of the target genes (Cooper et al., 2014; Alvarez-Erviti et al., 2011). Furthermore, human plasma-derived exosomes were also reported to enable RNAi delivery to recipient cells (Wahlgren et al., 2012), supporting their potential therapeutic utility in RNAi delivery for gene expression modification in target cells.

Single nucleotide variations in KRAS ($Kras^{G12D/R/V}$ mutations) are found in as many as 96% of pancreas tumors (Chang et al., 2014), and Kras mutations are considered early neoplastic events that drive and maintain pancreas malignant transformation (Ying et al., 2012; Collin et al., 2012; Collins et al., 2012; Smakman et al., 2005). RNAi-based targeting of Kras expression and downstream signaling using nanoparticles was recently reported to reduce tumor burden in lung and colorectal cancer models (Pecot et al., 2014; Yuan et al., 2014; Xue et al., 2014). Unlike efforts focusing on specific targeting of oncogenic Kras, these approaches may induce cytotoxic effects that would require careful dosage and monitoring. Specific targeting of oncogenic Kras has been limited to delivery via electroporation (Rejiba et al., 2007) or biopolymeric implants (Zorde Khvalevsky et al., 2013) in xenograph models of pancreas cancer. Improved approaches are needed to deliver therapeutic or diagnostic agents.

SUMMARY OF THE INVENTION

Provided herein are methods and drugs that use engineered liposomes and exosomes as delivery systems for treatment of cancer.

In one embodiment, pharmaceutical compositions are provided that comprise a lipid-based nanoparticle and an excipient, wherein the lipid-based nanoparticle comprises CD47 on its surface and wherein the lipid-based nanoparticle comprises a therapeutic agent. In some aspects, the lipid-based nanoparticle is a liposome or an exosomes. In certain aspects, the exosomes are isolated from a cell over expressing CD47. In some aspects, the exosomes are isolated from a patient in need of treatment. In some aspects, the exosomes are isolated from fibroblasts. In some aspects, the liposome is a single lamellar liposome. In some aspects, the liposome is a multilamellar liposome.

In various aspects, the therapeutic agent is a therapeutic protein, an antibody (e.g., a full-length antibody, a monoclonal antibody, an scFv, a Fab fragment, a F(ab')2, a diabody, a triabody, or a minibody), an inhibitory RNA, or a small molecule drug. In some aspects, the therapeutic protein is a protein whose loss or inactivation is known to relate to a disease to be treated, such as, for example, a tumor suppressor, a kinase, a phosphatase, or a transcription factor. In some aspects, the antibody binds an intracellular antigen. Such an intracellular antigen may be a protein whose activity is required for cell proliferation and/or survival, such as an oncogene. In some cases, the antibody prevents the function of the antigen. In some cases, the antibody disrupts a protein-protein interaction. In some aspects, the inhibitory RNA is a siRNA, shRNA, miRNA, or pre-miRNA. In various aspects, the inhibitory RNA prevents the expression of a protein whose activity is necessary for the maintenance of a certain disease state, such as, for example, an oncogene. In cases where the oncogene is a mutated form of a gene, then the inhibitory RNA may preferentially prevent the expression of the mutant oncogene and not the wild-type protein. In some aspects, the small molecule drug is an imaging agent. In some aspects, the small molecule drug is a chemotherapeutic agent.

In some aspects, the composition is formulated for parenteral administration, such as, for example, intravenous, intramuscular, sub-cutaneous, or intraperitoneal injection.

In some aspects, the composition comprises an antimicrobial agent. The antimicrobial agent may be benzalkonium chloride, benzethonium chloride, benzyl alcohol, bronopol, centrimide, cetylpyridinium chloride, chlorhexidine, chlorobutanol, chlorocresol, chloroxylenol, cresol, ethyl alcohol, glycerin, exetidine, imidurea, phenol, phenoxyethanol, phenylethl alcohol, phenlymercuric nitrate, propylene glycol, or thimerosal.

In some aspects, a single lipid-based nanoparticle comprises more than one agent, such as a therapeutic agent and a diagnostic agent, more than one therapeutic agents, or more than one diagnostic agents.

In one embodiment, methods are provided for treating a disease in a patient in need thereof comprising administering a composition of any of the present embodiments to the patient, thereby treating the disease in the patient. In some aspects, the disease is a cancer. In some aspects, the patient is a human. In some aspects, the patient had previously had a tumor surgically removed.

In some aspects, the therapeutic agent is an inhibitory RNA targeting an oncogene. In certain aspects, the inhibitory RNA targets Kras$^{G12D}$. In some aspects, the therapeutic agent is a tumor suppressor protein.

In some aspects, the method further comprises administering at least a second therapy to the patient. In various aspects, the second therapy comprises a surgical therapy, chemotherapy, radiation therapy, cryotherapy, hormonal therapy, or immunotherapy.

In one embodiment, methods are provided for treating a disease in a patient in need thereof comprising electroporating liposomes or exosomes with a therapeutic agent (e.g., a monoclonal antibody) and provided the electroporated liposomes exosomes to the patient, thereby treating the disease in the patient. In some aspects, the liposomes or exosomes comprise CD47 on their surface. In some aspects, the disease is a cancer. In some aspects, the monoclonal antibody specifically or selectively binds an intracellular antigen.

In one embodiment, methods are provided for administering a therapeutic protein to a patient in need thereof comprising transfecting exosomes with a nucleic acid (e.g., a DNA or an RNA) encoding a therapeutic protein (e.g., a monoclonal antibody or an antigen-binding fragment thereof), incubating the transfected exosomes under conditions to allow for expression of the therapeutic protein within the exosomes, and providing the incubated exosomes to the patient, thereby administering the therapeutic protein to the patient.

In one embodiment, methods are provided for administering a therapeutic antibody to a cell comprising contacting the cell with a lipid-based nanoparticle comprising the antibody, wherein the antibody specifically or selectively binds an intracellular antigen. In some cases, the cell is comprised in a patient and the method comprises administering the lipid-based nanoparticle to the patient.

In one embodiment, methods are provided for treating a cancer in a patient comprising administering a therapeutically effective amount of a lipid-based nanoparticle to the patient, wherein the nanoparticle comprises an inhibitory RNA that specifically or selectively targets mutant Kras (e.g., Kras$^{G12D}$). In some aspects, the cancer is a lung cancer, colorectal cancer, or pancreas cancer. In some aspects, the cancer is pancreatic ductal adenocarcinoma. In some aspects, the lipid-based nanoparticle is a liposome or an exosomes. In certain aspects, the exosomes are derived from the patient's own cells. In some aspects, the lipid-based nanoparticle comprises CD47 on its surface. In some aspects, the inhibitory RNA is an siRNA or an shRNA. In some aspects, the inhibitory RNA sequence is designed to contain the specific G to A nucleotide deviation in the targeting region (e.g., as found in SEQ ID NO: 1) to promote the specific targeting of Kras$^{G12D}$ mRNA. In some aspects, the inhibitory RNA comprises a targeting region having a sequence according to SEQ ID NO: 2.

In one embodiment, a composition is provided comprising a lipid-based nanoparticle and an excipient for use in the treatment of a disease in a patient. In some aspects, the lipid-based nanoparticle comprises CD47 on its surface. In some aspects, the lipid-based nanoparticle comprises a therapeutic agent. In some aspects, the disease may be a cancer. In some aspects, the therapeutic agent is an inhibitory RNA targeting an oncogene. In some aspects, the inhibitory RNA targets Kras$^{G12D}$. In some aspects, the therapeutic agent is a tumor suppressor protein. In some aspects, the composition further comprises at least a second therapy. In some aspects, the second therapy comprises a surgical therapy, chemotherapy, radiation therapy, cryotherapy, hormonal therapy, or immunotherapy. In some aspects, the patient is a human.

In some aspects, the composition is formulated for parenteral administration, such as, for example, intravenous, intramuscular, sub-cutaneous, or intraperitoneal injection.

In some aspects, the composition comprises an antimicrobial agent. The antimicrobial agent may be benzalkonium chloride, benzethonium chloride, benzyl alcohol, bronopol, centrimide, cetylpyridinium chloride, chlorhexidine, chlorobutanol, chlorocresol, chloroxylenol, cresol, ethyl alcohol, glycerin, exetidine, imidurea, phenol, phenoxyethanol, phenylethl alcohol, phenlymercuric nitrate, propylene glycol, or thimerosal.

In one embodiment, the use of a lipid-based nanoparticle in the manufacture of a medicament for the treatment of disease is provided. In some aspects, the lipid-based nanoparticle comprises CD47 on its surface. In some aspects, the lipid-based nanoparticle comprises a therapeutic agent. In some aspects, the disease is a cancer. In some aspects, the therapeutic agent is an inhibitory RNA targeting an oncogene. In some aspects, the inhibitory RNA targets Kras$^{G12D}$. In some aspects, the therapeutic agent is a tumor suppressor protein.

In some aspects, the medicament is formulated for parenteral administration, such as, for example, intravenous, intramuscular, sub-cutaneous, or intraperitoneal injection.

In some aspects, the medicament comprises an antimicrobial agent. The antimicrobial agent may be benzalkonium chloride, benzethonium chloride, benzyl alcohol, bronopol, centrimide, cetylpyridinium chloride, chlorhexidine, chlorobutanol, chlorocresol, chloroxylenol, cresol, ethyl alcohol, glycerin, exetidine, imidurea, phenol, phenoxyethanol, phenylethl alcohol, phenlymercuric nitrate, propylene glycol, or thimerosal.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Quantification of confocal micrographs of Panc-1 cells stained with SYTOX® Green nuclear labeling and visualization of internalized exosomes (exos) and liposomes (lipos) containing siRNA tagged with Alexa Fluor® 647. Panc-1 cells were pre-incubated with and without proteinase K or trypsin prior to exposure to Alexa fluor 647 tagged siRNA containing exos or lipos. Unpaired two-tailed student t-test was used to determine the statistical significance between the groups. (FIGS. 1B-C) Real time PCR analyses of $KRAS^{G12D}$ (FIG. 1B) or wild-type KRAS (FIG. 1C) transcript levels in Panc-1 cells treated for 3 hours with $siKras^{G12D}$ or $shKras^{G12D}$ containing exos or lipos, siScrb1 or shScrb1 containing exos or lipos, or non-electroporated (empty cargo, control exos) exos. The fold change is represented relative to the expression of untreated Panc-1 cells (Control), which was arbitrarily set to 1. Unpaired two tailed student t-test was used to determine statistical significance when compared to untreated Panc-1 cells transcript levels. (FIG. 1D) Western blotting of lysates from untreated Panc-1 (Control) lysates and lysates from Panc-1 cells treated with $siKras^{G12D}$ or $shKras^{G12D}$ exos for phosphorylated AKT (p-AKT), phosphorylated ERK (p-ERK) and Actin (loading control). (FIG. 1E) Relative number of Panc-1 cells over time following exposure to the listed treatments. (FIG. 1F) Quantification of immunostaining micrographs performed for the apoptosis marker TUNEL in Panc-1 cells exposed to the listed treatments. Puromycin was used as positive control. (0) indicates no cells were detected positive for TUNEL. Control: untreated, Control exos: non-electroporated (no siRNA cargo) exos. Unpaired two-tailed student t-test was used to determine the statistical significance between the groups. The mean is depicted +/−SEM. Unless stated otherwise, one-way ANOVA was used to determine statistical significance. * $p<0.01$, ** $p<0.001$, ns: not significant.

(FIG. 2A) Relative radiance of bioluminescent Panc-1 orthotopic tumors over time. PBS: n=7, Control exos: n=6, $siKras^{G12D}$ lipos: n=3, $shKras^{G12D}$ lipos: n=3, $siKras^{G12D}$ exos: n=7, $shKras^{G12D}$ exos: n=7. Statistical test results are shown comparing treatment groups to the PBS control group at day 42 post cancer cell injection, with the exception of the $siKras^{G12D}$ exos group, which was compared to the PBS group at experimental endpoint (day 28 post cancer cell injection). Top pair of lines are PBS and Control Exos; middle pair of lines are the lipos; bottom pair of lines are the exos. (FIG. 2B) Relative radiance of bioluminescent BxPC3 orthotopic tumors over time. PBS: n=3, Control exos: n=3, $siKras^{G12D}$ exos: n=3, $shKras^{G12D}$ exos: n=3. Statistical test results are shown comparing treatment groups to PBS control group at day 77 post cancer cell injection. (FIG. 2C) Relative radiance of bioluminescent Panc-1 orthotopic tumors over time. Experimental groups started with PBS: n=7, Control exos: n=6, $siKras^{G12D}$ exos: n=7, $shKras^{G12D}$ exos: n=7, and progressively declined as mice were moribund and euthanized (PBS and control exos groups). Small foci of cancer cells were seen in the $shKras^{G12D}$ exos treated pancreas, however the vast majority of the pancreas was histologically unremarkable. Top pair of lines are PBS and Control Exos; bottom pair of lines are the $si/shKras^{G12D}$ exos. (FIG. 2D) Comparative analysis of measured radiance of bioluminescence at day 77 post cancer cell injection of orthotopic Panc-1 tumors. PBS: n=7, Control exos: n=6, $shKras^{G12D}$ exos: n=7. Unpaired two-tailed student t-test was used to determine the statistical significance between the groups. (FIG. 2E) Quantification of p-ERK immunolabeling (scale bar: 50 µm) and percent p-ERK staining in pancreas tumors in the experimental groups. n=6. Note that the quantification was performed on measurably smaller tumor areas in the $shKras^{G12D}$ exos treated group. Unpaired two-tailed student t-test was used to determine the statistical significance between both groups. (FIG. 2F) Tumor burden (relative mass of pancreas to body mass) in the indicated experimental groups upon euthanasia (PBS: Day 62-130, Control exos: Day 30-132, $shKras^{G12D}$ exos: Day 200). Unpaired two-tailed student t-test was used to determine the statistical significance between the groups. (FIG. 2G) Kaplan-Meier curve comparison in the survival of mice in the indicated experimental groups and statistical differences were evaluated using the log rank Mantel-Cox test, PBS: n=7, Control exos: n=6, $shKras^{G12D}$ exos: n=7. The mean is depicted +/−SEM. Unless stated otherwise, one-way ANOVA was used to determine statistical significance. * $p<0.05$,  $p<0.01$, * $p<0.001$, **** $p<0.0001$, ns: not significant.

(FIG. 3A) Schematic representation of tumor progression timeline with experimental treatment points in $Ptf1a^{cre/+}$;$LSL-Kras^{G12D/+}$;$Tgfbr2^{flox/flox}$ (PKT) mice. Treatment with BJ fibroblast exosomes containing $Kras^{G12D}$ RNAi was started on day 33, and subsequently continued every other day until the mice reached experimental endpoint or became moribund and required euthanasia. The control group was treated with the same concentration of non-electroporated BJ exosomes (Control exos). (FIG. 3B) Kaplan-Meier curve comparison of the survival of mice in the indicated experimental groups and statistical differences were evaluated using the log rank Mantel-Cox test. n=5 in each group. (FIG. 3C) Tumor burden (relative mass of pancreas to body mass) in the indicated experimental groups at 44 days of age. n=3 in each group. (FIG. 3D) Quantification of the relative percentages determined from micrographs of H&E stained tumors from 44 day-old PKT mice treated with siKras$^{G12D}$ containing exos or non-electroporated control exos, n=3. One-way ANOVA was used for statistical comparison. (FIGS. 3E-F) Kaplan-Meier curve comparison (FIG. 3E) of the survival of mice in the indicated experimental groups (exosomes from PKT derived fibroblasts, n=5 in each group; left line is Control Exos; right line is siKras$^{G12D}$ exos), and (FIG. 3F) tumor burden, n=5. Log rank Mantel-Cox test was performed for statistical analysis of the Kaplan-Meier curve comparison. (FIG. 3G) Quantification of micrographs of Masson Trichrome staining (MTS) and immunolabeling for apoptosis marker TUNEL, proliferation marker Ki-67, and phosphorylated-ERK of from 44 day-old PKT pancreas tumors in the indicated experimental groups. n=3. Data are represented as mean±SEM. Unless stated otherwise, unpaired two tailed student t-test was used to determine statistical significance.  $p<0.01$, ** $p<0.0001$.

(FIG. 4A) Schematic representation of electroporation of RNAi into exosomes. The RNAi in the representation is tagged with Alexa Fluor® 647. (FIG. 4B) Exosomes numbers and size distribution-using NanoSight. (FIGS. 4C-D) Transmission electron micrograph of exosomes purified from BJ fibroblasts (FIG. 4C) and stained for CD9 by immunogold (FIG. 4D). (FIG. 4E) Northern blot of sucrose gradient of BJ fibroblast exosomes containing Alexa Fluor® 647-tagged siRNA. The detection of the fluorescence of Alexa Fluor® 647 fluorophore is depicted in the blot. (FIG. 4F) Real time PCR analyses of KRAS$^{G12D}$ transcript levels in Panc-1 cells treated for 3 hours with siKras$^{G12D}$ or shKras$^{G12D}$ lipos, siScrb1 or shScrb1 lipos, with increasing concentrations of lipos (1×, 10×, 100×) as well as increased treatment time of Panc-1 cells (24 hours). The fold change is represented relative to the expression of untreated Panc-1 cells (control), which was arbitrarily set to 1. Unpaired two-tailed student t-test was used to determine statistical significance when compared to untreated Panc-1 cell transcript levels. (FIG. 4G) Real time PCR analyses of KRA$^{G12D}$ transcript levels in Panc-1 cells treated for 3 hours with siKras$^{G12D}$ or shKras$^{G12D}$ exos as shown in FIG. 1B, and with increased concentration of exos (~700 exos per cells instead of ~400 exos per cells). Unpaired two-tailed student t-test was used to determine statistical significance when compared to untreated Panc-1 cell transcript levels. (FIG. 4H) Real time PCR analyses of wild-type KRAS transcript levels in BxPC-3 cells treated for 3 hours with siKras$^{G12D}$ or shKras$^{G12D}$ exos. Unpaired two-tailed student t-test was used to determine statistical significance when compared to untreated BxPC3 cells transcript levels. (FIG. 4I) Relative number of BXPC-3 cells over time following exposure to the listed treatments. Unpaired two tailed student t-test was used at the final time point * $p<0.05$,  $p<0.01$, * $p<0.001$, **** $p<0.0001$, ns: not significant.

(FIG. 5A) Flow cytometry analyses of exosomes isolated from the serum of siKras$^{G12D}$ exos treated mice 24 hours post i.p. injection. Labeled exosomes were detected using the Alexa Fluor® 647 tagged RNAi they contain following binding to 0.4 μm beads. (FIG. 5B) Flow cytometry analyses and quantification of the percentage of Alexa Fluor® 647$^+$/CD11b$^+$ macrophages in the blood of mice 12 hours following i.p. injection of Alexa fluor 647 tagged RNAi containing exos or lipos. (FIG. 5C) Quantification of percent p-AKT stained area in micrographs of pancreas tumors immunolabeled for phosphorylated AKT (p-AKT). n=6. Note that the quantification was performed on relatively smaller tumor areas in the shKras$^{G12D}$ exos treated group. (FIG. 5D) Kaplan-Meier curve comparison in the survival of mice with BxPC-3 orthotopic tumors in the indicated experimental groups, PBS: n=3, Control exos: n=3, shKras$^{G12D}$ exos: n=3, siKras$^{G12D}$ exos: n=3 (Log rank (Mantel-Cox) test was used for this analysis). Data are represented as mean±SEM. Unless otherwise noted, unpaired two-tailed student t-test was used to determine statistical significance. * $p<0.05$,  $p<0.01$, * $p<0.001$, **** $p<0.0001$, ns: not significant.

(FIG. 6A) Comparative analysis of measured radiance of bioluminescence at day 77. PBS: n=7, Control exos: n=6, shKras$^{G12D}$ exos: n=7. Unpaired two-tailed student t-test at day 77 was used to determine statistical significance * $p<0.05$,  $p<0.01$, * $p<0.001$, **** $p<0.0001$, ns: not significant. (FIG. 6B) Spider plot depicting individual tumors. PBS: n=7, Control exos: n=6, shKras$^{G12D}$ exos: n=7.

(FIG. 7A) Tumor burden (relative mass of pancreas to body mass) in the experimental end point (control exos: median survival of 43 days, siKras$^{G12D}$ exos: median survival of 60 days). n=5 in each group. (FIGS. 7B-C) Quantification of relative percentages of histological phenotypes in micrographs of H&E stained tumors of PKT mice at the indicated experimental end points and treated with (FIG. 7B) BJ fibroblast and (FIG. 7C) PKT fibroblast derived siKras$^{G12D}$ exos or non-electroporated exos (Control exos). n=5. Two-way ANOVA was used for statistical comparison. (FIG. 7D) Quantification of micrographs of tumors immunolabeled for phosphorylated AKT from 44 day-old PKT mice in the indicated experimental groups. Data are represented as mean±SEM. Unless stated otherwise, unpaired two-tailed student t-test was used to determine statistical significance.  $p<0.01$, ** $p<0.0001$.

(FIG. 8A) Top plots show the % of CD11b positive cells from the total live cell population. Bottom plots show the % of A647 and CD11b doubly positive cells from the total live cell population. (FIG. 8B) Quantification of FACS plots provided in FIG. 8A.

(FIG. 9A) Exosomes isolated from BJ fibroblasts. Top plots show staining with secondary antibody only which the bottom plots show staining for either CD63 or CD47. (FIG. 9B) Liposomes (100 nm) stained with secondary antibody only or with antibodies for CD63 or CD47. (FIG. 9C) Expression of CD47 by exosomes isolated from three different cell lines by two different methods.

DESCRIPTION OF ILLUSTRATIVE EMBODIMENTS

Figure 1A:
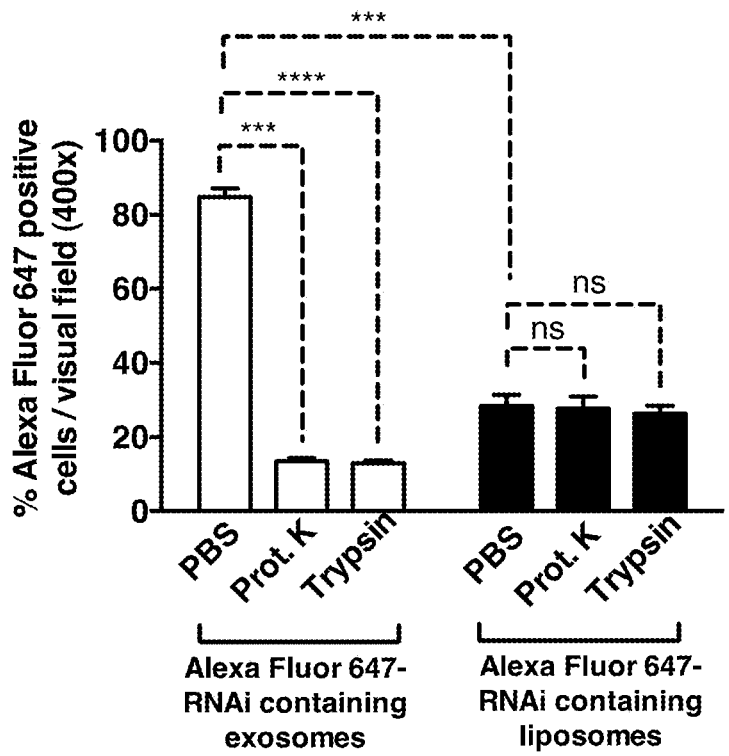
FIGS. 1A-F. Targeting of $Kras^{G12D}$ mediated by siRNA/shRNA packaged in exosomes induces cancer cell death.

Despite current standard of care, pancreatic ductal adenocarcinoma (PDAC) has a median survival of six months for metastatic patients with only 6.7% surviving after five years (Siegel et al., 2014; Howlader et al., 2013). Therefore, PDAC is in urgent need of effective new therapies. Genetic analyses of PDAC show that mutations in the RAS family of small GTPases (KrasG12/D/R/V) occur in 70%-96% of patients (Biankin et al., 2012; Hruban et al., 1993; Almoguera et al., 1988; Chang et al., 2014) and are key drivers of tumor growth and metastasis (Ying et al., 2012; Hingorani et al., 2005; Collins et al., 2012a; Collins et al., 2012b; Eser et al., 2014). Genetic manipulations in mice have shown that dampening oncogenic KRAS reverses tumor progression (Ying et al., 2012; Collins et al., 2012a; Collins et al., 2012b; Smakman et al., 2005). Oncogenic KRAS signaling and increased RAS activity have emerged as initiating drivers of pancreas neoplasia (Collins et al., 2012a; Eser et al., 2014; Ji et al., 2009); however, RAS remains an intractable target and a therapy challenge (Gysin et al., 2011). Herein, exosomes derived from normal fibroblasts were engineered to carry RNA interference (RNAi) payloads to target oncogenic $KRAS^{G12D}$. Exosomes containing TT-linked siRNA or shRNA against $Kras^{G12D}$ efficiently entered cancer cells and specifically suppressed oncogenic Ras, attenuating ERK activation, inhibiting proliferation, and inducing cancer cell apoptosis. Systemic delivery of exosomes with $Kras^{G12D}$ targeting cargo show robust pancreas localization and suppression of pre-established orthotopic human pancreas tumors as well as tumors in genetically engineered mouse models (GEMMs) of pancreas cancer, together with an improvement in survival, when compared to liposomes containing si/shRNA and exosomes with scrambled RNAi constructs. Tumors of mice treated with si/shRNA containing exosomes displayed significant decreases in downstream RAS signal mediators and improved histopathological findings with normal pancreas histology. Human fibroblast derived exosomes show similar efficacy as mouse fibroblast derived exosomes in PDAC GEMM, thus suggesting that patient-specific exosomes may not be required to allow for efficient RNAi delivery while minimizing potential toxic side effects. Such a strategy offers a novel and efficient means to suppress oncogenic gene expression and downstream signaling with minimal off-target effects.

CD47 (Integrin Associated Protein) is a transmembrane protein that is expressed on most tissues and cells. CD47 is a ligand for Signal Regulatory Protein Alpha (SIRP-α), which is expressed on phagocytic cells such as macrophages and dendritic cells. Activated CD47-SIRP-α initiates a signal transduction cascade that inhibits phagocytosis. Injection of a monoclonal antibody against CD47 into mice prior to exosomes injection or treatment of exosomes with a CD47 neutralizing antibody prior to injection both block CD47 and permit the engulfment of exosomes by macrophages or monocytes. Thus, expression of CD47 on the surface of exosomes prevents phagocytosis by macrophages.

I. LIPID-BASED NANOPARTICLES

In some embodiments, a lipid-based nanoparticle is a liposomes, an exosomes, lipid preparations, or another lipid-based nanoparticle, such as a lipid-based vesicle (e.g., a DOTAP:cholesterol vesicle). Lipid-based nanoparticles may be positively charged, negatively charged or neutral.

A. Liposomes

A "liposome" is a generic term encompassing a variety of single and multilamellar lipid vehicles formed by the generation of enclosed lipid bilayers or aggregates. Liposomes may be characterized as having vesicular structures with a bilayer membrane, generally comprising a phospholipid, and an inner medium that generally comprises an aqueous composition. Liposomes provided herein include unilamellar liposomes, multilamellar liposomes, and multivesicular liposomes. Liposomes provided herein may be positively charged, negatively charged, or neutrally charged. In certain embodiments, the liposomes are neutral in charge.

A multilamellar liposome has multiple lipid layers separated by aqueous medium. Such liposomes form spontaneously when lipids comprising phospholipids are suspended in an excess of aqueous solution. The lipid components undergo self-rearrangement before the formation of closed structures and entrap water and dissolved solutes between the lipid bilayers. Lipophilic molecules or molecules with lipophilic regions may also dissolve in or associate with the lipid bilayer.

In specific aspects, a polypeptide, a nucleic acid, or a small molecule drug may be, for example, encapsulated in the aqueous interior of a liposome, interspersed within the lipid bilayer of a liposome, attached to a liposome via a linking molecule that is associated with both the liposome and the polypeptide/nucleic acid, entrapped in a liposome, complexed with a liposome, or the like.

A liposome used according to the present embodiments can be made by different methods, as would be known to one of ordinary skill in the art. For example, a phospholipid, such as for example the neutral phospholipid dioleoylphosphatidylcholine (DOPC), is dissolved in tert-butanol. The lipid(s) is then mixed with a polypeptide, nucleic acid, and/or other component(s). Tween 20 is added to the lipid mixture such that Tween 20 is about 5% of the composition's weight. Excess tert-butanol is added to this mixture such that the volume of tert-butanol is at least 95%. The mixture is vortexed, frozen in a dry ice/acetone bath and lyophilized overnight. The lyophilized preparation is stored at $-20°$ C. and can be used up to three months. When required the lyophilized liposomes are reconstituted in 0.9% saline.

Alternatively, a liposome can be prepared by mixing lipids in a solvent in a container, e.g., a glass, pear-shaped flask. The container should have a volume ten-times greater than the volume of the expected suspension of liposomes. Using a rotary evaporator, the solvent is removed at approximately $40°$ C. under negative pressure. The solvent normally is removed within about 5 min to 2 h, depending on the desired volume of the liposomes. The composition can be dried further in a desiccator under vacuum. The dried lipids generally are discarded after about 1 week because of a tendency to deteriorate with time.

Dried lipids can be hydrated at approximately 25-50 mM phospholipid in sterile, pyrogen-free water by shaking until all the lipid film is resuspended. The aqueous liposomes can be then separated into aliquots, each placed in a vial, lyophilized and sealed under vacuum.

The dried lipids or lyophilized liposomes prepared as described above may be dehydrated and reconstituted in a solution of a protein or peptide and diluted to an appropriate concentration with a suitable solvent, e.g., DPBS. The mixture is then vigorously shaken in a vortex mixer. Unencapsulated additional materials, such as agents including but not limited to hormones, drugs, nucleic acid constructs and the like, are removed by centrifugation at 29,000×g and the liposomal pellets washed. The washed liposomes are resuspended at an appropriate total phospholipid concentration, e.g., about 50-200 mM. The amount of additional material or active agent encapsulated can be determined in accordance with standard methods. After determination of the amount of additional material or active agent encapsulated in the liposome preparation, the liposomes may be diluted to appropriate concentrations and stored at 4° C. until use. A pharmaceutical composition comprising the liposomes will usually include a sterile, pharmaceutically acceptable carrier or diluent, such as water or saline solution.

Additional liposomes which may be useful with the present embodiments include cationic liposomes, for example, as described in WO02/100435A1, U.S. Pat. No. 5,962,016, U.S. Application 2004/0208921, WO03/015757A1, WO04029213A2, U.S. Pat. Nos. 5,030,453, and 6,680,068, all of which are hereby incorporated by reference in their entirety without disclaimer.

In preparing such liposomes, any protocol described herein, or as would be known to one of ordinary skill in the art may be used. Additional non-limiting examples of preparing liposomes are described in U.S. Pat. Nos. 4,728,578, 4,728,575, 4,737,323, 4,533,254, 4,162,282, 4,310,505, and 4,921,706; International Applications PCT/US85/01161 and PCT/US89/05040, each incorporated herein by reference.

In certain embodiments, the lipid based nanoparticle is a neutral liposome (e.g., a DOPC liposome). "Neutral liposomes" or "non-charged liposomes", as used herein, are defined as liposomes having one or more lipid components that yield an essentially-neutral, net charge (substantially non-charged). By "essentially neutral" or "essentially non-charged", it is meant that few, if any, lipid components within a given population (e.g., a population of liposomes) include a charge that is not canceled by an opposite charge of another component (i.e., fewer than 10% of components include a non-canceled charge, more preferably fewer than 5%, and most preferably fewer than 1%). In certain embodiments, neutral liposomes may include mostly lipids and/or phospholipids that are themselves neutral under physiological conditions (i.e., at about pH 7).

Liposomes and/or lipid-based nanoparticles of the present embodiments may comprise a phospholipid. In certain embodiments, a single kind of phospholipid may be used in the creation of liposomes (e.g., a neutral phospholipid, such as DOPC, may be used to generate neutral liposomes). In other embodiments, more than one kind of phospholipid may be used to create liposomes. Phospholipids may be from natural or synthetic sources. Phospholipids include, for example, phosphatidylcholines, phosphatidylglycerols, and phosphatidylethanolamines; because phosphatidylethanolamines and phosphatidyl cholines are non-charged under physiological conditions (i.e., at about pH 7), these compounds may be particularly useful for generating neutral liposomes. In certain embodiments, the phospholipid DOPC is used to produce non-charged liposomes. In certain embodiments, a lipid that is not a phospholipid (e.g., a cholesterol) may be used Phospholipids include glycerophospholipids and certain sphingolipids. Phospholipids include, but are not limited to, dioleoylphosphatidylycholine ("DOPC"), egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), distearoyl sphingomyelin ("DSSP"), distearoylphophatidylethanolamine ("DSPE"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), dimyristoyl phosphatidylserine ("DMPS"), dipalmitoyl phosphatidylserine ("DPPS"), brain phosphatidylserine ("BPS"), brain sphingomyelin ("BSP"), dipalmitoyl sphingomyelin ("DPSP"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), dioleoylphosphatidylethanolamine ("DOPE"), palmitoyloeoyl phosphatidylcholine ("POPC"), palmitoyloeoyl phosphatidylethanolamine ("POPE"), lysophosphatidylcholine, lysophosphatidylethanolamine, and dilinoleoylphosphatidylcholine.

B. Exosomes

The terms "microvesicle" and "exosomes," as used herein, refer to a membranous particle having a diameter (or largest dimension where the particles is not spheroid) of between about 10 nm to about 5000 nm, more typically between 30 nm and 1000 nm, and most typically between about 50 nm and 750 nm, wherein at least part of the membrane of the exosomes is directly obtained from a cell. Most commonly, exosomes will have a size (average diameter) that is up to 5% of the size of the donor cell. Therefore, especially contemplated exosomes include those that are shed from a cell.

Exosomes may be detected in or isolated from any suitable sample type, such as, for example, body fluids. As used herein, the term "isolated" refers to separation out of its natural environment and is meant to include at least partial purification and may include substantial purification. As used herein, the term "sample" refers to any sample suitable for the methods provided by the present invention. The sample may be any sample that includes exosomes suitable for detection or isolation. Sources of samples include blood, bone marrow, pleural fluid, peritoneal fluid, cerebrospinal fluid, urine, saliva, amniotic fluid, malignant ascites, broncho-alveolar lavage fluid, synovial fluid, breast milk, sweat, tears, joint fluid, and bronchial washes. In one aspect, the sample is a blood sample, including, for example, whole blood or any fraction or component thereof. A blood sample suitable for use with the present invention may be extracted from any source known that includes blood cells or components thereof, such as venous, arterial, peripheral, tissue, cord, and the like. For example, a sample may be obtained and processed using well-known and routine clinical methods (e.g., procedures for drawing and processing whole blood). In one aspect, an exemplary sample may be peripheral blood drawn from a subject with cancer.

Exosomes may also be isolated from tissue samples, such as surgical samples, biopsy samples, tissues, feces, and cultured cells. When isolating exosomes from tissue sources it may be necessary to homogenize the tissue in order to obtain a single cell suspension followed by lysis of the cells to release the exosomes. When isolating exosomes from tissue samples it is important to select homogenization and lysis procedures that do not result in disruption of the exosomes. Exosomes contemplated herein are preferably isolated from body fluid in a physiologically acceptable solution, for example, buffered saline, growth medium, various aqueous medium, etc.

Exosomes may be isolated from freshly collected samples or from samples that have been stored frozen or refrigerated. In some embodiments, exosomes may be isolated from cell culture medium. Although not necessary, higher purity exosomes may be obtained if fluid samples are clarified before precipitation with a volume-excluding polymer, to remove any debris from the sample. Methods of clarification include centrifugation, ultracentrifugation, filtration, or ultrafiltration. Most typically, exosomes can be isolated by numerous methods well-known in the art. One preferred method is differential centrifugation from body fluids or cell culture supernatants. Exemplary methods for isolation of exosomes are described in (Losche et al., 2004; Mesri and Altieri, 1998; Morel et al., 2004). Alternatively, exosomes may also be isolated via flow cytometry as described in (Combes et al., 1997).

One accepted protocol for isolation of exosomes includes ultracentrifugation, often in combination with sucrose density gradients or sucrose cushions to float the relatively low-density exosomes. Isolation of exosomes by sequential differential centrifugations is complicated by the possibility of overlapping size distributions with other microvesicles or macromolecular complexes. Furthermore, centrifugation may provide insufficient means to separate vesicles based on their sizes. However, sequential centrifugations, when combined with sucrose gradient ultracentrifugation, can provide high enrichment of exosomes.

Isolation of exosomes based on size, using alternatives to the ultracentrifugation routes, is another option. Successful purification of exosomes using ultrafiltration procedures that are less time consuming than ultracentrifugation, and do not require use of special equipment have been reported. Similarly, a commercial kit is available (EXOMIR™, Bioo Scientific) which allows removal of cells, platelets, and cellular debris on one microfilter and capturing of vesicles bigger than 30 nm on a second microfilter using positive pressure to drive the fluid. However, for this process, the exosomes are not recovered, their RNA content is directly extracted from the material caught on the second microfilter, which can then be used for PCR analysis. HPLC-based protocols could potentially allow one to obtain highly pure exosomes, though these processes require dedicated equipment and are difficult to scale up. A significant problem is that both blood and cell culture media contain large numbers of nanoparticles (some non-vesicular) in the same size range as exosomes. For example, some miRNAs may be contained within extracellular protein complexes rather than exosomes; however, treatment with protease (e.g., proteinase K) can be performed to eliminate any possible contamination with "extraexosomal" protein.

In another embodiment, cancer cell-derived exosomes may be captured by techniques commonly used to enrich a sample for exosomes, such as those involving immunospecific interactions (e.g., immunomagnetic capture) Immunomagnetic capture, also known as immunomagnetic cell separation, typically involves attaching antibodies directed to proteins found on a particular cell type to small paramagnetic beads. When the antibody-coated beads are mixed with a sample, such as blood, they attach to and surround the particular cell. The sample is then placed in a strong magnetic field, causing the beads to pellet to one side. After removing the blood, captured cells are retained with the beads. Many variations of this general method are well-known in the art and suitable for use to isolate exosomes. In one example, the exosomes may be attached to magnetic beads (e.g., aldehyde/sulphate beads) and then an antibody is added to the mixture to recognize an epitope on the surface of the exosomes that are attached to the beads. Exemplary proteins that are known to be found on cancer cell-derived exosomes include ATP-binding cassette subfamily A member 6 (ABCA6), tetraspanin-4 (TSPAN4), SLIT and NTRK-like protein 4 (SLITRK4), putative protocadherin beta-18 (PCDHB18), myeloid cell surface antigen CD33 (CD33), and glypican-1 (GPC1). Cancer cell-derived exosomes may be isolated using, for example, antibodies or aptamers to one or more of these proteins.

As used herein, analysis includes any method that allows direct or indirect visualization of exosomes and may be in vivo or ex vivo. For example, analysis may include, but not limited to, ex vivo microscopic or cytometric detection and visualization of exosomes bound to a solid substrate, flow cytometry, fluorescent imaging, and the like. In an exemplary aspect, cancer cell-derived exosomes are detected using antibodies directed to one or more of ATP-binding cassette sub-family A member 6 (ABCA6), tetraspanin-4 (TSPAN4), SLIT and NTRK-like protein 4 (SLITRK4), putative protocadherin beta-18 (PCDHB18), myeloid cell surface antigen CD33 (CD33), glypican-1 (GPC1), Histone H2A type 2-A (HIST1H2AA), Histone H2A type 1-A (HIST1H1AA), Histone H3.3 (H3F3A), Histone H3.1 (HIST1H3A), Zinc finger protein 37 homolog (ZFP37), Laminin subunit beta-1 (LAMB1), Tubulointerstitial nephritis antigen-like (TINAGL1), Peroxiredeoxin-4 (PRDX4), Collagen alpha-2(IV) chain (COL4A2), Putative protein C3P1 (C3P1), Hemicentin-1 (HMCN1), Putative rhophilin-2-like protein (RHPN2P1), Ankyrin repeat domain-containing protein 62 (ANKRD62), Tripartite motif-containing protein 42 (TRIM42), Junction plakoglobin (JUP), Tubulin beta-2B chain (TUBB2B), Endoribonuclease Dicer (DICER1), E3 ubiquitin-protein ligase TRIM71 (TRIM71), Katanin p60 ATPase-containing subunit A-like 2 (KATNAL2), Protein S100-A6 (S100A6), 5'-nucleotidase domain-containing protein 3 (NT5DC3), Valine-tRNA ligase (VARS), Kazrin (KAZN), ELAV-like protein 4 (ELAVL4), RING finger protein 166 (RNF166), FERM and PDZ domain-containing protein 1 (FRMPD1), 78 kDa glucose-regulated protein (HSPA5), Trafficking protein particle complex subunit 6A (TRAPPC6A), Squalene monooxygenase (SQLE), Tumor susceptibility gene 101 protein (TSG101), Vacuolar protein sorting 28 homolog (VPS28), Prostaglandin F2 receptor negative regulator (PTGFRN), Isobutyryl-CoA dehydrogenase, mitochondrial (ACAD8), 26S protease regulatory subunit 6B (PSMC4), Elongation factor 1-gamma (EEF1G), Titin (TTN), Tyrosine-protein phosphatase type 13 (PTPN13), Triosephosphate isomerase (TPI1), or Carboxypeptidase E (CPE) and subsequently bound to a solid substrate and/or visualized using microscopic or cytometric detection.

Figure 11:
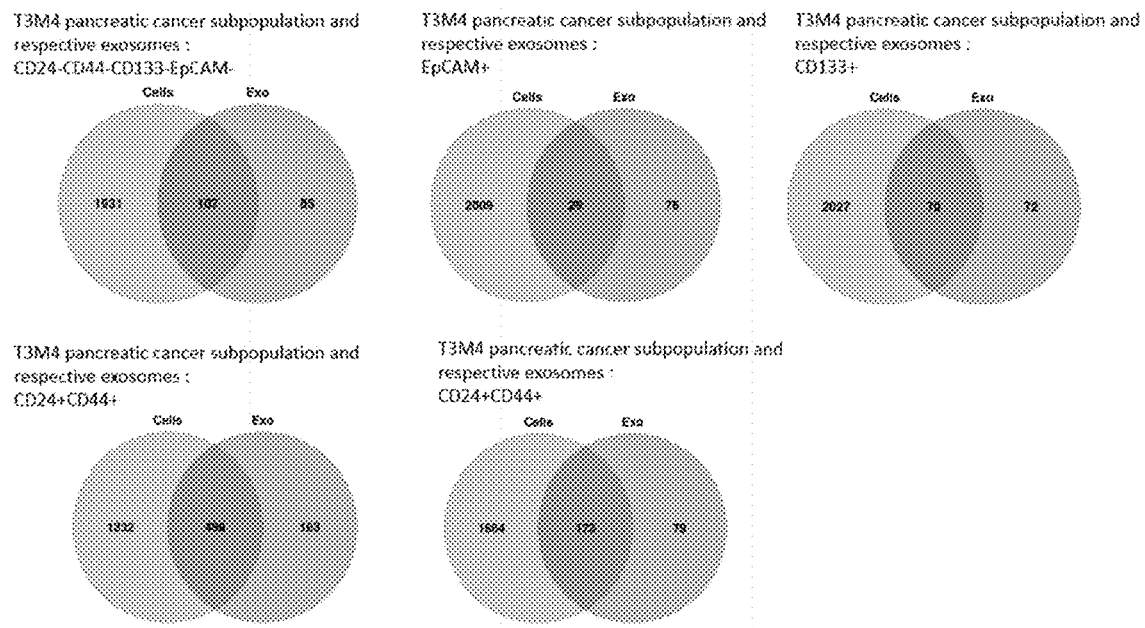
FIG. 11. Venn Diagrams representing the proteins present in subpopulations of pancreatic cancer cells and their respective exosomes. Protein was extracted from subpopulations of the pancreatic cancer cell line T3M4 and their respective exosomes. Mass spectrometry was used to identify proteins expressed in the cells and respective exosomes. A list of proteins was identified for each sample. Comparison between cells and respective exosomes identified proteins present in the cells but not present in exosomes (left side of each pair of circles), proteins present in cells and respective exosomes (intersection between circles) and proteins enriched in exosomes when compared to cells (right side of each pair of circles). Cells express proteins which do not appear in exosomes. Also, exosomes contain enriched proteins when compared with the cell of origin.

It should be noted that not all proteins expressing in a cell are found in exosomes secreted by that cell (see FIG. 11). For example, calnexin, GM130, and LAMP-2 are all proteins expressed in MCF-7 cells but not found in exosomes secreted by MCF-7 cells (Baietti et al., 2012). As another example, one study found that 190/190 pancreatic ductal adenocarcinoma patients had higher levels of GPC1+ exosomes than healthy controls (Melo et al., 2015, which is incorporated herein by reference in its entirety). Notably, only 2.3% of healthy controls, on average, had GPC1+ exosomes.

1. Exemplary Protocol for Collecting Exosomes from Cell Culture

On Day 1, seed enough cells (e.g., about five million cells) in T225 flasks in media containing 10% FBS so that the next day the cells will be about 70% confluent. On Day 2, aspirate the media on the cells, wash the cells twice with PBS, and then add 25-30 mL base media (i.e., no PenStrep or FBS) to the cells. Incubate the cells for 24-48 hours. A 48 hour incubation is preferred, but some cells lines are more sensitive to serum-free media and so the incubation time should be reduced to 24 hours. Note that FBS contains exosomes that will heavily skew NanoSight results.

On Day 3/4, collect the media and centrifuge at room temperature for five minutes at 800×g to pellet dead cells and large debris. Transfer the supernatant to new conical tubes and centrifuge the media again for 10 minutes at 2000×g to remove other large debris and large vesicles. Pass the media through a 0.2 µm filter and then aliquot into ultracentrifuge tubes (e.g., 25×89 mm Beckman Ultra-Clear) using 35 mL per tube. If the volume of media per tube is less than 35 mL, fill the remainder of the tube with PBS to reach 35 mL. Ultracentrifuge the media for 2-4 hours at 28,000 rpm at 4° C. using a SW 32 Ti rotor (k-factor 266.7, RCF max 133,907). Carefully aspirate the supernatant until there is roughly 1-inch of liquid remaining. Tilt the tube and allow remaining media to slowly enter aspirator pipette. If desired, the exosomes pellet can be resuspended in PBS and the ultracentrifugation at 28,000 rpm repeated for 1-2 hours to further purify the population of exosomes.

Finally, resuspend the exosomes pellet in 210 µL PBS. If there are multiple ultracentrifuge tubes for each sample, use the same 210 µL PBS to serially resuspend each exosomes pellet. For each sample, take 10 µL and add to 990 µL $H_2O$ to use for nanoparticle tracking analysis. Use the remaining 200 µL exosomes-containing suspension for downstream processes or immediately store at −80° C.

2. Exemplary Protocol for Extracting Exosomes from Serum Samples

First, allow serum samples to thaw on ice. Then, dilute 250 µL of cell-free serum samples in 11 mL PBS; filter through a 0.2 µm pore filter. Ultracentrifuge the diluted sample at 150,000×g overnight at 4° C. The following day, carefully discard the supernatant and wash the exosomes pellet in 11 mL PBS. Perform a second round of ultracentrifugation at 150,000×g at 4° C. for 2 hours. Finally, carefully discard the supernatant and resuspend the exosomes pellet in 100 µL PBS for analysis.

C. Exemplary Protocol for Electroporation of Exosomes and Liposomes

Mix 1×10$^8$ exosomes (measured by NanoSight analysis) or 100 nm liposomes (e.g., purchased from Encapsula Nano Sciences) and 1 µg of siRNA (Qiagen) or shRNA in 400 µL of electroporation buffer (1.15 mM potassium phosphate, pH 7.2, 25 mM potassium chloride, 21% Optiprep). Electroporate the exosomes or liposomes using a 4 mm cuvette (see, e.g., Alvarez-Erviti et al., 2011; El-Andaloussi et al., 2012). After electroporation, treat the exosomes or liposomes with protease-free RNAse followed by addition of 10× concentrated RNase inhibitor. Finally, wash the exosomes or liposomes with PBS under ultracentrifugation methods, as described above.

II. DIAGNOSIS, PROGNOSIS, AND TREATMENT OF DISEASES

Detection, isolation, and characterization of cancer cell-derived exosomes, using the methods of the invention, is useful in assessing cancer prognosis and in monitoring therapeutic efficacy for early detection of treatment failure that may lead to disease relapse. In addition, cancer cell-derived exosomes analysis according to the invention enables the detection of early relapse in presymptomatic patients who have completed a course of therapy. This is possible because the presence of cancer cell-derived exosomes may be associated and/or correlated with tumor progression and spread, poor response to therapy, relapse of disease, and/or decreased survival over a period of time. Thus, enumeration and characterization of cancer cell-derived exosomes provides methods to stratify patients for baseline characteristics that predict initial risk and subsequent risk based upon response to therapy.

Cancer cell-derived exosomes isolated according to the methods disclosed herein may be analyzed to diagnose or prognose cancer in the subject. As such, the methods of the present invention may be used, for example, to evaluate cancer patients and those at risk for cancer. In any of the methods of diagnosis or prognosis described herein, either the presence or the absence of one or more indicators of cancer, such as a genomic mutation or cancer-specific exosomes surface marker, or of any other disorder, may be used to generate a diagnosis or prognosis.

In one aspect, a blood sample is drawn from the patient and cancer cell-derived exosomes are detected and/or isolated as described herein. For example, the exosomes may be labeled with one or more antibodies or aptamers that bind to ATP-binding cassette sub-family A member 6 (ABCA6), tetraspanin-4 (TSPAN4), SLIT and NTRK-like protein 4 (SLITRK4), putative protocadherin beta-18 (PCDHB18), myeloid cell surface antigen CD33 (CD33), and/or glypican-1 (GPC1), and the antibodies may have a covalently bound fluorescent label. Analysis may then be performed to determine the number and characterization of cancer cell-derived exosomes in the sample, and from this measurement, the number of cancer cell-derived exosomes present in the initial blood sample may be determined. Exosomes identified as cancer cell-derived exosomes may be verified as such through the detection of a second (or more) marker known to be found selectively or specifically in cancer cell-derived exosomes, such as, for example, Histone H2A type 2-A (HIST1H2AA), Histone H2A type 1-A (HIST1H1AA), Histone H3.3 (H3F3A), Histone H3.1 (HIST1H3A), Zinc finger protein 37 homolog (ZFP37), Laminin subunit beta-1 (LAMB1), Tubulointerstitial nephritis antigen-like (TINAGL1), Peroxiredoxin-4 (PRDX4), Collagen alpha-2(IV) chain (COL4A2), Putative protein C3P1 (C3P1), Hemicentin-1 (HMCN1), Putative rhophilin-2-like protein (RHPN2P1), Ankyrin repeat domain-containing protein 62 (ANKRD62), Tripartite motif-containing protein 42 (TRIM42), Junction plakoglobin (JUP), Tubulin beta-2B chain (TUBB2B), Endoribonuclease Dicer (DICER1), E3 ubiquitin-protein ligase TRIM71 (TRIM71), Katanin p60 ATPase-containing subunit A-like 2 (KATNAL2), Protein S100-A6 (S100A6), 5'-nucleotidase domain-containing protein 3 (NT5DC3), Valine-tRNA ligase (VARS), Kazrin (KAZN), ELAV-like protein 4 (ELAVL4), RING finger protein 166 (RNF166), FERM and PDZ domain-containing protein 1 (FRMPD1), 78 kDa glucose-regulated protein (HSPA5), Trafficking protein particle complex subunit 6A (TRAPPC6A), Squalene monooxygenase (SQLE), Tumor susceptibility gene 101 protein (TSG101), Vacuolar protein sorting 28 homolog (VPS28), Prostaglandin F2 receptor negative regulator (PTGFRN), Isobutyryl-CoA dehydrogenase, mitochondrial (ACAD8), 26S protease regulatory subunit 6B (PSMC4), Elongation factor 1-gamma (EEF1G), Titin (TTN), Tyrosine-protein phosphatase type 13 (PTPN13), Triosephosphate isomerase (TPI1), or Carboxypeptidase E (CPE). The number of cancer cell-derived exosomes may be determined by cytometric or microscopic techniques to visually quantify and characterize the exosomes. Cancer cell-derived exosomes may be detected and quantified by other methods known in the art (e.g., ELISA).

In various aspects, analysis of a subject's cancer cell-derived exosomes number and characterization may be made over a particular time course in various intervals to assess a subject's progression and pathology. For example, analysis may be performed at regular intervals such as one day, two days, three days, one week, two weeks, one month, two months, three months, six months, or one year, in order to track the level and characterization of cancer cell-derived exosomes as a function of time. In the case of existing cancer patients, this provides a useful indication of the progression of the disease and assists medical practitioners in making appropriate therapeutic choices based on the increase, decrease, or lack of change in cancer cell-derived exosomes. Any increase, be it 2-fold, 5-fold, 10-fold or higher, in cancer cell-derived exosomes over time decreases the patient's prognosis and is an early indicator that the patient should change therapy. Similarly, any increase, be it 2-fold, 5-fold, 10-fold or higher, indicates that a patient should undergo further testing such as imaging to further assess prognosis and response to therapy. Any decrease, be it 2-fold, 5-fold, 10-fold or higher, in cancer cell-derived exosomes over time shows disease stabilization and a patient's response to therapy, and is an indicator to not change therapy. For those at risk of cancer, a sudden increase in the number of cancer cell-derived exosomes detected may provide an early warning that the patient has developed a tumor thus providing an early diagnosis. In one embodiment, the detection of cancer cell-derived exosomes increases with the staging of the cancer.

In any of the methods provided herein, additional analysis may also be performed to characterize cancer cell-derived exosomes to provide additional clinical assessment. For example, in addition to image analysis and bulk number measurements, PCR techniques may be employed, such as multiplexing with primers specific for particular cancer markers to obtain information such as the type of tumor from which the cancer cell-derived exosomes originated, metastatic state, and degree of malignancy. Additionally, DNA or RNA analysis, proteome analysis, or metabolome analysis may be performed as a means of assessing additional information regarding characterization of the patient's cancer.

For example, the additional analysis may provide data sufficient to make determinations of responsiveness of a subject to a particular therapeutic regime, or for determining the effectiveness of a candidate agent in the treatment of cancer. Accordingly, the present invention provides a method of determining responsiveness of a subject to a particular therapeutic regime or determining the effectiveness of a candidate agent in the treatment of cancer by detecting/isolating cancer cell-derived exosomes of the subject as described herein and analyzing said cancer cell-derived exosomes. For example, once a drug treatment is administered to a patient, it is possible to determine the efficacy of the drug treatment using the methods of the invention. For example, a sample taken from the patient before the drug treatment, as well as one or more samples taken from the patient concurrently with or subsequent to the drug treatment, may be processed using the methods of the invention. By comparing the results of the analysis of each processed sample, one may determine the efficacy of the drug treatment or the responsiveness of the patient to the agent. In this manner, early identification may be made of failed compounds or early validation may be made of promising compounds.

Certain aspects of the present invention provide for treating a patient with exosomes that express or comprise a therapeutic agent or a diagnostic agent. A "therapeutic agent" as used herein is an atom, molecule, or compound that is useful in the treatment of cancer or other conditions. Examples of therapeutic agents include, but are not limited to, drugs, chemotherapeutic agents, therapeutic antibodies and antibody fragments, toxins, radioisotopes, enzymes, nucleases, hormones, immunomodulators, antisense oligonucleotides, chelators, boron compounds, photoactive agents, and dyes. A "diagnostic agent" as used herein is an atom, molecule, or compound that is useful in diagnosing, detecting or visualizing a disease. According to the embodiments described herein, diagnostic agents may include, but are not limited to, radioactive substances (e.g., radioisotopes, radionuclides, radiolabels or radiotracers), dyes, contrast agents, fluorescent compounds or molecules, bioluminescent compounds or molecules, enzymes and enhancing agents (e.g., paramagnetic ions).

In some aspects, a therapeutic recombinant protein may be a protein having an activity that has been lost in a cell of the patient, a protein having a desired enzymatic activity, a protein having a desired inhibitory activity, etc. For example, the protein may be a transcription factor, an enzyme, a proteinaceous toxin, an antibody, a monoclonal antibody, etc. The monoclonal antibody may specifically or selectively bind to an intracellular antigen. The monoclonal antibody may inhibit the function of the intracellular antigen and/or disrupt a protein-protein interaction. Other aspects of the present invention provide for diagnosing a disease based on the presence of cancer cell-derived exosomes in a patient sample.

As exosomes are known to comprise the machinery necessary to complete mRNA transcription and protein translation (see PCT/US2014/068630, which is incorporated herein by reference in its entirety), mRNA or DNA nucleic acids encoding a therapeutic protein may be transfected into exosomes. Alternatively, the therapeutic protein itself may be electroporated into the exosomes or incorporated directly into a liposome. Exemplary therapeutic proteins include, but are not limited to, a tumor suppressor protein, peptides, a wild type protein counterparts of a mutant protein, a DNA repair protein, a proteolytic enzyme, proteinaceous toxin, a protein that can inhibit the activity of an intracellular protein, a protein that can activate the activity of an intracellular protein, or any protein whose loss of function needs to be reconstituted. Specific examples of exemplary therapeutic proteins include 123F2, Abcb4, Abcc1, Abcg2, Actb, Ada, Ahr, Akt, Akt1, Akt2, Akt3, Amhr2, Anxa7, Apc, Ar, Atm, Axin2, B2m, Bard1, Bcl2l1, Becn1, Bhlha15, Bin1, Blm, Braf, Brca1, Brca2, Brca3, Braf, Brcata, Brinp3, Brip1, Bub1b, Bwscr1a, Cadm3, Casc1, Casp3, Casp7, Casp8, Cav1, Ccam, Ccnd1, Ccr4, Ccs1, Cd28, Cdc25a, Cd95, Cdh1, Cdkn1a, Cdkn1b, Cdkn2a, Cdkn2b, Cdkn2c, Cftr, Chek1, Chek2, Crcs1, Crcs10, Crcs11, Crcs2, Crcs3, Crcs4, Crcs5, Crcs6, Crcs7, Crcs8, Crcs9, Ctnnb1, Cts1, Cypla1, Cyp2a6, Cyp2b2, Cy1d, Dcc, Dkc1, Dicer1, Dmtf1, Dnmt1, Dpc4, E2f1, Eaf2, Eef1a1, Egfr, Egfr4, Erbb2, Erbb4, Ercc2, Ercc6, Ercc8, Errfi1, Esr1, Etv4, Fas1g, Fbxo10, Fcc, Fgfr3, Fntb, Foxm1, Foxn1, Fus1, Fzd6, Fzd7, Fzr1, Gadd45a, Gast, Gnai2, Gpc1, Gpr124, Gpr87, Gprc5a, Gprc5d, Grb2, Gstm1, Gstm5, Gstp1, Gstt1, H19, H2afx, Hck, Lims1, Hdac, Hexa, Hic1, Hin1, Hmmr, Hnpcc8, Hprt, Hras, Htatip2, Il1b, Il110, Il2, Il6, Il8rb Inha, Itgav, Jun, Jak3, Kit, Klf4, Kras, Kras2, Kras2b, Lig1, Lig4, Lkb1, Lmo7, Lncr1, Lncr2, Lncr3, Lncr4, Ltbp4, Luca1, Luca2, Lyz2, Lzts1, Mad111, Mad211, Madr2/Jv18, Mapk14, Mcc, Mcm4, Men1, Men2, Met, Mgat5, Mif, Mlh1, Mlh3, Mmac1, Mmp8, Mnt, Mpo, Msh2, Msh3, Msh6, Msmb, Mthfr, Mts1, Mutyh, Myh11, Nat2, Nbn, Ncoa3, Neil1, Nf1, Nf2, Nfe211, Nhej1, Nkx2-1, Nkx2-9, Nkx3-1, Nprl2, Nqo1, Nras, Nudt1, Ogg1, Oxgr1, p16, p19, p21, p27, p27mt, p57, p14ARF, Pa1b2, Park2, Pggt1b, Pgr, Pi3k, Pik3ca, Piwil2, P16, Pla2g2a, Plg, P1k3, Pms1, Pms2, Pold1, Pole, Ppard, Pparg, Ppfia2, Ppm1d, Prdm2, Prdx1, Prkar1a, Ptch, Pten, Prom1, Psca, Ptch1, Ptf1a, Ptger2, Ptpn13, Ptprj, Rara, Rad51, Rassf1, Rb, Rb1, Rb1cc1, Rb12, Recg14, Ret, Rgs5, Rhoc, Rint1, Robo1, Rp138, S100a4, SCGB1A1, Skp2, Smad2, Smad3, Smad4, Smarcb1, Smo, Snx25, Spata13, Srpx, Ssic1, Sstr2, Sstr5, Stat3, St5, St7, St14, Stk11, Suds3, Tap1, Tbx21, Terc, Tnf, Tp53, Tp73, Trpm5, Tsc2, Tsc1, Vh1, Wrn, Wt1, Wt2, Xrcc1, Xrcc5, Xrcc6, and Zac1.

One specific type of protein that it may be desirable to introduce into the intracellular space of a diseased cell is an antibody (e.g., a monoclonal antibody). Such an antibody may disrupt the function of an intracellular protein and/or disrupt an intracellular protein-protein interaction. Exemplary targets of such monoclonal antibodies include, but are not limited to, proteins involved in the RNAi pathway, telomerase, transcription factors that control disease processes, kinases, phosphatases, proteins required for DNA synthesis, protein required for protein translation. Specific examples of exemplary therapeutic antibody targets include proteins encoded by the following genes: Dicer, Ago1, Ago2, Trbp, Ras, raf, wnt, btk, Bcl-2, Akt, Sis, src, Notch, Stathmin, mdm2, ab1, hTERT, c-fos, c-jun, c-myc, erbB, HER2/Neu, HER3, VEGFR, PDGFR, c-kit, c-met, c-ret, flt3, API, AML1, axl, alk, fins, fps, gip, lck, Stat, Hox, MLM, PRAD-I, and trk. In addition to monoclonal antibodies, any antigen binding fragment there of, such as a scFv, a Fab fragment, a Fab', a F(ab')2, a Fv, a peptibody, a diabody, a triabody, or a minibody, is also contemplated. Any such antibodies or antibody fragment may be either glycosylated or aglycosylated.

As exosomes are known to comprise DICER and active RNA processing RISC complex (see PCT Publn. WO 2014/152622, which is incorporated herein by reference in its entirety), shRNA transfected into exosomes can mature into RISC-complex bound siRNA with the exosomes themselves. Alternatively, mature siRNA can itself be transfected into exosomes or liposomes. Thus, by way of example, the following are classes of possible target genes that may be used in the methods of the present invention to modulate or attenuate target gene expression: wild-type or mutant versions of developmental genes (e.g., adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), tumor suppressor genes (e.g., APC, CYLD, HIN-1, KRAS2b, p16, p19, p21, p27, p27mt, p53, p57, p73, PTEN, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zac1, ras, MMAC1, FCC, MCC, FUS1, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide), pro-apoptotic genes (e.g., CD95, caspase-3, Bax, Bag-1, CRADD, TSSC3, bax, hid, Bak, MKP-7, PARP, bad, bc1-2, MST1, bbc3, Sax, BIK, and BID), cytokines (e.g., GM-CSF, G-CSF, IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 IFN-α, IFN-β, IFN-γ, MIP-1α, MIP-1β, TGF-β, TNF-α, TNF-β, PDGF, and mda7), oncogenes (e.g., ABLI, BLC1, BCL6, CBFA1, CBL, CSFIR, ERBA, ERBB, EBRB2, ETS1, ETS1, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES), and enzymes (e.g., ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, galactosidases, glucanases, glucose oxidases, GTPases, helicases, hemicellulases, integrases, invertases, isomersases, kinases, lactases, lipases, lipoxygenases, lysozymes, nucleases, pectinesterases, peroxidases, phosphatases, phospholipases, phosphorylases, polygalacturonases, proteinases and peptideases, pullanases, recombinases, reverse transcriptases, topoisomerases, xylanases). In some cases, sh/siRNA may be designed to specifically target a mutant version of a gene expressed in a cancer cell while not affecting the expression of the corresponding wild-type version. In fact, any inhibitory nucleic acid that can be applied in the compositions and methods of the present invention if such inhibitory nucleic acid has been found by any source to be a validated downregulator of a protein of interest.

In designing RNAi there are several factors that need to be considered, such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80%, 85%, 90%, 95%, 98%, or even 100% identity between the sequence of the siRNA and the gene to be inhibited. Sequences less than about 80% identical to the target gene are substantially less effective. Thus, the greater homology between the siRNA and the gene to be inhibited, the less likely expression of unrelated genes will be affected.

In addition to protein- and nucleic acid-based therapeutics, exosomes may be used to deliver small molecule drugs, either alone or in combination with any protein- or nucleic acid-based therapeutic. Exemplary small molecule drugs that are contemplated for use in the present embodiments include, but are not limited to, toxins, chemotherapeutic agents, agents that inhibit the activity of an intracellular protein, agents that activate the activity of intracellular proteins, agents for the prevention of restenosis, agents for treating renal disease, agents used for intermittent claudication, agents used in the treatment of hypotension and shock, angiotensin converting enzyme inhibitors, antianginal agents, anti-arrhythmics, anti-hypertensive agents, antiotensin ii receptor antagonists, antiplatelet drugs, b-blockers b1 selective, beta blocking agents, botanical product for cardiovascular indication, calcium channel blockers, cardiovascular/diagnostics, central alpha-2 agonists, coronary vasodilators, diuretics and renal tubule inhibitors, neutral endopeptidase/angiotensin converting enzyme inhibitors, peripheral vasodilators, potassium channel openers, potassium salts, anticonvulsants, antiemetics, antinauseants, antiparkinson agents, antispasticity agents, cerebral stimulants, agents that can be applied in the treatment of trauma, agents that can be applied in the treatment of Alzheimer disease or dementia, agents that can be applied in the treatment of migraine, agents that can be applied in the treatment of neurodegenerative diseases, agents that can be applied in the treatment of kaposi's sarcoma, agents that can be applied in the treatment of AIDS, cancer chemotherapeutic agents, agents that can be applied in the treatment of immune disorders, agents that can be applied in the treatment of psychiatric disorders, analgesics, epidural and intrathecal anesthetic agents, general, local, regional neuromuscular blocking agents sedatives, preanesthetic adrenal/acth, anabolic steroids, agents that can be applied in the treatment of diabetes, dopamine agonists, growth hormone and analogs, hyperglycemic agents, hypoglycemic agents, oral insulins, large volume parenterals (lvps), lipid-altering agents, metabolic studies and inborn errors of metabolism, nutrients/amino acids, nutritional lvps, obesity drugs (anorectics), somatostatin, thyroid agents, vasopressin, vitamins, corticosteroids, mucolytic agents, pulmonary anti-inflammatory agents, pulmonary surfactants, antacids, anticholinergics, antidiarrheals, antiemetics, cholelitholytic agents, inflammatory bowel disease agents, irritable bowel syndrome agents, liver agents, metal chelators, miscellaneous gastric secretory agents, pancreatitis agents, pancreatic enzymes, prostaglandins, prostaglandins, proton pump inhibitors, sclerosing agents, sucralfate, anti-progestins, contraceptives, oral contraceptives, not oral dopamine agonists, estrogens, gonadotropins, GNRH agonists, GHRH antagonists, oxytocics, progestins, uterine-acting agents, anti-anemia drugs, anticoagulants, antifibrinolytics, antiplatelet agents, antithrombin drugs, coagulants, fibrinolytics, hematology, heparin inhibitors, metal chelators, prostaglandins, vitamin K, anti-androgens, aminoglycosides, antibacterial agents, sulfonamides, cephalosporins, clindamycins, dermatologics, detergents, erythromycins, anthelmintic agents, antifungal agents, antimalarials, antimycobacterial agents, antiparasitic agents, antiprotozoal agents, antitrichomonads, antituberculosis agents, immunomodulators, immunostimulatory agents, macrolides, antiparasitic agents, corticosteroids, cyclooxygenase inhibitors, enzyme blockers, immunomodulators for rheumatic diseases, metalloproteinase inhibitors, nonsteroidal anti-inflammatory agents, analgesics, antipyretics, alpha adrenergic agonists/blockers, antibiotics, antivirals, beta adrenergic blockers, carbonic anhydrase inhibitors, corticosteroids, immune system regulators, mast cell inhibitors, nonsteroidal anti-inflammatory agents, and prostaglandins.

Exosomes may also be used to deliver diagnostic agents. Exemplary diagnostic agents include, but are not limited to, magnetic resonance image enhancement agents, positron emission tomography products, radioactive diagnostic agents, radioactive therapeutic agents, radio-opaque contrast agents, radiopharmaceuticals, ultrasound imaging agents, and angiographic diagnostic agents.

The term "subject" as used herein refers to any individual or patient to which the subject methods are performed. Generally the subject is human, although as will be appreciated by those in the art, the subject may be an animal Thus other animals, including mammals, such as rodents (including mice, rats, hamsters, and guinea pigs), cats, dogs, rabbits, farm animals (including cows, horses, goats, sheep, pigs, etc.), and primates (including monkeys, chimpanzees, orangutans, and gorillas) are included within the definition of subject.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of chemotherapy, immunotherapy, or radiotherapy, performance of surgery, or any combination thereof.

The term "therapeutic benefit" or "therapeutically effective" as used herein refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the invasiveness of a tumor, reduction in the growth rate of the cancer, or prevention of metastasis. Treatment of cancer may also refer to prolonging survival of a subject with cancer.

The term "cancer," as used herein, may be used to describe a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Nonetheless, it is also recognized that the present invention may also be used to treat a non-cancerous disease (e.g., a fungal infection, a bacterial infection, a viral infection, a neurodegenerative disease, and/or a genetic disorder).

The terms "contacted" and "exposed," when applied to a cell, are used herein to describe the process by which a therapeutic agent is delivered to a target cell or are placed in direct juxtaposition with the target cell. To achieve cell killing, for example, one or more agents are delivered to a cell in an amount effective to kill the cell or prevent it from dividing.

An effective response of a patient or a patient's "responsiveness" to treatment refers to the clinical or therapeutic benefit imparted to a patient at risk for, or suffering from, a disease or disorder. Such benefit may include cellular or biological responses, a complete response, a partial response, a stable disease (without progression or relapse), or a response with a later relapse. For example, an effective response can be reduced tumor size or progression-free survival in a patient diagnosed with cancer.

Treatment outcomes can be predicted and monitored and/or patients benefiting from such treatments can be identified or selected via the methods described herein.

Regarding neoplastic condition treatment, depending on the stage of the neoplastic condition, neoplastic condition treatment involves one or a combination of the following therapies: surgery to remove the neoplastic tissue, radiation therapy, and chemotherapy. Other therapeutic regimens may be combined with the administration of the anticancer agents, e.g., therapeutic compositions and chemotherapeutic agents. For example, the patient to be treated with such anti-cancer agents may also receive radiation therapy and/or may undergo surgery.

For the treatment of disease, the appropriate dosage of a therapeutic composition will depend on the type of disease to be treated, as defined above, the severity and course of the disease, the patient's clinical history and response to the agent, and the discretion of the attending physician. The agent is suitably administered to the patient at one time or over a series of treatments.

Therapeutic and prophylactic methods and compositions can be provided in a combined amount effective to achieve the desired effect. A tissue, tumor, or cell can be contacted with one or more compositions or pharmacological formulation(s) comprising one or more of the agents, or by contacting the tissue, tumor, and/or cell with two or more distinct compositions or formulations. Also, it is contemplated that such a combination therapy can be used in conjunction with chemotherapy, radiotherapy, surgical therapy, or immunotherapy.

Administration in combination can include simultaneous administration of two or more agents in the same dosage form, simultaneous administration in separate dosage forms, and separate administration. That is, the subject therapeutic composition and another therapeutic agent can be formulated together in the same dosage form and administered simultaneously. Alternatively, subject therapeutic composition and another therapeutic agent can be simultaneously administered, wherein both the agents are present in separate formulations. In another alternative, the therapeutic agent can be administered just followed by the other therapeutic agent or vice versa. In the separate administration protocol, the subject therapeutic composition and another therapeutic agent may be administered a few minutes apart, or a few hours apart, or a few days apart.

A first anti-cancer treatment (e.g., exosomes that express a recombinant protein or with a recombinant protein isolated from exosomes) may be administered before, during, after, or in various combinations relative to a second anti-cancer treatment. The administrations may be in intervals ranging from concurrently to minutes to days to weeks. In embodiments where the first treatment is provided to a patient separately from the second treatment, one would generally ensure that a significant period of time did not expire between the time of each delivery, such that the two compounds would still be able to exert an advantageously combined effect on the patient. In such instances, it is contemplated that one may provide a patient with the first therapy and the second therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a first anti-cancer therapy is "A" and a second anti-cancer therapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present invention to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammal1 and calicheamicin omega1 1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the invention. In the context of cancer treatment, immunotherapeutics, generally, rely on the use of immune effector cells and molecules to target and destroy cancer cells. Rituximab (Rituxan®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2013; Hanibuchi et al., 1998; U.S. Pat. No. 5,824,311). It is contemplated that one or more anti-cancer therapies may be employed with the antibody therapies described herein.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present invention, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present invention to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present invention to improve the treatment efficacy.

III. PHARMACEUTICAL COMPOSITIONS

It is contemplated that exosomes that express or comprise a recombinant protein, inhibitory RNA, and/or small molecule drug can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

It is not intended that the present invention be limited by the particular nature of the therapeutic preparation. For example, such compositions can be provided in formulations together with physiologically tolerable liquid, gel, solid carriers, diluents, or excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particular requirements of individual subjects.

Where clinical applications are contemplated, it may be necessary to prepare pharmaceutical compositions comprising recombinant proteins and/or exosomes in a form appropriate for the intended application. Generally, pharmaceutical compositions, which can be parenteral formulations, can comprise an effective amount of one or more recombinant proteins and/or exosomes and/or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition comprising a recombinant protein and/or exosomes as disclosed herein, or additional active ingredients is as exemplified by Remington's Pharmaceutical Sciences, 18th Ed., 1990, which is incorporated herein by reference in its entirety for all purposes. Moreover, for animal (e.g., human) administration, it will be understood that preparations should meet sterility, pyrogenicity, general safety, and purity standards as required by the FDA Office of Biological Standards.

Further in accordance with certain aspects of the present invention, the composition suitable for administration may be provided in a pharmaceutically acceptable carrier with or without an inert diluent. As used herein, "pharmaceutically acceptable carrier" includes any and all aqueous solvents (e.g., water, alcoholic/aqueous solutions, ethanol, saline solutions, parenteral vehicles, such as sodium chloride, Ringer's dextrose, etc.), non-aqueous solvents (e.g., fats, oils, polyol (for example, glycerol, propylene glycol, and liquid polyethylene glycol, and the like), vegetable oil, and injectable organic esters, such as ethyloleate), lipids, liposomes, dispersion media, coatings (e.g., lecithin), surfactants, antioxidants, preservatives (e.g., antibacterial or antifungal agents, anti-oxidants, chelating agents, inert gases, parabens (e.g., methylparabens, propylparabens), chlorobutanol, phenol, sorbic acid, thimerosal or combinations thereof), isotonic agents (e.g., sugars and sodium chloride), absorption delaying agents (e.g., aluminum monostearate and gelatin), salts, drugs, drug stabilizers, gels, resins, fillers, binders, excipients, disintegration agents, lubricants, sweetening agents, flavoring agents, dyes, fluid and nutrient replenishers, such like materials and combinations thereof, as would be known to one of ordinary skill in the art. The carrier should be assimilable and includes liquid, semi-solid, i.e., pastes, or solid carriers. In addition, if desired, the compositions may contain minor amounts of auxiliary substances, such as wetting or emulsifying agents, stabilizing agents, or pH buffering agents. The pH and exact concentration of the various components in a pharmaceutical composition are adjusted according to well-known parameters. The proper fluidity can be maintained, for example, by the use of a coating, such as lecithin, by the maintenance of the required particle size in the case of dispersion, and by the use of surfactants.

A pharmaceutically acceptable carrier is particularly formulated for administration to a human, although in certain embodiments it may be desirable to use a pharmaceutically acceptable carrier that is formulated for administration to a non-human animal but that would not be acceptable (e.g., due to governmental regulations) for administration to a human. Except insofar as any conventional carrier is incompatible with the active ingredient (e.g., detrimental to the recipient or to the therapeutic effectiveness of a composition contained therein), its use in the therapeutic or pharmaceutical compositions is contemplated. In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing, which are described, for example, in Remington's Pharmaceutical Sciences, 18th Ed., 1990, incorporated herein by reference.

The active compounds can be formulated for parenteral administration, e.g., formulated for injection via the intravenous, intramuscular, sub-cutaneous, or even intraperitoneal routes. As such, the embodiments include parenteral formulations. Typically, such compositions can be prepared as either liquid solutions or suspensions; solid forms suitable for use to prepare solutions or suspensions upon the addition of a liquid prior to injection can also be prepared; and the preparations can also be emulsified.

According to the subject embodiments, the parenteral formulations can include exosomes as disclosed herein along with one or more solute and/or solvent, one or more buffering agent and/or one or more antimicrobial agents, or any combination thereof. In some aspects, the solvent can include water, water-miscible solvents, e.g., ethyl alcohol, liquid polyethylene glycol, and/or propylene glycol, and/or water-immiscible solvents, such as fixed oils including, for example, corn oil, cottonseed oil, peanut oil, and/or sesame oil. In certain versions, the solutes can include one or more antimicrobial agents, buffers, antioxidants, tonicity agents, cryoprotectants and/or lyoprotectants.

Antimicrobial agents according to the subject disclosure can include those provided elsewhere in the subject disclosure as well as benzyl alcohol, phenol, mercurials and/or parabens. Antimicrobial agents can include benzalkonium chloride, benzethonium chloride, benzyl alcohol, bronopol, centrimide, cetylpyridinium chloride, chlorhexidine, chlorobutanol, chlorocresol, chloroxylenol, cresol, ethyl alcohol, glycerin, exetidine, imidurea, phenol, phenoxyethanol, phenylethl alcohol, phenlymercuric nitrate, propylene glycol, and/or thimerosal, or any combination thereof. The antimicrobial agents can, in various aspects, be present in a concentration necessary to ensure sterility as is required for pharmaceutical agents. For example, the agents can be present in bacteriostatic or fungistatic concentrations in preparations, e.g., preparations contained in multiple-dose containers. The agents can, in various embodiments, be preservatives and/or can be present in adequate concentration at the time of use to prevent the multiplication of microorganisms, such as microorganisms inadvertently introduced into the preparation while, for example, withdrawing a portion of the contents with a hypodermic needle and syringe. In various aspects, the agents have maximum volume and/or concentration limits (e.g., phenylmercuric nitrate and thimerosal 0.01%, benzethonium chloride and benzalkonium chloride 0.01%, phenol or cresol 0.5%, and chlorobutanol 0.5%). In various instances, agents such as phenylmercuric nitrate, are employed in a concentration of 0.002%. Methyl p-hydroxybenzoate 0.18% and propyl p-hydroxybenzoate 0.02% in combination, and benzyl alcohol 2% also can be applied according to the embodiments. The antimicrobial agents can also include hexylresorcinol 0.5%, phenylmercuric benzoate 0.1%, and/or therapeutic compounds.

Antioxidants according to the subject disclosure can include ascorbic acid and/or its salts, and/or the sodium salt of ethylenediaminetetraacetic acid (EDTA). Tonicity agents as described herein can include electrolytes and/or mono- or disaccharides. Cryoprotectants and/or lyoprotectants are additives that protect biopharmaceuticals from detrimental effects due to freezing and/or drying of the product during freeze dry processing. Cryoprotectants and/or lyoprotectants can include sugars (non-reducing) such as sucrose or trehalose, amino acids such as glycine or lysine, polymers such as liquid polyethylene glycol or dextran, and polyols such as mannitol or sorbitol all are possible cryo- or lyoprotectants. The subject embodiments can also include antifungal agents such as butyl paraben, methyl paraben, ethyl paraben, propyl paraben, benzoic acid, potassium sorbate, sodium benzoate, sodium propionate, and/or sorbic acid, or any combination thereof. Additional solutes and antimicrobial agents, buffers, antioxidants, tonicity agents, cryoprotectants and/or lyoprotectants and characteristics thereof which may be employed according to the subject disclosure, as well as aspects of methods of making the subject parenteral formulations are described, for example, in Remington's Pharmaceutical Sciences, 21st Ed., 2005, e.g., Chapter 41, which is incorporated herein by reference in its entirety for all purposes.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The therapeutics may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid and the like. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine and the like. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

In a specific embodiment of the present invention, the composition is combined or mixed thoroughly with a semisolid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition comprising one or more lipids and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man) However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the therapeutic agent may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present invention administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

IV. NUCLEIC ACIDS AND VECTORS

In certain aspects of the invention, nucleic acid sequences encoding a therapeutic protein or a fusion protein containing a therapeutic protein may be disclosed. Depending on which expression system is used, nucleic acid sequences can be selected based on conventional methods. For example, the respective genes or variants thereof may be codon optimized for expression in a certain system. Various vectors may be also used to express the protein of interest. Exemplary vectors include, but are not limited, plasmid vectors, viral vectors, transposon, or liposome-based vectors.

V. RECOMBINANT PROTEINS AND INHIBITORY RNAS

Some embodiments concern recombinant proteins and polypeptides. Particular embodiments concern a recombinant protein or polypeptide that exhibits at least one therapeutic activity. In some embodiments, a recombinant protein or polypeptide may be a therapeutic antibody. In some aspects, a therapeutic antibody may be an antibody that specifically or selectively binds to an intracellular protein. In further aspects, the protein or polypeptide may be modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide. It is specifically contemplated that embodiments concerning a "modified protein" may be implemented with respect to a "modified polypeptide," and vice versa.

Recombinant proteins may possess deletions and/or substitutions of amino acids; thus, a protein with a deletion, a protein with a substitution, and a protein with a deletion and a substitution are modified proteins. In some embodiments, these proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A recombinant protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide," and "peptide are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Certain embodiments of the present invention concern fusion proteins. These molecules may have a therapeutic protein linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the therapeutic protein may be linked to a peptide that increases the in vivo half-life, such as an XTEN polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

siNA (e.g., siRNA) are well known in the art. For example, siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety.

Within a siNA, the components of a nucleic acid need not be of the same type or homogenous throughout (e.g., a siNA may comprise a nucleotide and a nucleic acid or nucleotide analog). Typically, siNA form a double-stranded structure; the double-stranded structure may result from two separate nucleic acids that are partially or completely complementary. In certain embodiments of the present invention, the siNA may comprise only a single nucleic acid (polynucleotide) or nucleic acid analog and form a double-stranded structure by complementing with itself (e.g., forming a hairpin loop). The double-stranded structure of the siNA may comprise 16, 20, 25, 30, 35, 40, 45, 50, 60, 65, 70, 75, 80, 85, 90, 100, 150, 200, 250, 300, 350, 400, 450, 500 or more contiguous nucleobases, including all ranges therein. The siNA may comprise 17 to 35 contiguous nucleobases, more preferably 18 to 30 contiguous nucleobases, more preferably 19 to 25 nucleobases, more preferably 20 to 23 contiguous nucleobases, or 20 to 22 contiguous nucleobases, or 21 contiguous nucleobases that hybridize with a complementary nucleic acid (which may be another part of the same nucleic acid or a separate complementary nucleic acid) to form a double-stranded structure.

Agents of the present invention useful for practicing the methods of the present invention include, but are not limited to siRNAs. Typically, introduction of double-stranded RNA (dsRNA), which may alternatively be referred to herein as small interfering RNA (siRNA), induces potent and specific gene silencing, a phenomena called RNA interference or RNAi. RNA interference has been referred to as "cosuppression," "post-transcriptional gene silencing," "sense suppression," and "quelling." RNAi is an attractive biotechnological tool because it provides a means for knocking out the activity of specific genes.

In designing RNAi there are several factors that need to be considered, such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80%, 85%, 90%, 95%, 98%, or even 100% identity between the sequence of the siRNA and the gene to be inhibited. Sequences less than about 80% identical to the target gene are substantially less effective. Thus, the greater homology between the siRNA and the gene to be inhibited, the less likely expression of unrelated genes will be affected.

In addition, the size of the siRNA is an important consideration. In some embodiments, the present invention relates to siRNA molecules that include at least about 19-25 nucleotides and are able to modulate gene expression. In the context of the present invention, the siRNA is preferably less than 500, 200, 100, 50, or 25 nucleotides in length. More preferably, the siRNA is from about 19 nucleotides to about 25 nucleotides in length.

A target gene generally means a polynucleotide comprising a region that encodes a polypeptide, or a polynucleotide region that regulates replication, transcription, or translation or other processes important to expression of the polypeptide, or a polynucleotide comprising both a region that encodes a polypeptide and a region operably linked thereto that regulates expression. Any gene being expressed in a cell can be targeted. Preferably, a target gene is one involved in or associated with the progression of cellular activities important to disease or of particular interest as a research object.

siRNA can be obtained from commercial sources, natural sources, or can be synthesized using any of a number of techniques well-known to those of ordinary skill in the art. For example, one commercial source of predesigned siRNA is Ambion®, Austin, Tex. Another is Qiagen® (Valencia, Calif.). An inhibitory nucleic acid that can be applied in the compositions and methods of the present invention may be any nucleic acid sequence that has been found by any source to be a validated downregulator of a protein of interest. Without undue experimentation and using the disclosure of this invention, it is understood that additional siRNAs can be designed and used to practice the methods of the invention.

The siRNA may also comprise an alteration of one or more nucleotides. Such alterations can include the addition of non-nucleotide material, such as to the end(s) of the 19 to 25 nucleotide RNA or internally (at one or more nucleotides of the RNA). In certain aspects, the RNA molecule contains a 3'-hydroxyl group. Nucleotides in the RNA molecules of the present invention can also comprise non-standard nucleotides, including non-naturally occurring nucleotides or deoxyribonucleotides. The double-stranded oligonucleotide may contain a modified backbone, for example, phosphorothioate, phosphorodithioate, or other modified backbones known in the art, or may contain non-natural internucleoside linkages. Additional modifications of siRNAs (e.g., 2'-O-methyl ribonucleotides, 2'-deoxy-2'-fluoro ribonucleotides, "universal base" nucleotides, 5-C-methyl nucleotides, one or more phosphorothioate internucleotide linkages, and inverted deoxyabasic residue incorporation) can be found in U.S. Application Publication 2004/0019001 and U.S. Pat. No. 6,673,611 (each of which is incorporated by reference in its entirety). Collectively, all such altered nucleic acids or RNAs described above are referred to as modified siRNAs.

VI. KITS AND DIAGNOSTICS

In various aspects of the invention, a kit is envisioned containing the necessary components to purify exosomes from a body fluid or tissue culture medium. In other aspects, a kit is envisioned containing the necessary components to isolate exosomes and transfect them with a therapeutic nucleic acid, therapeutic protein, or a nucleic acid encoding a therapeutic protein therein. In yet other aspects, a kit is envisioned containing the necessary components to isolate exosomes and determine the presence of a cancer cell-derived exosome-specific marker within the isolated exosomes.

The kit may comprise one or more sealed vials containing any of such components. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill. The instruction information may be in a computer readable media containing machine-readable instructions that, when executed using a computer, cause the display of a real or virtual procedure of purifying exosomes from a sample and transfecting a therapeutic nucleic acid therein, expressing a recombinant protein therein, electroporating a recombinant protein therein, or identifying a cancer cell-derived marker thereon or therein.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Material and Methods

Isolation and Purification of Exosomes.

Exosomes were purified by differential centrifugation processes, as described previously (Alvarez-Erviti et al., 2011; El-Andaloussi et al., 2012). Supernatant was collected from cells that were cultured in media containing exosomes-depleted FBS for 48 hours, and was subsequently subjected to sequential centrifugation steps for 800 g for 5 minutes, and 2000 g for 10 minutes. This resulting supernatant was then filtered using 0.2 μm filters in culture bottles, and a pellet was recovered at 28,000 g in a SW 32 Ti rotor after 2 hours of ultracentrifugation (Beckman). The supernatant was aspirated and the pellet was resuspended in PBS and subsequently ultracentrifuged for another 2 hours. The purified exosomes were then analyzed and used for experimental procedures.

Electroporation of Exosomes and Liposomes.

$1 \times 10^8$ exosomes (measured by nanosight analysis) and 1 μg of siRNA (Qiagen) or shRNA were mixed in 400 μl of electroporation buffer (1.15 mM potassium phosphate, pH 7.2, 25 mM potassium chloride, 21% Optiprep™). Exosomes were electroporated using a 4 mm cuvette using a Gene Pulser Xcell™ Electroporation System (BioRad) as previously described (Alvarez-Erviti et al., 2011; El-Andaloussi et al., 2012). A similar procedure was performed using liposomes (100 nm, purchased from Encapsula Nano Sciences). After electroporation, exosomes were treated with protease-free RNAse A (Sigma Aldrich) followed by addition of 10× concentrated RNase inhibitor (Ambion), and washed with PBS under ultracentrifugation methods, as described above.

Immunogold Labeling and Electron Microscopy.

Fixed specimens at an optimal concentration were placed onto a 300 mesh carbon/formvar coated grids and allowed to absorb to the formvar for a minimum of one minute. For immunogold staining the grids were placed into a blocking buffer for a block/permeablization step for one hour. Without rinsing, the grids were immediately placed into the primary antibody at the appropriate dilution overnight at 4° C. (monoclonal anti-CD9, 1:10, Abcam). As controls, some grids were not exposed to the primary antibody. The next day all of the grids were rinsed with PBS then floated on drops of the appropriate secondary antibody attached with 10 nm gold particles (AURION, Hatfield, Pa.) for two hours at room temperature. Grids were rinsed with PBS and were placed in 2.5% glutaraldehyde in 0.1 M phosphate buffer for 15 minutes. After rinsing in PBS and distilled water, the grids were allowed to dry and stained for contrast using uranyl acetate. The samples were viewed with a Tecnai™ Bio Twin transmission electron microscope (FEI, Hillsboro, Oreg.) and images were taken with an AMT CCD Camera (Advanced Microscopy Techniques, Danvers, Mass.).

Quantification of Alexa Fluor 647 in Cells Treated with Exosomes or Liposomes.

Exosomes isolated from BJ fibroblasts were electroporated with Alexa Fluor® 647-tagged siRNA (Qiagen, SEQ ID NO: 1), and treated with PBS, proteinase K (Qiagen, lx, 15 minutes at room temperature and ultracentrifuged with PBS for 1 hour at 4° C.), or trypsin (Life Technologies, 10×, 15 minutes at room temperature and ultracentrifuged with PBS for 1 hour at 4° C.), washed with PBS for 2 hours, and added to Panc-1 cells cultures on glass coverslips for 3 hours. The cells were then fixed by washing with cold PBS and incubating with 4% PFA at room temperature for 20 minutes. The cells were then washed with PBS, incubated with 0.05% Triton X for 10 minutes, washed with PBS and stained with Sytox® green nuclear stain (Invitrogen). The coverslips were then mounted on to glass slides by fluorescent mounting media. Focal accumulation of Alexa Fluor® 647 was visualized using a Zeiss Observer Z1 inverted microscope. The number of cells with Alexa Fluor® 647 labels were counted per visual field (400×) and the results were expressed as the percentage of cells with positive label out of the total number of cells counted per visual field.

Real-Time PCR Analyses.

RNA was retro-transcribed with MultiScribe Reverse Transcriptase (Applied Biosystems) and oligo-d(T) primers following total RNA purification with TRIzol® (Invitrogen), according to the manufacturer's directions. Real-time PCR analyses were performed on an ABI PRISM® 7300HT Sequence Detection System Instrument using SYBR® Green Master Mix (Applied Biosystems). The transcripts of interest were normalized to 18S transcript levels. Primers for $Kras^{G12D}$ were designed as described (Rachagani et al., 2011) and Kras wild-type primers were designed as described (Poliseno et al., 2010). Each measurement was performed in triplicate. Threshold cycle, the fractional cycle number at which the amount of amplified target reached a fixed threshold, was determined and expression was measured using the formula. Primer sequences are listed in Table 1.

TABLE 1

Primer sequences for RT-PCR

| Gene | Forward Primer (5'-3') | SEQ ID NO | Reverse Primer (5'-3') | SEQ ID NO |
|---|---|---|---|---|
| $KRAS^{G12D}$ | ACTTGTGGTAGTTGGAGCAGA | 3 | TTGGATCATATTCGTCCACAA | 4 |
| KRAS WT | ATTGTGAATGTTGGTGT | 5 | GAAGGTCTCAACTGAAATT | 6 |
| 18S | GTAACCCGTTGAACCCCATT | 7 | CCATCCAATCGGTAGTAGCG | 8 |

Cell Culture.

Human foreskin fibroblast (BJ) cells were cultured in DMEM supplemented with 20% exosomes-depleted FBS and 1% penicillin-streptomycin. Panc-1 and BxPC-3 cells (obtained from American Type Culture Collection [ATCC]) were cultured in RPMI 10% FBS. Panc-1 and BxPC3 cells (transfected with Luciferase promoter) were kind gifts from Dr. Thiru Arumugam, UT MDACC. Ptf1acre/+;LSL-$KRas^{G12D/+}$;$Tgfbr2^{flox/flx}$ mice (PKT) fibroblasts were isolated from the pancreas of PKT mice by mincing the isolated tumor in unsupplemented DMEM and collagenase 4 (400 units/ml) and incubating overnight. The media was then aspirated the next day after which the cells were cultured in DMEM supplemented with 20% exosomes-depleted FBS and 1% penicillin-streptomycin-ampicillin RNAi Strategies.

The $Kras^{G12D}$ siRNA sequence (GUUGGAGCUG AUGGCGUAGTT (SEQ ID NO: 1)) and $Kras^{G12D}$ shRNA sequence (CCGGGTTGGAGCT-GATGGCGTAGTTCTCGAGCTACGCCATCAGCTC-CAACTTTTT TT (SEQ ID NO: 2)) both reflect a G to A nucleotide deviation from the wild-type Kras gene sequence so as to specifically target the Glycine to Aspartate amino acid substitution in the $Kras^{G12D}$ mutation and comprise a TT nucleotide overhang to promote silencing efficiency. The central position of the nucleotide deviant in this $Kras^{G12D}$ siRNA enhances its specificity against the wild-type mRNA sequence. This was also labeled with an Alexa Fluor® 647 fluorophore at the 3' end on the sense strand to track its delivery. The siRNA was obtained from Qiagen (Cat. No. 1027424). For use as a scrambled siRNA, All Stars Negative siRNA was obtained from Qiagen (Cat. No. 1027287). An shRNA targeting GFP was used as a scrambled shRNA.

Exosomes Transfection.

For in vitro transfection using exosomes and liposomes, both were electroporated and washed with PBS as described above, and 200,000 cells in a 6-well plate were treated with exosomes and liposomes for the required time as described for each assay and subsequently washed with PBS and used for further analysis.

Growth Kinetics and Apoptosis Assays.

Panc-1 and BxPC-3 cells were seeded in a 6-well plate ($2.5 \times 10^5$) and allowed to grow for 12 hours, after which they were treated with exosomes electroporated with si/shRNA. Subsequently, every 24 hours, the number of viable cells was counted by trypsinizing the cells and mixing with trypan blue prior to cell counting using a hemocytometer. This process was repeated every 24 hours, until 84 hours post seeding. Apoptosis by TUNEL was assessed using In Situ Cell Death Kit, TMR red (Roche), according to the manufacturer's directions. The cells were fixed as described above, and Sytox® green (Invitrogen, 1:10,000 in PBS for 10 minutes at room temperature) was used to stain the nuclei. Images were taken using a Zeiss LSM 510 confocal microscope, and quantified by counting the number of cells with TUNEL positivity per visual field (400×) and the results were expressed as the percentage of cells with positive label out of the total number of cells counted per visual field.

Western Blot.

To deduce the protein expression of cells after treatment with exosomes after 24 hours, Panc-1 cells were harvested in RIPA buffer and protein lysates were normalized using Bradford quantification. 40 µg of lysates were loaded onto acrylamide gels for electrophoretic separation of proteins under denaturing conditions and transferred onto PVDF membranes (ImmobilonP) by wet electrophoretic transfer. The membranes were then blocked for 1 hour at room temperature with 5% non-fat dry milk in PBS/0.05% Tween-20 and incubated overnight at 4° C. with the following primary antibodies: anti-rabbit p-Erk-p44/p42 MAPK (Erk1/2) (Thr202/Tyr 204) (Cell Signaling, 4376, 1:1000), anti-rabbit p-AKT-anti AKT1 (phospho 5473) (Abcam, ab81283, 1:5000), anti-rabbit (3-actin (Cell Signaling, 4967, 1:1000). Secondary antibodies were incubated for 1 hour at room temperature. Washes after antibody incubations were done on an orbital shaker, three times at 15 min intervals, with 1×PBS 0.05% Tween®-20. Membranes were developed with chemiluminescent reagents from Pierce, according to the manufacturer's directions and chemiluminescence captured on film.

Northern Blot.

Urea/acrylamide 15% gels were used to load 20 µg of sucrose gradient exosomal RNA together with 1×RNA loading dye for 2 min at 95° C., followed by 2 min on ice. MicroRNA marker was used according to manufacturer's instructions (N2102, New England BioLabs). Electrophoresis was conducted at 4° C. for 3 h using 1×TBE. Transfer was performed using Whatman blotting papers and the BrightStar®-Plus Positively Charged Nylon Membrane (Ambion) for 2 h at 4° C. with 0.5×TBE. The RNA was cross-linked to the membrane using a UV transilluminator for 20 min Membranes were pre-hybridized by rotating for 1 h at 42° C. in Ambion's ULTRAhyb®-Oligo hybridization solution (Ambion). The probes were then thawed on ice and 150 ng were added per mL of hybridization buffer after a 5 min incubation at 95° C., after which membranes were left in rotation overnight at 42° C. The following washes steps were done: 2×SSPE/0.5% SDS—twice for 15 min; 0.2× SSPE/0.5% SDS—twice for 30 min, and 2×SSPE—5 min. These initial washing steps were followed by more washes, and then the blots were developed using the BrightStar® BioDetect™ Kit according to the manufacturer's instructions (Ambion). The blots were exposed overnight with four stacked films. Alexa Fluor® 647 fluorophore was detected directly using LI-COR Biosciences Odyssey Infrared Imaging System.

Immunocytochemistry.

Cells were plated onto coverslips and treated for 3 h with either exosomes or liposomes electroporated with Kras$^{G12D}$ siRNA. The coverslips were then washed with cold 1×PBS and cells fixed for 20 min at room temperature with 4% paraformaldehyde, permeabilized for 10 min at room temperature with 0.5% Triton™ X-100 in PBS, and the nucleus was stained with Sytox green resuspended in 2% BSA. Images were obtained using a Zeiss LSM510 Upright Confocal System using the recycle tool to maintain identical settings. Aggregated exosomes containing Alexa Fluor® 647-tagged siRNA allowed for the visualization of focal accumulation of label detectable by confocal microscopy. For data analysis, images were selected from a pool drawn from at least two independent experiments. The number of cells with Alexa Fluor 647 labels were counted per visual field (×400) and the results were expressed as the percentage of cells with positive label out of the total number of cells counted per visual field.

Mice and Imaging.

Female athymic nu/nu mice (Charles Rivers) between 4-6 weeks of age were housed in individually ventilated cages on a 12 h light-dark cycle at 21-23° C. and 40%-60% humidity. Mice were allowed free access to an irradiated diet and sterilized water. Under general anesthesia, Panc-1 or BXPC-3 cells ($10^6$, resuspended in 10 μl PBS) were injected into the tail of the pancreas using a 27-gauge syringe. For detection of luciferase expression, the mice were injected i.p. with 100 mg/kg luciferin (200 μl of 10 mg/ml in PBS) 12-15 min before imaging, anesthetized with isofluorane, and imaged using IVIS (Xenogen Spectrum). For orthotopic tumor analyses, Living Image version 4.4 (Caliper Life Sciences) was used to quantify all tumor calculations. A circular region of interest (ROI) around the pancreas and tumor was defined, and set as a standard to compare all the images within the same experimental group. In addition, exposure conditions (time, aperture, stage position, binning) were kept identical for all measurements in all experimental groups. Subsequent tumor measurements (p/sec/cm$^2$/sr) were then obtained under the same conditions for all experimental groups. The mice were imaged regularly and randomly divided into groups for treatments. Mice received 2×10$^8$ exosomes or liposomes i.p. in 100 μl volume of PBS every other day. Exosomes or liposomes were electroporated with 2 μg of siRNA or shRNA and washed with PBS prior to injection. When using PKT (Ptf1acre/+;LSL-KrasG12D/+;Tgfbr2flox/flox) (Özdemir et al., 2014) genetically engineered mice, exosomes treatment was initiated at 33 days of age, when mice present with PaNIN and PDAC lesions. All animal procedures were reviewed and approved by the Institute for Animal Care and Use Committee at UT MDACC.

Macrophage Clearance.

Immunocompetent adult mice were injected i.p. with either exosomes or liposomes containing Alexa Fluor® 647-tagged siRNA. The blood of these mice was collected 12 h post-injection and processed for flow cytometry analyses. RBCs were depleted using ACK lysis buffer (Invitrogen), and the peripheral cells were blocked with FC block (1:1000, BD Pharmingen), stained with Sytox green (1:200, Invitrogen) and CD11b (1:200, BD Pharmingen, PerCP/Cye 5.5) antibodies for 30 min, washed with PBS, and analyzed using a LSR Fortessa™ X-20 cell analyser. Pre-incubation of mouse cell suspensions with FC Block for several minutes, prior to staining with specific antibodies assures that any observed staining is due to the interaction of the antigen-binding portion of the antibody with an antigen on the cell surface.

Histology, Histopathology, and Immunohistochemistry.

Tissues were fixed in formalin and processed for paraffin embedding. Tissue sections of 5 μm thickness were cut and stained for hematoxylin and eosin (H&E) and Masson's trichrome (MTS) (Leica). For histopathological scoring, H&E stained slides were scored based on the morphological stages of pancreas cancer: Normal, pancreatic intraepithelial neoplasia (PaNIN) and pancreatic ductal adenocarcinoma (PDAC). For each tissue section, a percentage score for each of the three stages (Normal, PaNIN, PDAC) was obtained manually in a blinded fashion by experts in pancreas histology, which was then averaged to give an overall score out of 100 for each cohort. An average of these percentage scores was then taken for each mouse in the respective cohorts.

For the analysis of fibrosis in mice, eight 200× visual fields were randomly selected for each MTS stained pancreas section and fibrosis was manually evaluated by a grid intersection analysis using Adobe Photoshop. For each picture evaluation, a grid of a 100 squares was overlapped on each picture, and each intersection was counted for blue (fibrotic area) and purple/red (non-fibrotic area). A percentage score was then obtained for each tissue section. Tissue sections were also subjected to antigen retrieval (15 min in 10 nM citrate buffer at pH 6 and 98° C.) prior to immunostaining. The tissue sections were incubated with 4% CWFS gelatin (Aurion) in either TBS or PBS, 1 h prior to overnight incubation with the primary antibodies. The following primary antibodies were used for staining: anti-rabbit p-Erk-p44/p42 MAPK (Erk1/2) (Thr202/Tyr 204) (Cell Signaling, 4376, 1:400), anti-rabbit p-AKT-Anti AKT1 (phospho S473) (Abcam, ab81283, 1:100), anti-rabbit Ki-67 (Thermo Scientific, RM-9106-S, 1:400). For all staining, sections were incubated with biotinylated goat anti-rabbit and streptavidin HRP (Biocare Medical), each for 10 min, and counterstained with haematoxylin. DAB positivity was analyzed. Ki-67 staining was quantified by counting the number of positively stained nuclei per visual field (400×), whereas p-Erk and p-AKT staining were quantified with ImageJ by designing a macros to include only the dark stained portion of the picture, which was then considered as a positive stained area for the respective antibodies. This was performed in eight 200× pictures per tissue section, and an average of the positive score was obtained for each tissue section. TUNEL assay was performed using the In situ cell death detection kit, TMR Red (Roche), according to the manufacturer's directions. Alexa 647 was detected on frozen tissue sections by staining the nuclei of the tissue with Sytox® green (1:10,000 in PBS for 10 min). Images were taken using a Zeiss LSM 510 confocal microscope, and quantified by counting the number of cells with TUNEL positivity per visual field (×400) and the results were expressed as the percentage of cells with positive label out of the total number of cells counted per visual field.

Statistical Analyses.

Statistical analyses used are detailed in the figure legends. One-way ANOVA or unpaired two-tailed student's t-test were used to establish statistical significance using GraphPad Prism (GraphPad Software). For survival analyses, Kaplan-Meier plots were drawn and statistical differences evaluated using the log rank Mantel-Cox test. A p value <0.05 was considered statistically significant.

Example 1—Anti-Tumor Properties of Inhibitory RNA-Containing Exosomes siRNA and shRNA constructs were designed to specifically target Kras$^{G12D}$. The siRNA sequence (GUUG-GAGCUGAUGGCGUAGTT; SEQ ID NO: 1) reflects a G to A nucleotide deviation from the wild-type Kras gene sequence (underlined and bold) so as to specifically target the Glycine to Aspartate amino acid substitution in the Kras$^{G12D}$ mutation found in cell lines and animal models, and a TT nucleotide overhang (underlined) to promote silencing efficiency (Rejiba et al., 2007; Ma et al., 2004; Du et al., 2005). The central position of the nucleotide deviant in this Kras$^{G12D}$ siRNA enhances its specificity against the wild-type mRNA sequence (Du et al., 2005). The shRNA sequence (SEQ ID NO: 2) was designed to contain the specific G to A nucleotide deviation in the seed sequence to promote the specific targeting of Kras$^{G12D}$ mRNA. The siRNA oligonucleotides for Kras$^{G12D}$ were also labeled with an Alexa Fluor® 647 fluorophore to track their delivery (FIG. 4A).

Figure 1B:
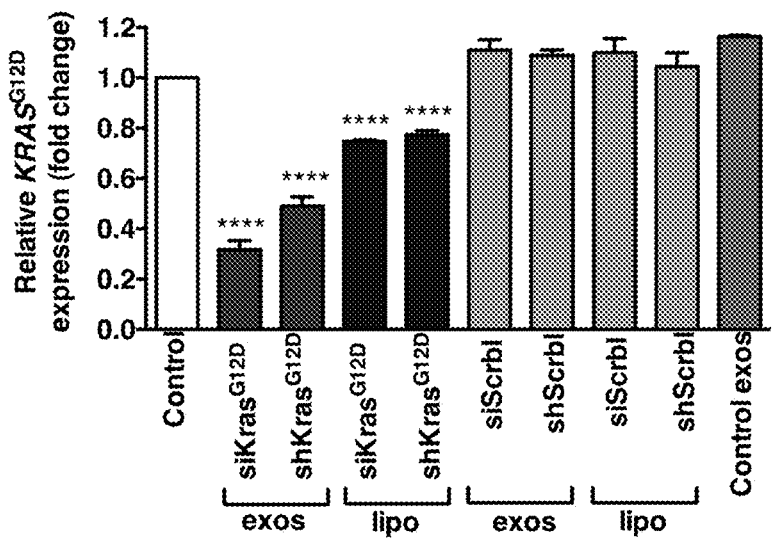
Figure 1C:
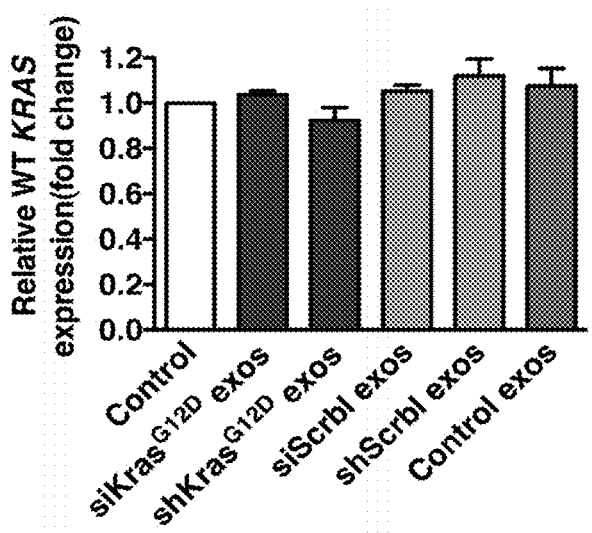
Figure 1D:
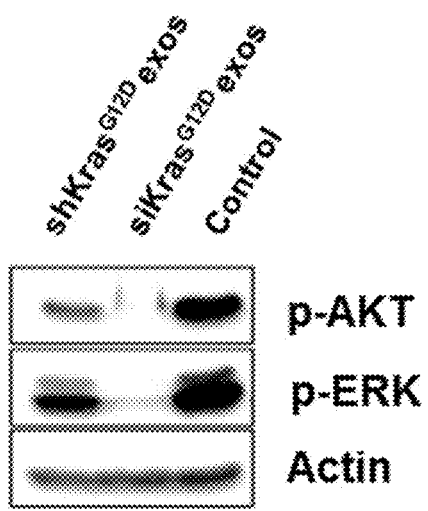
Figure 1E:
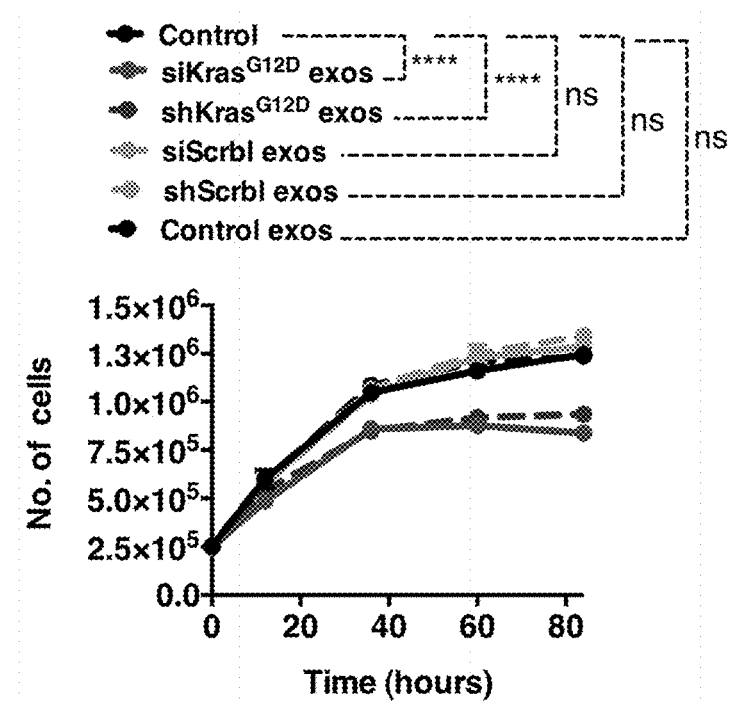
Figure 1F:
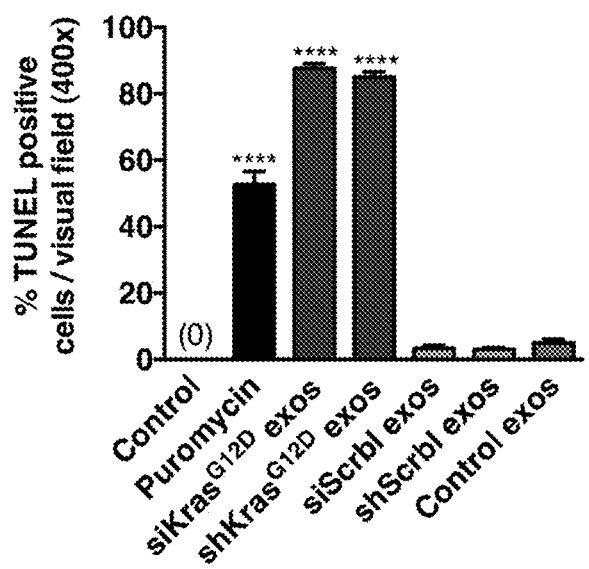
Figure 4A:
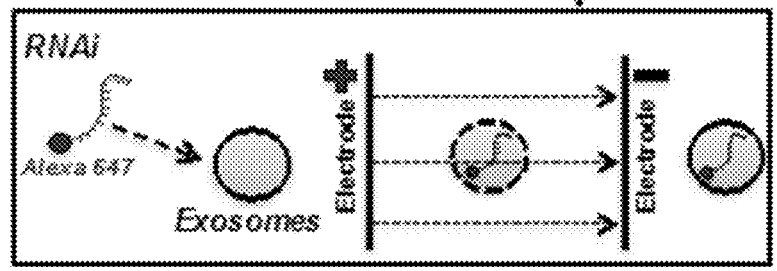
FIGS. 4A-I. Specific Kras$^{G12D}$ targeting using exosomes.
Figure 4B:
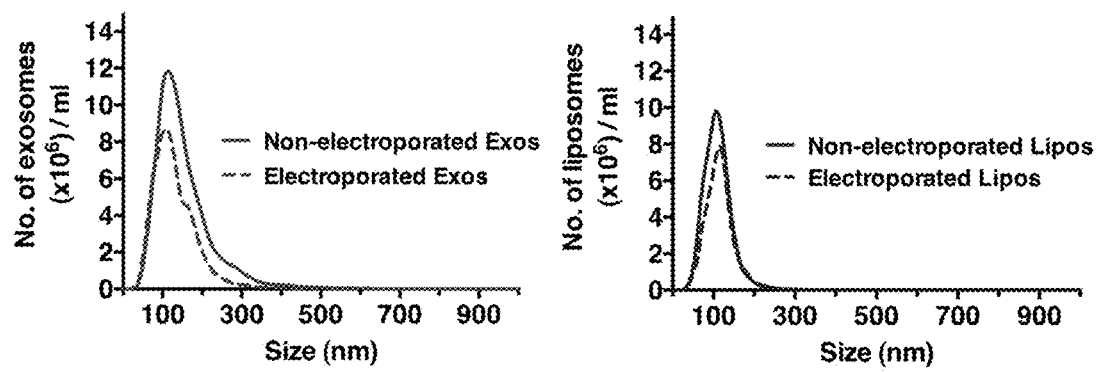
Figure 4C:
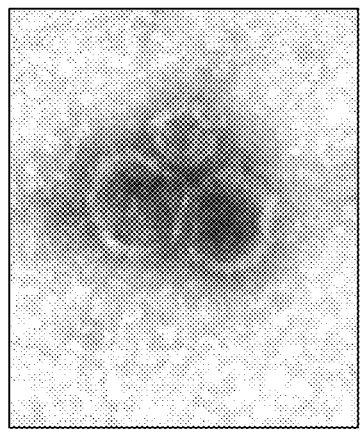
Figure 4D:
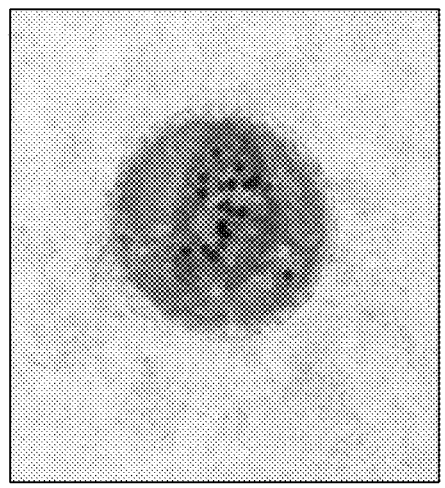
Figure 4E:
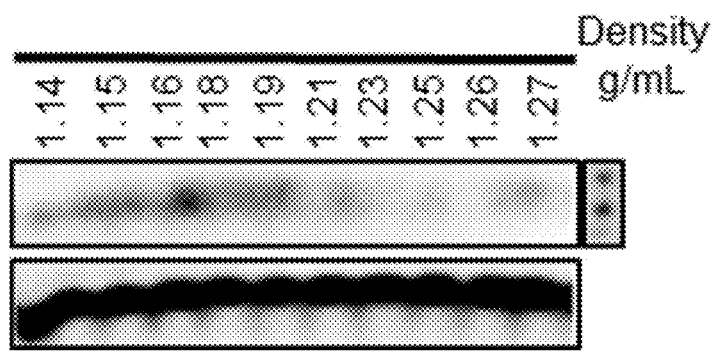
Figure 4F:
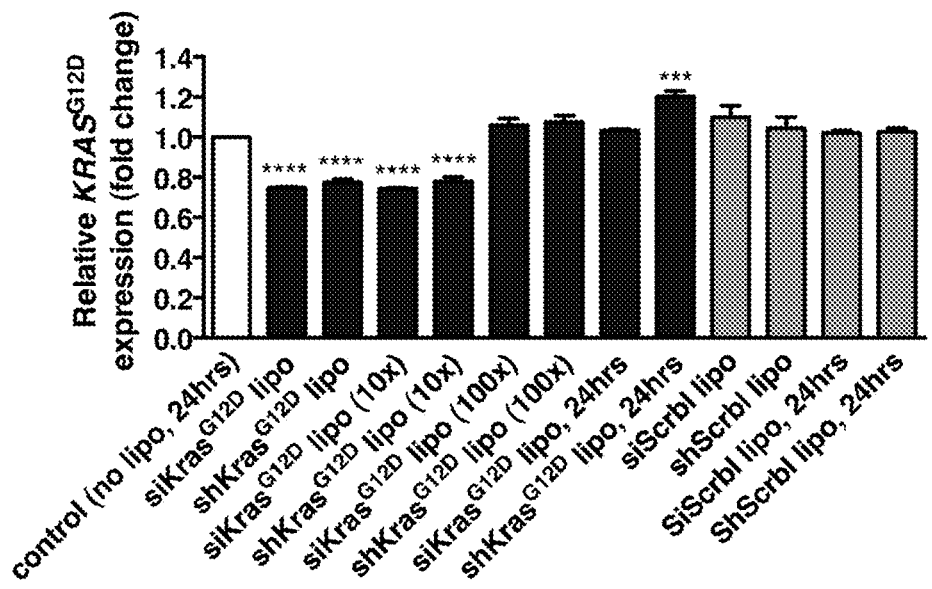
Figure 4G:
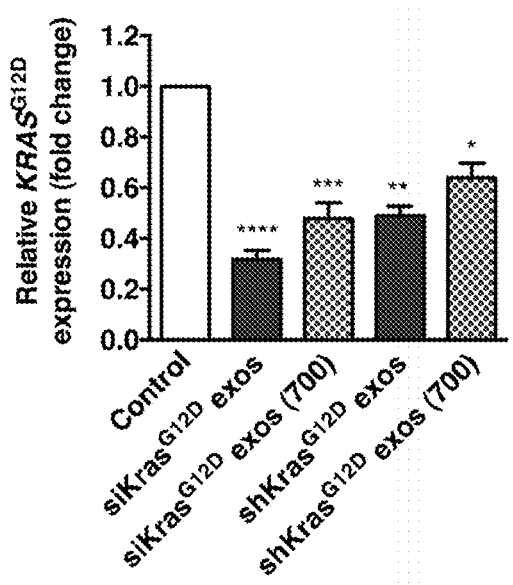
Figure 4H:
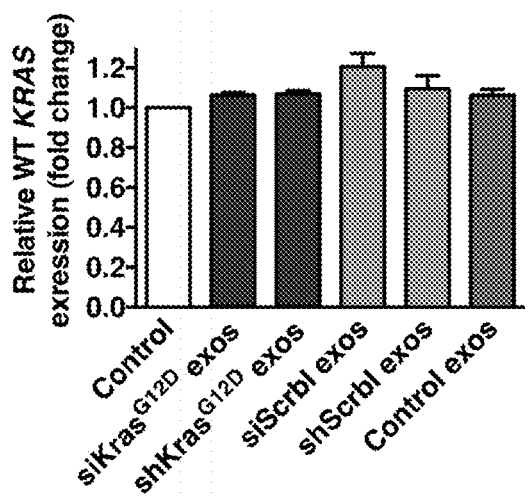
Figure 4I:
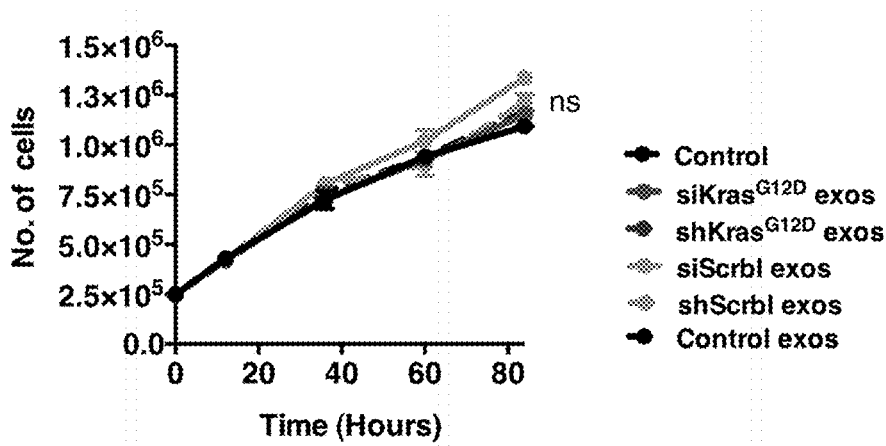

New electroporation methods were developed and optimized to insert shRNA and siRNA constructs into exosomes (siKras$^{G12D}$/shKras$^{G12D}$ exos) without functionally damaging exosomes (FIGS. 4A-C). To this end, exosomes were isolated from human foreskin fibroblasts (BJ fibroblasts) using established ultracentrifugation methods (Kahlert et al., 2014). The purity and homogeneity (80-150 nm diameter particles) of the exosomes was validated by Nanosight™ measurements (FIG. 4B), transmission electron microscopy (FIG. 4C), and CD9 immunogold labeling (FIG. 4D). Sucrose gradient ultracentrifugation and northern blot also validated the purity of the exosomes extraction as well as the presence of Alexa Fluor 647 within the exosomes (FIG. 4E). Scrambled siRNA and shRNA containing exosomes (siScrb1/shScrb1 exos), scrambled siRNA and shRNA containing liposomes (siScrb1/shScrb1), and Kras$^{G12D}$ siRNA/shRNA containing liposomes (siKras$^{G12D}$/shKras$^{G12D}$ lipos) were also generated. Tumorigenic human pancreas Panc-1 (Kras$^{asp12}$ (Rejiba et al., 2007; Sun et al., 2001)) cells were incubated with exosomes and liposomes containing Alexa Fluor® 647-labeled siRNA for 3 h, and immunofluorescence imaging revealed a significant number of focal accumulation of label in exosomes treated cells vs. liposome treated cells (FIG. 1A). Treatment of exosomes with proteinase K or trypsin diminished cellular staining while proteinase K or trypsin treatment of liposomes maintained low cellular staining, supporting that exosomes surface proteins enhance delivery of the labeled siRNA into the cells (FIG. 1A). siKras$^{G12D}$ and shKras$^{G12D}$ exos treatment reduced Kras$^{G12D}$ mRNA levels (~70% and ~50% reduction, respectively) in Panc-1 cells compared to siScrb1/shScrb1 exos or non-electroporated (control, without RNAi payloads) exos (FIG. 1B). siKras$^{G12D}$ and shKras$^{G12D}$ lipos treatment also reduced Kras$^{G12D}$ mRNA levels (~20% reduction each) in Panc-1 cells compared to siScr1/shScrb1 lipos (FIG. 1B). The specific knockdown of the mutant Kras$^{G12D}$ transcripts was measured using quantitative real-time PCR (qPCR) with primers that specifically amplify Kras$^{G12D}$ but not the wild-type Kras (Table 1), and siKras$^{G12D}$ and shKras$^{G12D}$ exos treatment did not lower wild-type Kras mRNA levels, supporting the Kras$^{G12D}$ mRNA specific targeting with the present methodology (FIG. 1C). The efficacy of the knockdown of mutant Kras$^{G12D}$ transcripts was greater when using exosomes instead of liposomes (FIG. 1B), possibly reflecting the impaired delivery of liposomes compared to exosomes (FIG. 1A). Increasing the concentration of siKras$^{G12D}$ and shKras$^{G12D}$ lipos or the incubation time of liposomes with Panc-1 cells did not improve the efficiency of Kras$^{G12D}$ mRNA targeting (FIG. 4F), supporting superior intrinsic properties of exosomes over liposomes in delivery of RNAi cargo for effective mRNA targeting. Further experimental optimizations revealed that a ratio of approximately 400 exosomes per Panc-1 cell was superior to suppress Kras$^{G12D}$ transcript levels than a ratio of 700 exosomes per Panc-1 cell (FIG. 4G). Finally, BxPC3 pancreatic cancer cells that do not harbor Kras$^{G12D}$ mutation (Kras$^{wt,Gly}$ (Sun et al., 2001)) were used as control, and siKras$^{G12D}$ and shKras$^{G12D}$ exos treatment did not suppress wild-type Kras expression in these cells (FIG. 4H), further supporting the specificity of the Kras$^{G12D}$ siRNA and shRNA constructs to suppress oncogenic Kras mRNA levels. Oncogenic Kras suppression in Panc-1 cells treated with siKras$^{G12D}$ or shKras$^{G12D}$ exos was associated with a decrease in phosphorylated-ERK and phosphorylated-AKT protein levels, supporting that downstream signaling of oncogenic Kras was attenuated (FIG. 1D). In contrast with Panc-1 cells with treated shScrb1 exos or non-electroporated control exos, the proliferation of siKras$^{G12D}$ or shKras$^{G12D}$ exos-incubated Panc-1 cells was significantly reduced (FIG. 1E). In contrast, proliferation of BxPC3 cells was unaffected by siKras$^{G12D}$ or shKras$^{G12D}$ exos treatment (FIG. 4I). Finally, reduced proliferation of siKras$^{G12D}$ or shKras$^{G12D}$ exos-treated Panc-1 cells was associated with enhanced apoptosis measured by TUNEL assay, corroborating the reduced proliferation of these cells when treated with siKras$^{G12D}$ or shKras$^{G12D}$ exos (FIG. 1E).

Figure 2A:
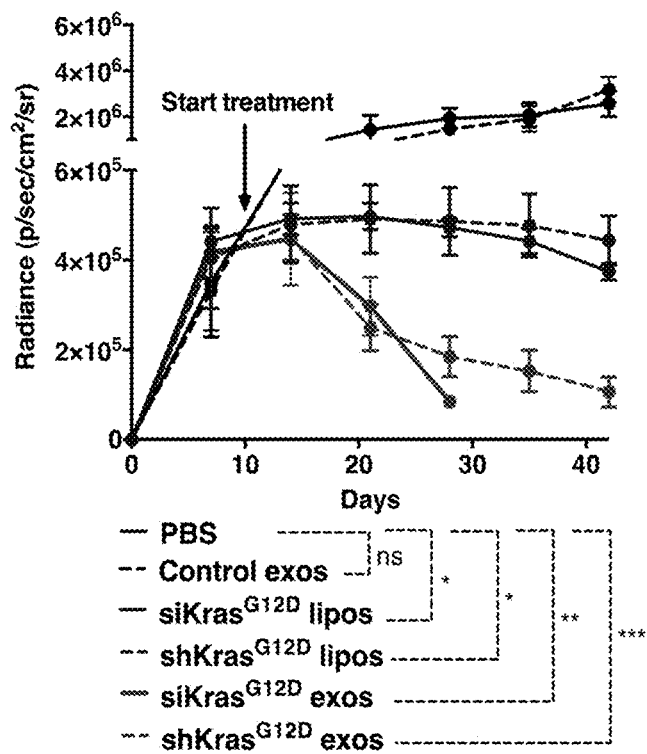
FIGS. 2A-G. Treatment with exosomes containing $si/shKras^{G12D}$ cargo results in sustained Panc-1 orthotopic tumor regression.
Figure 2B:
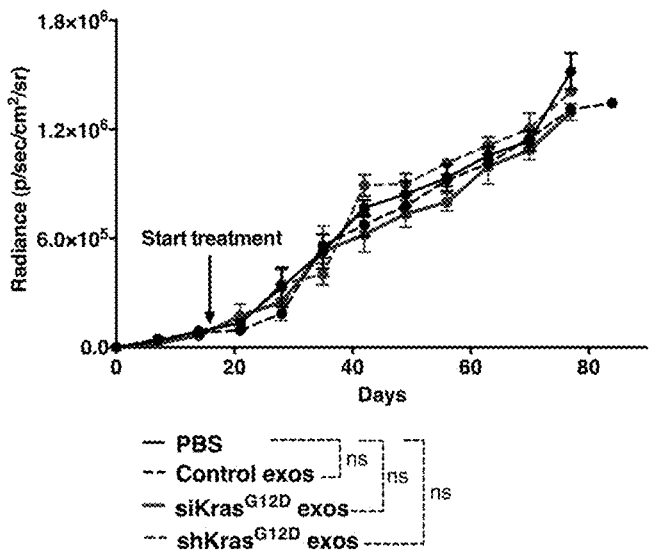
Figure 2C:
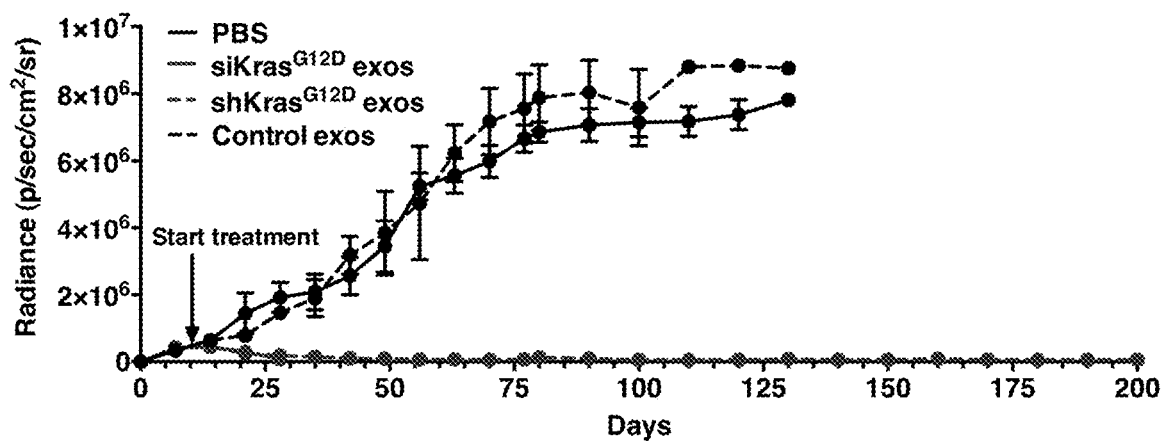
Figure 2D:
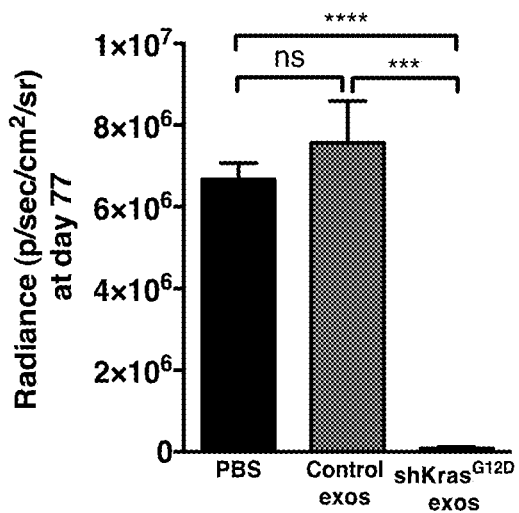
Figure 2E:
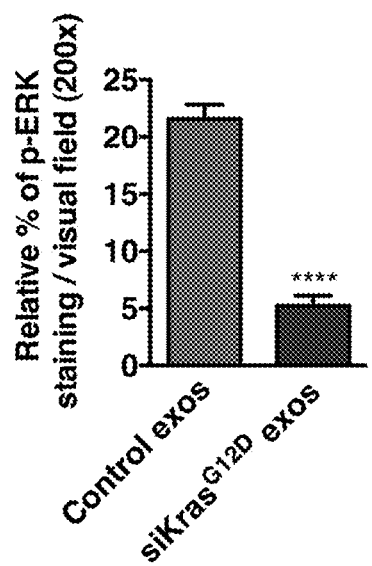
Figure 2F:
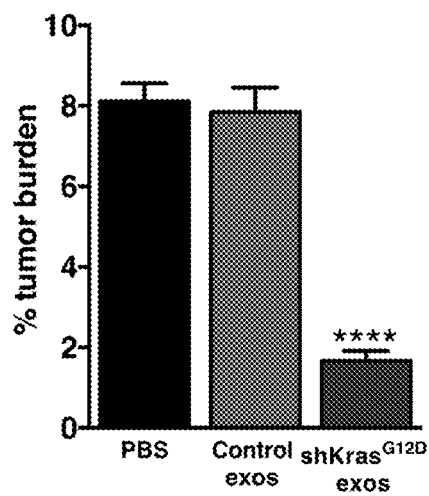
Figure 2G:
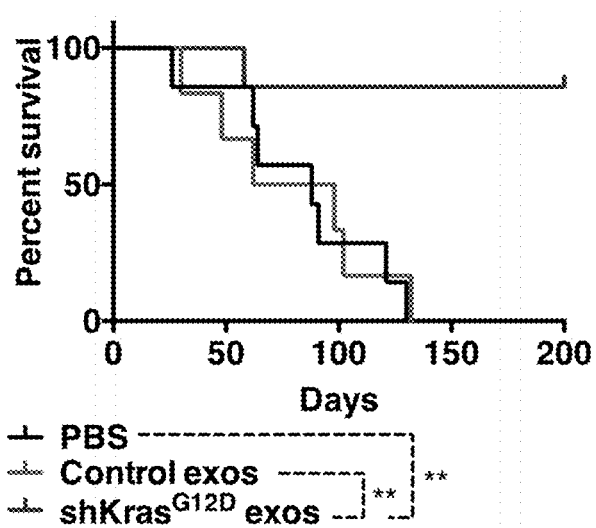
Figure 5A:
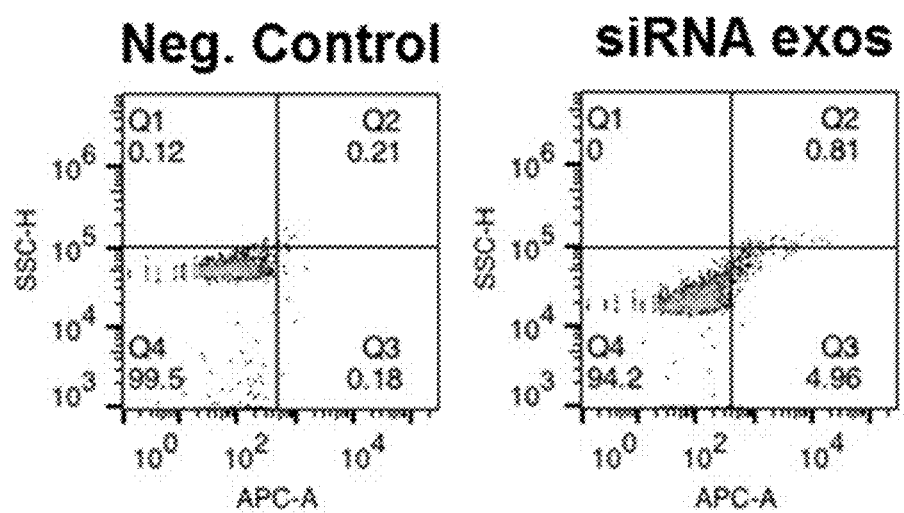
FIGS. 5A-D. Kras$^{G12D}$ RNAi containing exosomes suppress Panc-1 orthotopic tumor growth.
Figure 5B:
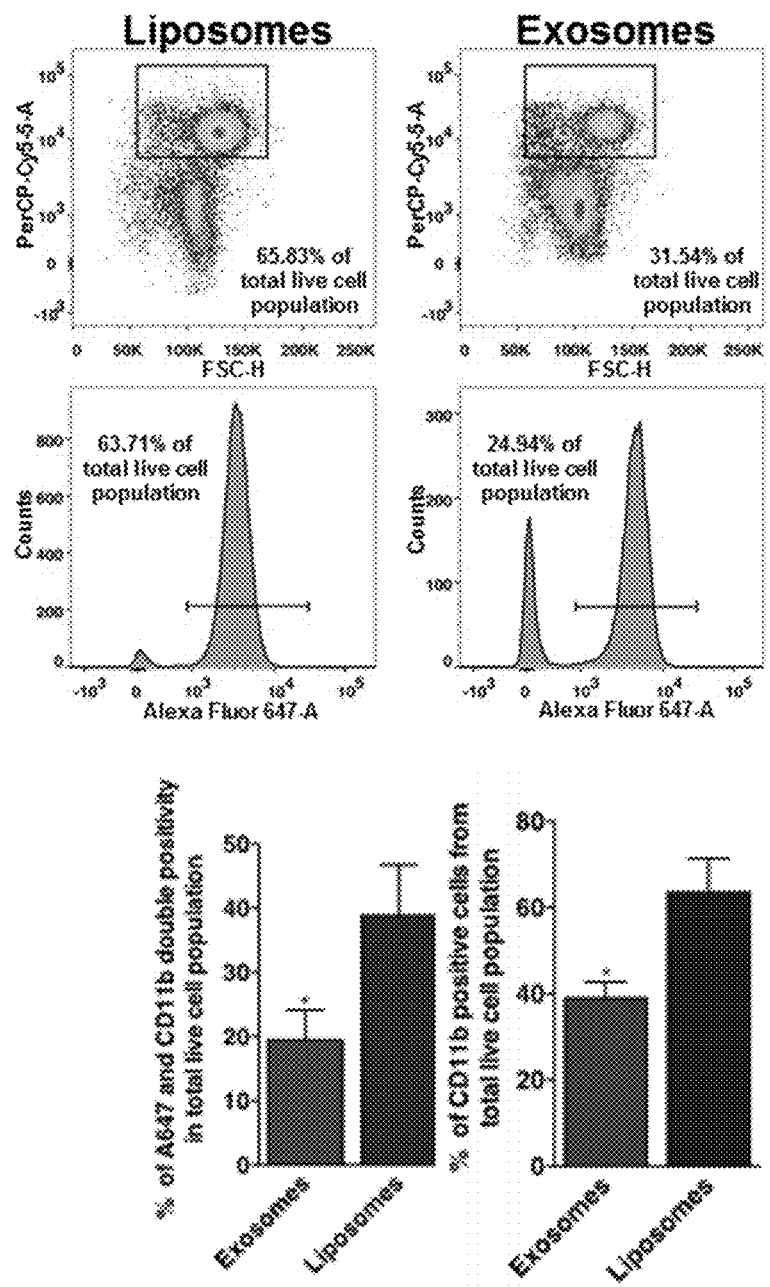
Figure 5C:
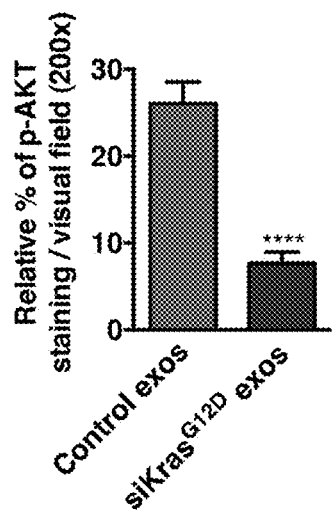
Figure 5D:
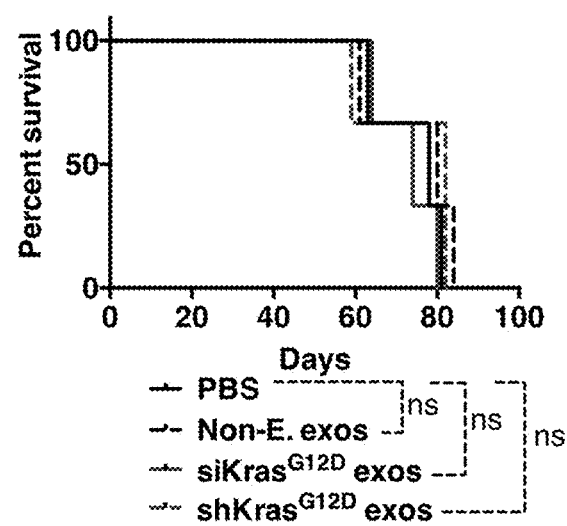
Figure 6A:
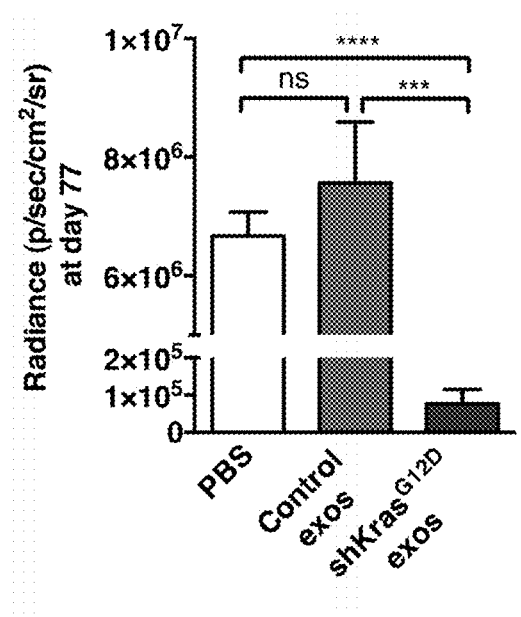
FIGS. 6A-B. Panc-1 tumor progression.
Figure 6B:
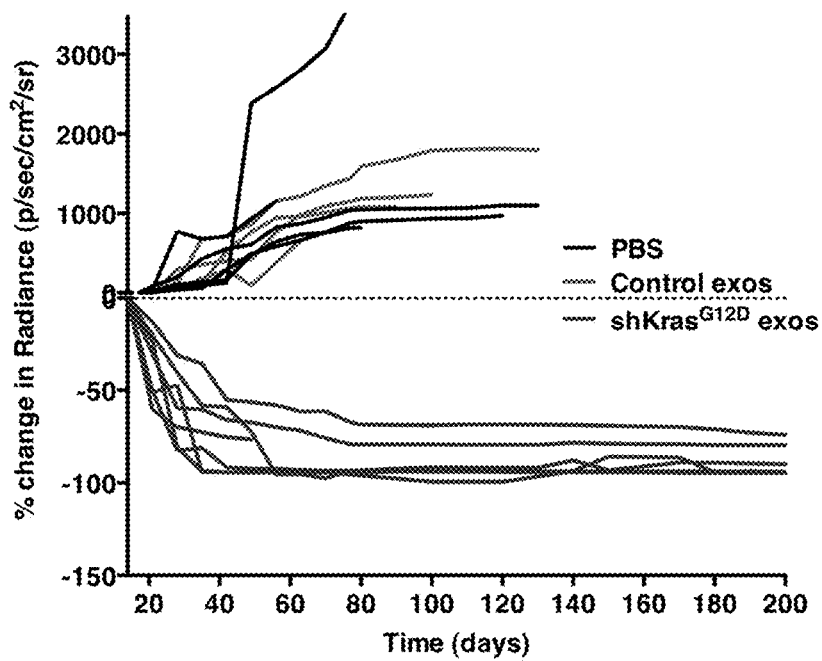

In vitro experiments suggested that siKras$^{G12D}$ or shKras$^{G12D}$ exos specifically targeted oncogenic Kras and induced apoptosis via impaired downstream oncogenic Kras signaling. Next, the capacity of exosomes containing siKras$^{G12D}$ or shKras$^{G12D}$ to silence Kras$^{G12D}$ expression in pancreas tumors was explored. Focal accumulations of Alexa Fluor 647-labeled siRNA from exosomes injected intra-peritoneally in mice were detected in pancreas tissue 24 h post-injection. Further, exosomes containing Alexa Fluor 647-labeled siRNA were detected using flow cytometry in the serum of mice 24 h post-i.p. injection (FIG. 5A). These results suggest that exosomes administered i.p. in mice enter systemic circulation and reach the pancreas. After confirming that a significant number of exosomes approximate the parenchyma of the pancreas, $1\times10^6$ luciferase-expressing Panc-1 human pancreatic (Panc-1-luc) cells were orthotopically implanted in nude mice, which were treated with i.p. injections of exosomes or liposomes. Ten days post injection of cancer cells, all mice presented with detectable tumors by bioluminescent imaging and ranged between $1\times10^5$ and $1\times10^6$ p/sec/cm$^2$/sr radiance. The mice were randomized and subjected to repeated $1\times10^6$ exosomes or liposomes i.p. injections every 48 h. Of note, the liposomes used were 100 nm in size, approximating the size range of exosomes, and injected in similar concentrations and dosages as exosomes. Cohorts of mice were also injected with PBS vehicle and non-electroporated exosomes. While the tumors of mice administered PBS or non-electroporated exosomes grew at an exponential rate, the tumors of mice treated with siKras$^{G12D}$ or shKras$^{G12D}$ exos were significantly reduced to baseline bioluminescent detection levels 30 days post-initiation of treatment (FIG. 2A). Tumor growth was also blunted in mice treated with siKras$^{G12D}$ or shKras$^{G12D}$ lipos, however to a much less extent than when exosomes were used (FIG. 2A). Also, increased macrophage clearance of liposomes compared to exosomes was detected, wherein a greater number of macrophages containing Alexa Fluor 647-labeled RNAi was noted in systemic circulation of mice treated with labeled-RNAi containing liposomes compared to mice treated with labeled-RNAi containing exosomes (FIG. 5A). Of note, siKras$^{G12D}$ or shKras$^{G12D}$ exos did not impact orthotopic BxPC3 tumor growth (FIG. 2B) nor overall survival (FIG. 5D), supporting the specific anti-tumor effect of siKras$^{G12D}$ or shKras$^{G12D}$ exos treatment on cancer cells harboring Kras$^{G12D}$ mutation. Histopathological findings in day-matched PBS and siKras$^{G12D}$ exos treated mice as early as 26 days post-cancer cell injection showed significant reduction of pancreas cancer disease following brief (16 day) siKras$^{G12D}$ exos treatment. At day 77 post-cancer cell injection, PBS-treated control mice showed extensive tumor burden assayed by bioluminescence imaging, while shKras$^{G12D}$ exos-treated mice tumor burden was reduced to nearly undetectable levels (FIG. 2C, FIG. 6B). Long-term treatments were carried out using shKras$^{G12D}$ exos, and while all PBS and control exos treated Panc-1 tumor-bearing mice required euthanasia based on moribund criteria or excessive tumor burden 130 days post-cancer cell injection, all mice treated with shKras$^{G12D}$ exos were healthy and presented minimal tumor burden as detected by bioluminescent imaging 200 days post-cancer cell injection (FIG. 2D, FIG. 6B). Immunolabeling of tumors for p-ERK (FIG. 2E) and p-AKT (FIG. 5C) also revealed suppressed Kras signaling in tumors of mice treated with shKras$^{G12D}$ exos compared to control (PBS-treated) mice. These data indicated that exosomes delivery of shKras$^{G12D}$ offered a reduction of tumor growth and maintained suppression of tumor growth. Histopathological analyses of the pancreas at these time points showed advanced tumors involving all of the pancreas in PBS-treated mice (130 days), in contrast with small tumor foci with the vast majority of the pancreas uninvolved in shKras$^{G12D}$ exos-treated mice (FIG. 2D). Percent tumor burden (based on pancreas mass at experimental endpoint) (FIG. 2F) and survival (FIG. 2G) were also vastly improved in Panc-1 tumor bearing mice following shKras$^{G12D}$ exos, with all control mice succumbing to pancreas tumor burden. Mice were euthanized when reaching moribund state in the PBS and control exos-treated groups at 88-130 days post-cancer cell implantation, whereas nearly all mice were well and alive at 200 days post-cancer cell implantation in the shKras$^{G12D}$ exos-treated group (one mouse was found dead at day 59, however necropsy analyses revealed minimal tumor burden in this mouse and necropsy analyses supported death unrelated to cancer).

Figure 3A:
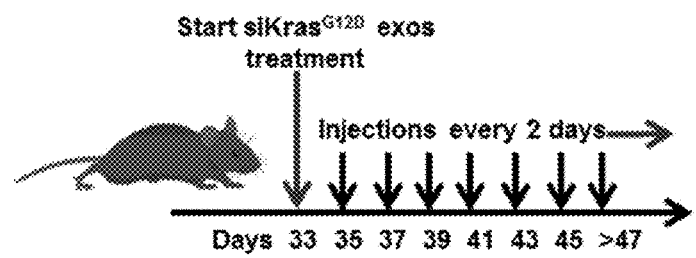
FIGS. 3A-G. Injection of exosomes packaged with $Kras^{G12D}$ siRNA and shRNA induces slower tumor progression and increased survival in PKT mice.
Figure 3B:
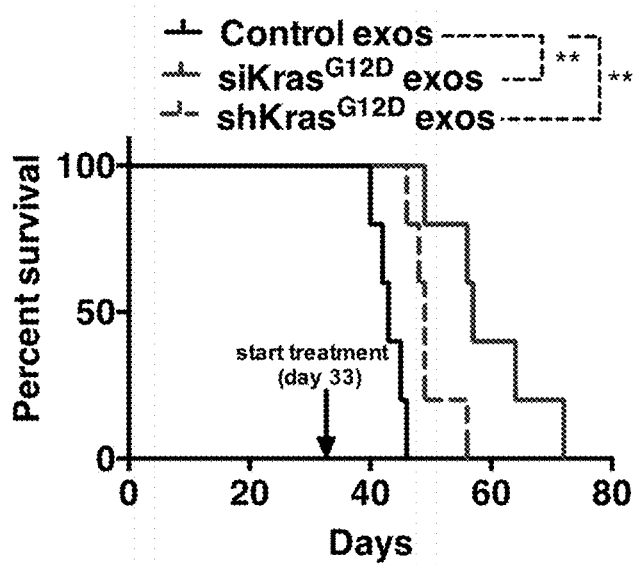
Figure 3C:
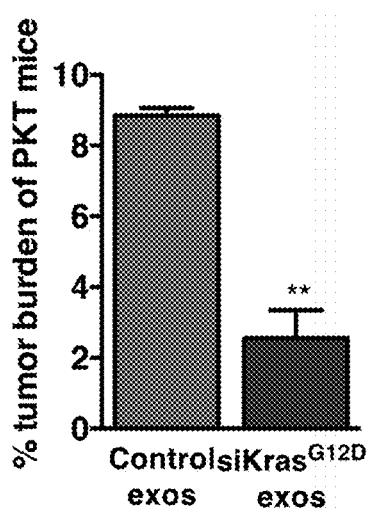
Figure 3D:
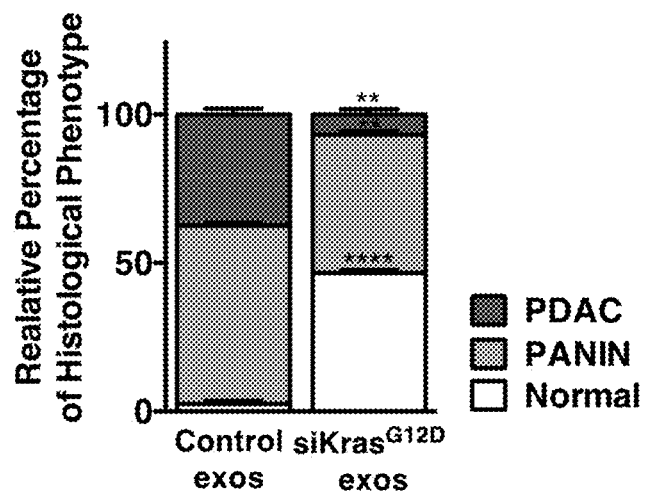
Figure 3E:
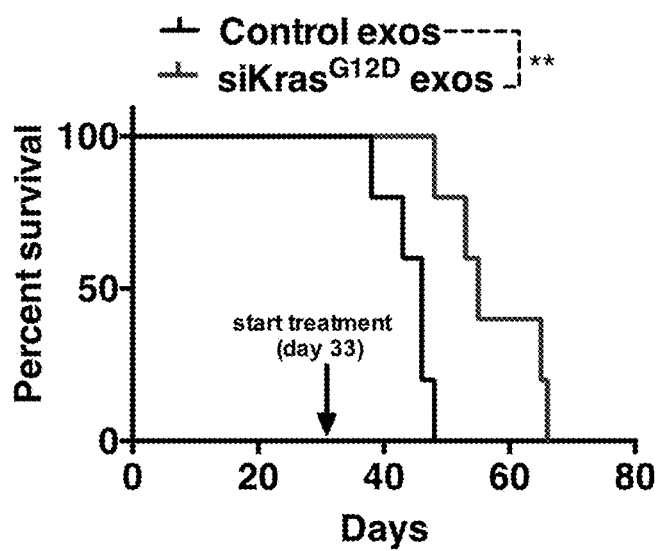
Figure 3F:
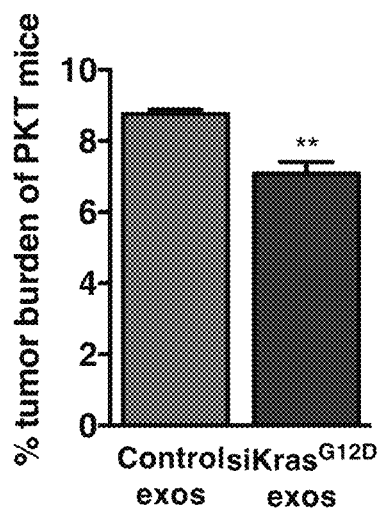
Figure 3G:
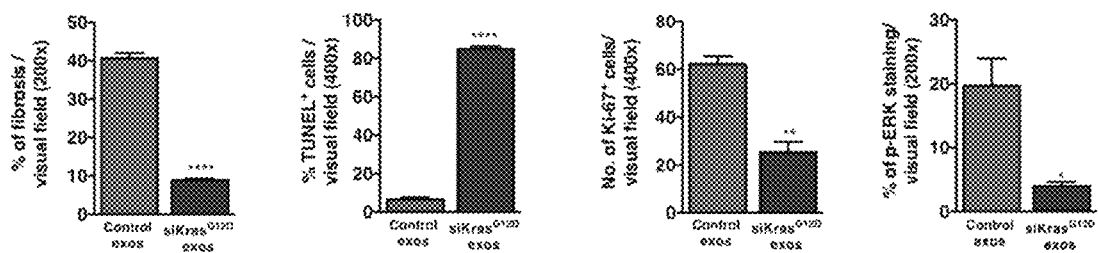
Figure 7A:
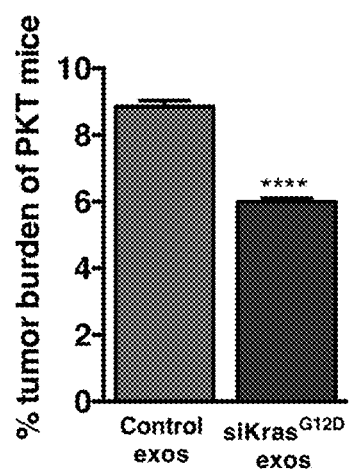
FIGS. 7A-D. Histological analyses Kras$^{G12D}$ RNAi exos treated PKT mice.
Figure 7B:
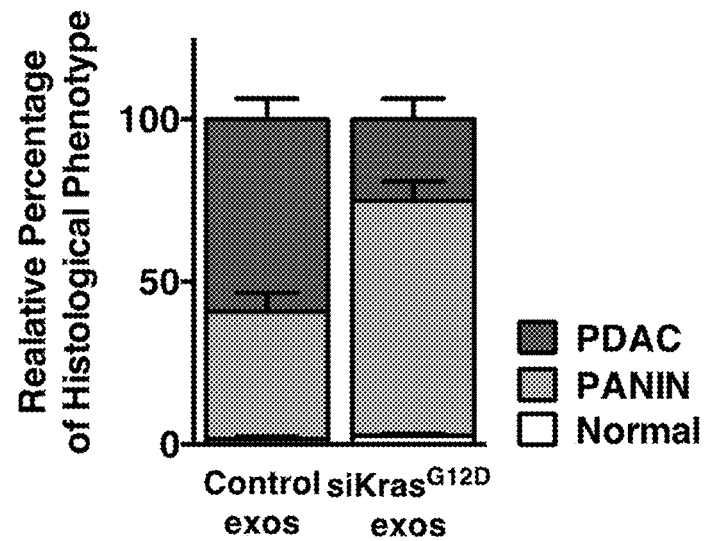
Figure 7C:
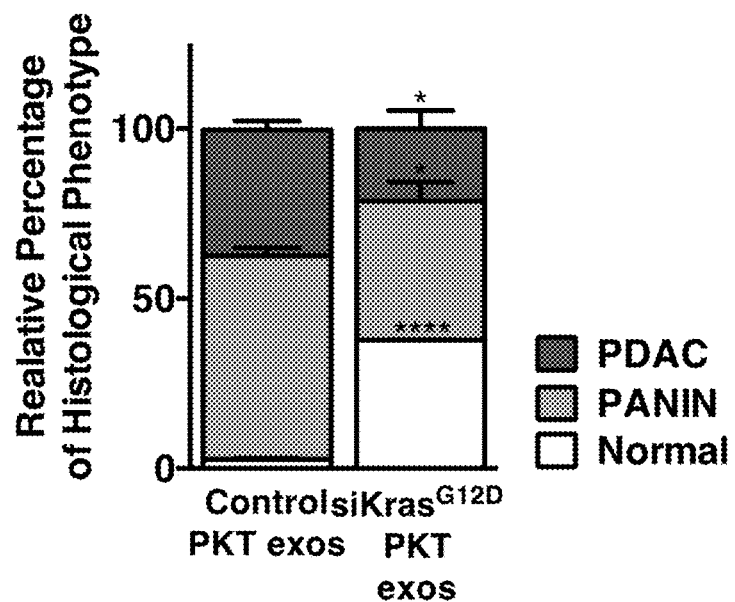
Figure 7D:
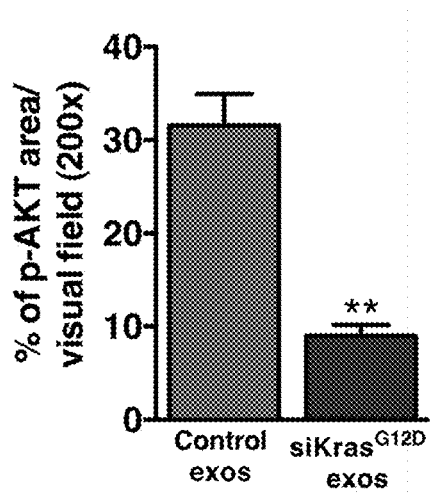

The anti-tumor properties of siRNA iExosomes (i.e., exosomes comprising a drug substance, such as an siRNA) treatment in nude mice with Panc-1 tumors warranted further evaluation in genetically engineered mouse model (GEMM) of PDAC. The rapidly progressing Ptf1acre/+; LSL-KRasG12D/+;Tgfbr2flox/flox mice (PKT mice (Özdemir et al., 2014)) were treated with siKras$^{G12D}$ exos. These mice spontaneously develop pancreas adenocarcinoma that reliably recapitulates the clinical and histopathology of human pancreas cancer (Özdemir et al., 2014). The model is fully penetrant and disease progression is highly comparable across mice (Özdemir et al., 2014). PKT mice develop pancreatic intraepithelial neoplasia (PaNIN) stage at around 28 days of age, develop invasive adenocarcinoma around 32 days and die at 45-55 days of age. Mice were injected i.p. every 48 hours with non-electroporated control exosomes or siKras$^{G12D}$ or shKras$^{G12D}$ exos starting at day 33 of age (mice with PDAC) (FIG. 3A). Focal accumulation of Alexa Fluor® 647 label from exos containing tagged siRNA was detected in pancreas tumors of mice upon sacrifice. siKras$^{G12D}$ or shKras$^{G12D}$ exos-treated mice showed a significant extension in life span, with a mean survival of 50 days for mice treated with shKras$^{G12D}$ exos and 60 days for mice treated with siKras$^{G12D}$ exos, when compared to control exos-treated mice, which showed a mean survival of 43 days (FIG. 3B). The increased survival was associated with a significant decrease in tumor burden in siKras$^{G12D}$ exos-treated mice compared to control exos-treated mice at both age-matched time points (FIG. 3C) and respective experimental endpoints (FIG. 7A). In addition to a significant survival advantage (FIG. 3B), histopathological features of tumors of siKras$^{G12D}$ exos-treated mice (age matched to control exos-treated mice at 44 days of age) revealed a relative increase in normal parenchymal and PaNIN stage lesions, contrasting with the near complete conversion of the pancreas to cancerous tissues with invasive features in control mice at 44 days of age (FIG. 3D). The pancreas of siKras$^{G12D}$ exos-treated mice at a median 60 days of age (experimental endpoint) still demonstrated improved histopathological features when compared to control mice (FIG. 7B). Experiments with GEMM were initially conducted using exosomes derived from BJ human fibroblasts. To address the potential impact of species differences in the efficacy of siRNA exos in GEMM, syngeneic fibroblasts were isolated from pancreas of PKT mice and siKras$^{G12D}$ exos were generated from these primary cell cultures. A similar improvement in survival, tumor burden, and histopathological features was noted when using mouse fibroblast-derived siRNA exos as when using BJ fibroblast-derived siRNA exos and when compared to mice treated with control exos (FIGS. 3E-F; FIG. 7C). siKras$^{G12D}$ exos treatment significantly reduced desmoplastic reaction associated with pancreas cancer progression in PKT mice (reduced extracellular matrix deposition associated with fibrosis in PKT tumors, increased cancer cell apoptosis assayed by TUNEL staining, reduced cancer cell proliferation (decreased Ki67 staining)), and reduced phospho-ERK and phospho-AKT staining in tumors (FIG. 3G, FIG. 7D).

Example 2—CD47 Prevents Uptake of Exosomes by Circulating Monocytes

Figure 8A:
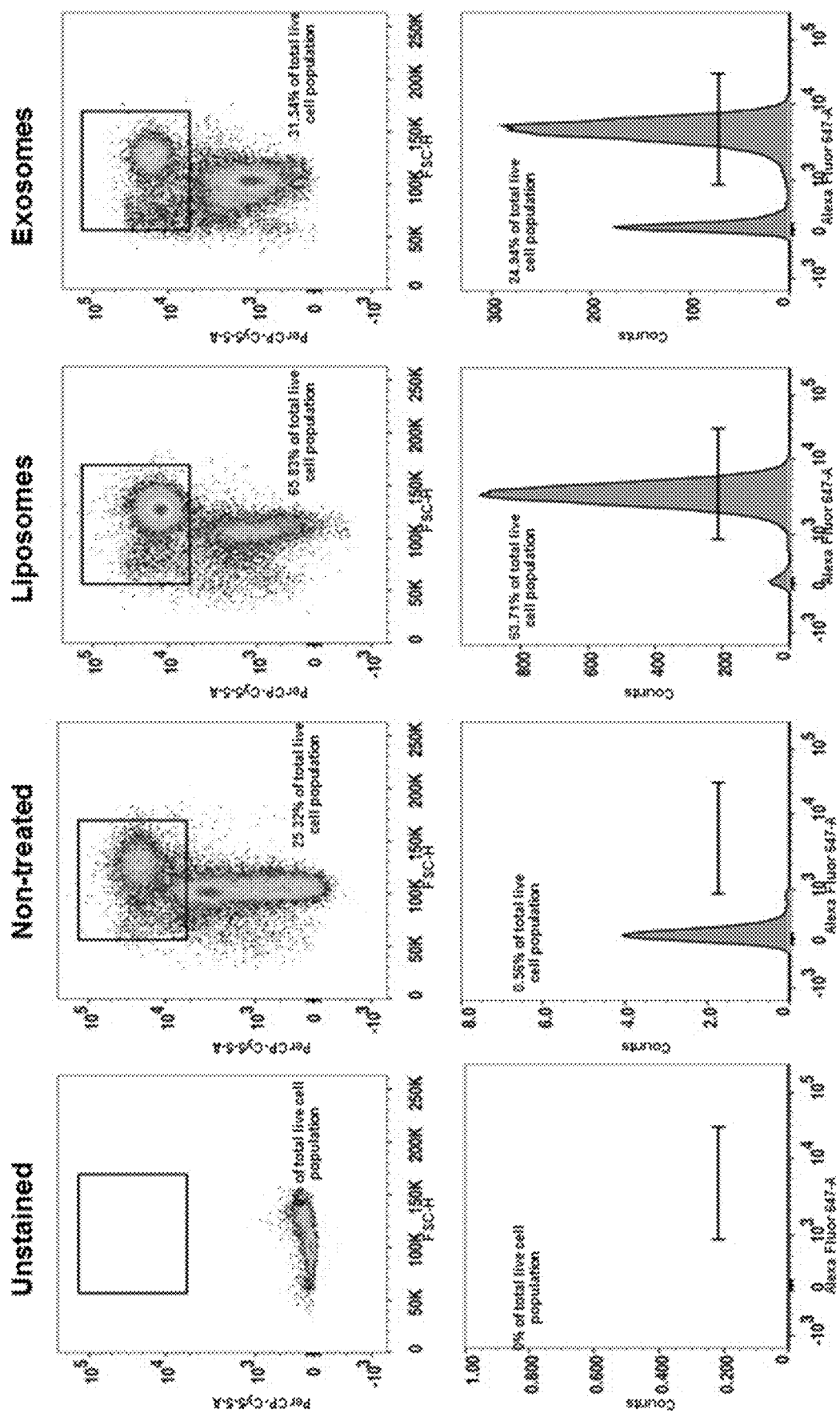
FIGS. 8A-B. Circulating monocytes engulf iLiposomes (i.e., liposomes comprising a drug substance, such as an inhibitory RNA) more efficiently than iExosomes (i.e., exosomes comprising a drug substance, such as an inhibitory RNA).
Figure 8B:
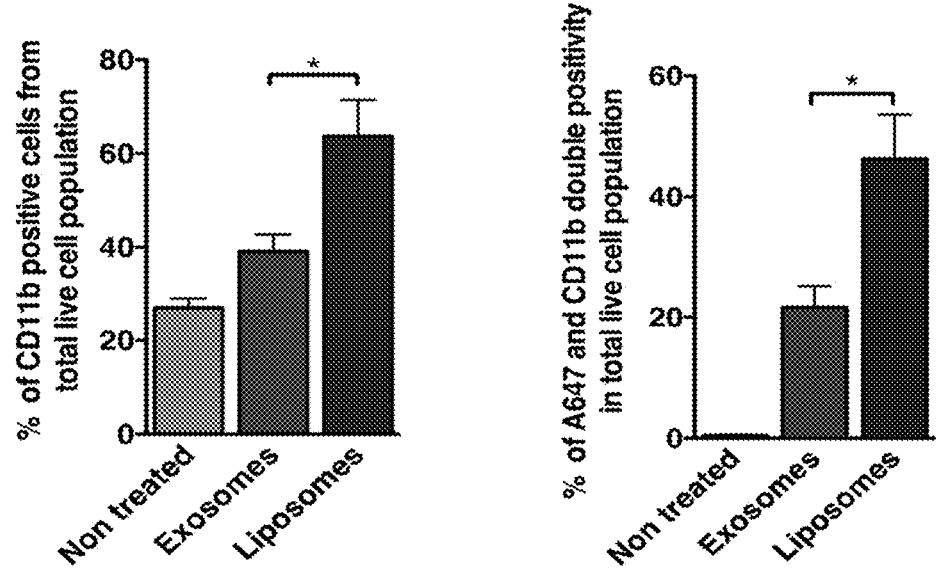
Figure 9A:
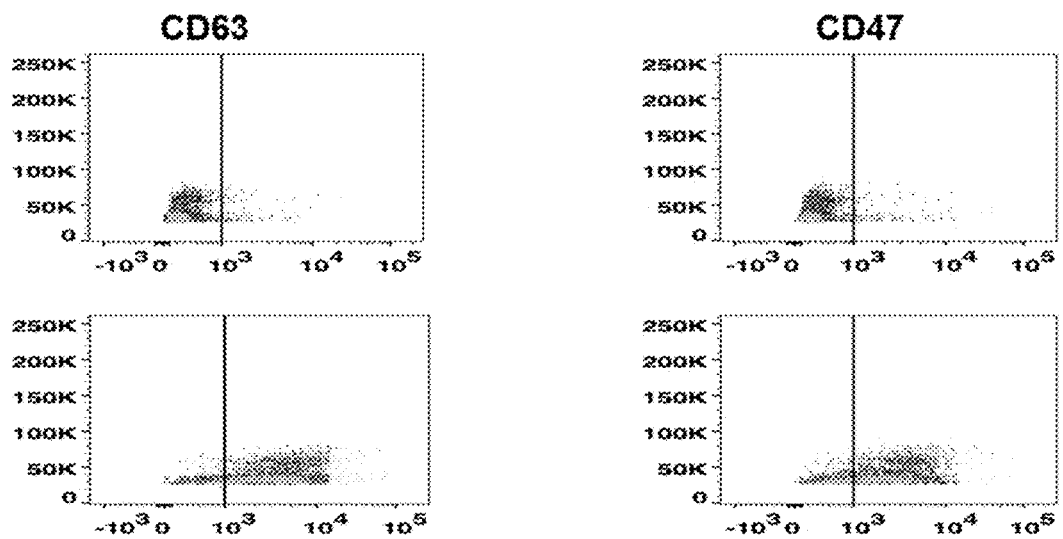
FIGS. 9A-C. CD47 is detected on exosomes but not exosomes.
Figure 9B:
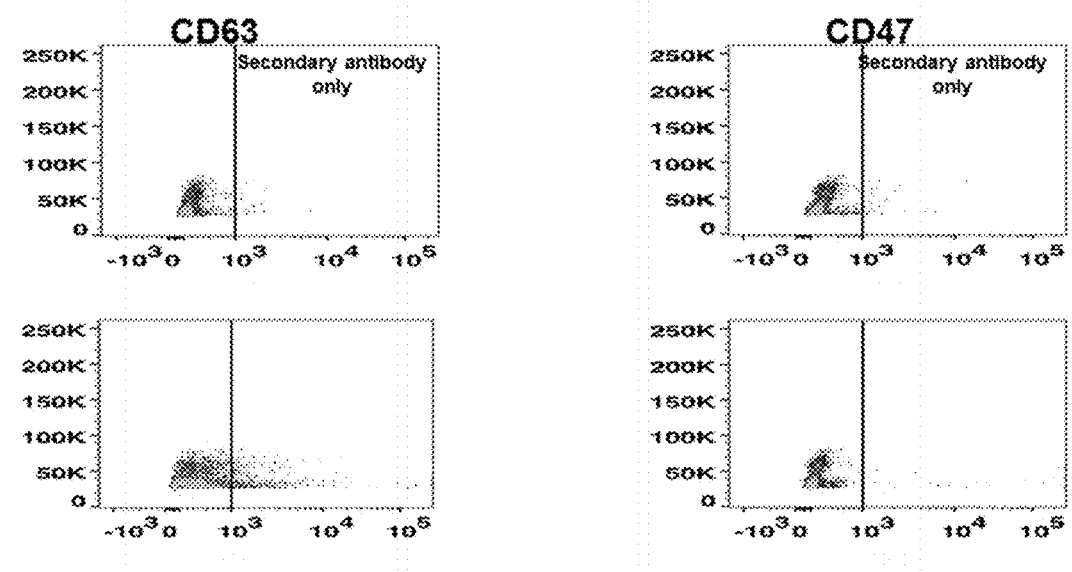
Figure 9C:
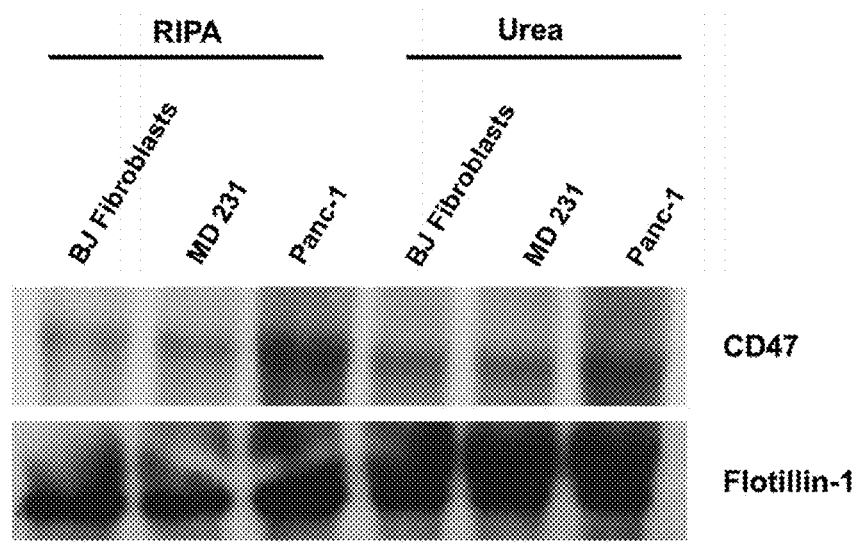
Figure 10:
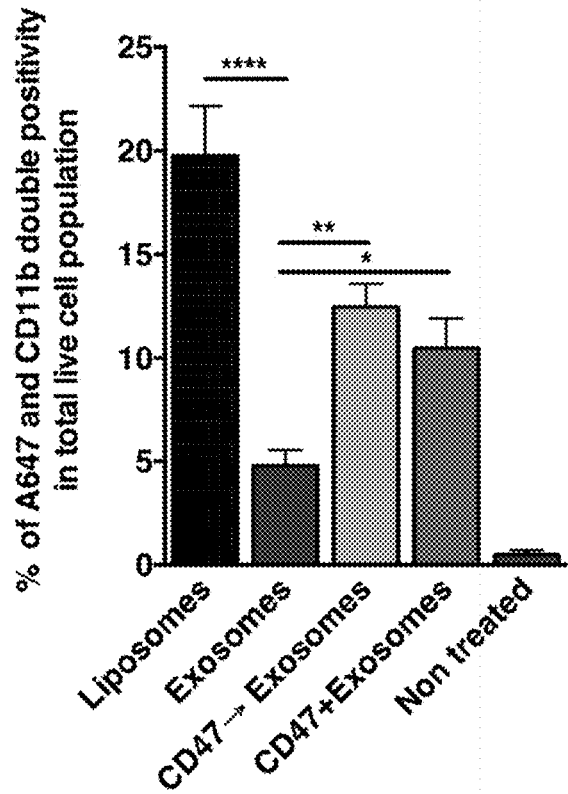
FIG. 10. Anti-CD47 antibody stimulates exosomes uptake by circulating monocytes in vivo. Exosomes were treated with an anti-CD47 antibody, which allowed for uptake of exosomes by circulating monocytes in vivo.

Circulating monocytes were found to engulf liposomes (100 nm; purchased from Encapsula Nanosciences) but not exosomes (FIGS. 8A-8B). Exosomes isolated from BJ fibroblasts were found to comprise CD47 on their surface (FIGS. 9A and 9C) while liposomes were determined to lack CD47 on their surface (FIG. 9B). Treatment of exosomes with an anti-CD47 antibody was found to stimulate the uptake of exosomes by circulating monocytes in vivo (FIG. 10).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945

Almoguera et al., Most human carcinomas of the exocrine pancreas contain mutant c-K-ras genes. *Cell*, 53:549-554, 1988.

Alvarez-Erviti et al., Delivery of siRNA to the mouse brain by systemic injection of targeted exosomes. *Nature Biotechnology*, 29:341-345, 2011.

Austin-Ward and Villaseca, Gene therapy and its applications. *Rev. Med. Chil.*, 126:838-845, 1998.

Baietti et al., Syndecan-syntenin-ALIX regulated the biogenesis of exosomes. *Nat. Cell Biol.*, 14:677-685, 2012.

Biankin et al., Pancreatic cancer genomes reveal aberrations in axon guidance pathway genes. *Nature*, 491:399-405, 2012.

Bukowski et al., Signal transduction abnormalities in T lymphocytes from patients with advanced renal carcinoma: clinical relevance and effects of cytokine therapy. *Clin. Cancer Res.*, 4:2337-2347, 1998.

Chang et al., Pancreatic cancer genomics. *Current Opinion in Genetics & Development*, 24:74-81, 2014.

Christodoulides et al., Immunization with recombinant class 1 outer-membrane protein from Neisseria meningitidis: influence of liposomes and adjuvants on antibody avidity, recognition of native protein and the induction of a bactericidal immune response against meningococci. *Microbiology*, 144:3027-3037, 1998.

Clayton et al., Antigen-presenting cell exosomes are protected from complement-mediated lysis by expression of CD55 and CD59. *European Journal of Immunology*, 33:522-531, 2003.

Collins et al., Oncogenic Kras is required for both the initiation and maintenance of pancreatic cancer in mice. *The Journal of Clinical Investigation*, 122:639-653, 2012a.

Collins et al., Metastatic pancreatic cancer is dependent on oncogenic Kras in mice. *PLoS One*, 7:e49707, 2012b.

Combes et al., A new flow cytometry method of platelet-derived microvesicle quantitation in plasma, *Thromb. Haemost.*, 77:220, 1997.

Cooper et al., Systemic exosomal siRNA delivery reduced alpha-synuclein aggregates in brains of transgenic mice. *Movement Disorders*, 29:1476-1485, 2014.

Davidson et al., Intralesional cytokine therapy in cancer: a pilot study of GM-CSF infusion in mesothelioma. *J. Immunother.*, 21:389-398, 1998.

Du et al., A systematic analysis of the silencing effects of an active siRNA at all single-nucleotide mismatched target sites. *Nucleic Acids Research*, 33:1671-1677, 2005.

El-Andaloussi et al., Extracellular vesicles: biology and emerging therapeutic opportunities. *Nature Reviews Drug Discovery*, 12:347-357, 2013.

El-Andaloussi et al., Exosome-mediated delivery of siRNA in vitro and in vivo. *Nature Protocols*, 7:2112-2126, 2012.

Eser et al., Oncogenic KRAS signalling in pancreatic cancer. *British Journal of Cancer*, 111:817-822, 2014.

Gomes-da-Silva et al., Lipid-based nanoparticles for siRNA delivery in cancer therapy: paradigms and challenges. *Accounts of Chemical Research*, 45:1163-1171, 2012.

Gysin et al., Therapeutic strategies for targeting ras proteins. *Genes & Cancer*, 2:359-372, 2011.

Hanibuchi et al., Therapeutic efficacy of mouse-human chimeric anti-ganglioside GM2 monoclonal antibody against multiple organ micrometastases of human lung cancer in NK cell-depleted SCID mice. *Int. J. Cancer*, 78:480-485, 1998.

Hellstrand et al., Histamine and cytokine therapy. *Acta Oncol.*, 37:347-353, 1998.

Hingorani et al., Trp53R172H and KrasG12D cooperate to promote chromosomal instability and widely metastatic pancreatic ductal adenocarcinoma in mice. *Cancer Cell*, 7:469-483, 2005.

Hollander, Immunotherapy for B-cell lymphoma: current status and prospective advances. *Front Immunol.*, 3:3, 2013.

Howlader et al., SEER Cancer Statistics Review, 1975-2011, National Cancer Institute. Bethesda, Md. On the World Wide Web at seercancergov/csr/1975_2011/, 2013.

Hruban et al., K-ras oncogene activation in adenocarcinoma of the human pancreas. A study of 82 carcinomas using a combination of mutant-enriched polymerase chain reaction analysis and allele-specific oligonucleotide hybridization. *The American Journal of Pathology*, 143:545-554, 1993.

Hui and Hashimoto, Pathways for Potentiation of Immunogenicity during Adjuvant-Assisted Immunizations with *Plasmodium falciparum* Major Merozoite Surface Protein 1. *Infec. Immun.*, 66:5329-5336, 1998.

Ji et al., Ras activity levels control the development of pancreatic diseases. *Gastroenterology*, 137:1072-1082, 82 el-6, 2009.

Johnsen et al., A comprehensive overview of exosomes as drug delivery vehicles—endogenous nanocarriers for targeted cancer therapy. *Biochimica et Biophysica Acta*, 1846:75-87, 2014.

Kahlert et al., Identification of Double Stranded Genomic DNA Spanning all Chromosomes with Mutated KRAS and p53 DNA in the Serum Exosomes of Patients with Pancreatic Cancer. The Journal of biological chemistry 2014.

Kowal et al., Biogenesis and secretion of exosomes. *Current Opinion in Cell Biology*, 29:116-125, 2014.

Luga et al., Exosomes mediate stromal mobilization of autocrine Wnt-PCP signaling in breast cancer cell migration. *Cell*, 151:1542-1556, 2012.

Ma et al., Structural basis for overhang-specific small interfering RNA recognition by the PAZ domain. *Nature*, 429:318-322, 2004.

Marcus and Leonard, FedExosomes: Engineering Therapeutic Biological Nanoparticles that Truly Deliver. *Pharmaceuticals* (Basel), 6:659-680, 2013.

Melo et al., Glypican-1 identifies cancer exosomes and detects early pancreatic cancer. *Nature*, 523:177-182, 2015.

Ozdemir et al., Depletion of carcinoma-associated fibroblasts and fibrosis induces immunosuppression and accelerates pancreas cancer with reduced survival. *Cancer Cell*, 25:719-734, 2014.

Pecot et al., Therapeutic Silencing of KRAS using Systemically Delivered siRNAs. *Molecular Cancer Therapeutics*, 13:2876-2885, 2014.

Peinado et al., Melanoma exosomes educate bone marrow progenitor cells toward a pro-metastatic phenotype through MET. *Nature Medicine,* 18:883-891, 2012.

Poliseno et al., A coding-independent function of gene and pseudogene mRNAs regulates tumour biology. *Nature,* 465:1033-1038, 2010.

Qin et al., Interferon-beta gene therapy inhibits tumor formation and causes regression of established tumors in immune-deficient mice. *Proc. Natl. Acad. Sci. U.S.A.,* 95:14411-14416, 1998.

Rachagani et al., Activated KrasG12D is associated with invasion and metastasis of pancreatic cancer cells through inhibition of E-cadherin. *Br. J. Cancer,* 104:1038-1048, 2011.

Rejiba et al., K-ras oncogene silencing strategy reduces tumor growth and enhances gemcitabine chemotherapy efficacy for pancreatic cancer treatment. *Cancer Science,* 98:1128-1136, 2007.

Siegel et al., Cancer statistics, 2014. *CA: A cancer journal for clinicians,* 64:9-29, 2014.

Simoes et al., Cationic liposomes for gene delivery. *Expert Opinion on Drug Delivery,* 2:237-254, 2005.

Smakman et al., Dual effect of Kras(D12) knockdown on tumorigenesis: increased immune-mediated tumor clearance and abrogation of tumor malignancy. *Oncogene,* 24:8338-8342, 2005.

Sun et al., Characterization of the mutations of the K-ras, p53, p16, and SMAD4 genes in 15 human pancreatic cancer cell lines. *Oncology Reports,* 8:89-92, 2001.

Thery et al., Exosomes: composition, biogenesis and function. *Nature Reviews Immunology,* 2:569-579, 2002.

Valadi et al., Exosome-mediated transfer of mRNAs and microRNAs is a novel mechanism of genetic exchange between cells. *Nature Cell Biology,* 9:654-659, 2007.

van den Boom et al., Exosomes as nucleic acid nanocarriers. *Advanced Drug Delivery Reviews,* 65:331-335, 2013.

van der Meel et al., Extracellular vesicles as drug delivery systems: Lessons from the liposome field. *Journal of Controlled Release,* 195:72-85, 2014.

Wahlgren et al., Plasma exosomes can deliver exogenous short interfering RNA to monocytes and lymphocytes. *Nucleic Acids Research,* 40:e130, 2012.

Xue et al., Small RNA combination therapy for lung cancer. *Proceedings of the National Academy of Sciences USA,* 111:E3553-3561, 2014.

Ying et al., Oncogenic Kras maintains pancreatic tumors through regulation of anabolic glucose metabolism. *Cell,* 149:656-670, 2012.

Yuan et al., Development of siRNA payloads to target KRAS-mutant cancer. *Cancer Discovery,* 4:1182-1197, 2014.

Zorde Khvalevsky et al., Mutant KRAS is a druggable target for pancreatic cancer. *Proceedings of the National Academy of Sciences USA,* 110:20723-20728, 2013.

What is claimed is:

1. A pharmaceutical composition comprising an exosome and an excipient, wherein the exosome comprises an inhibitory RNA selected from the group consisting of a siRNA, shRNA, miRNA, and pre-miRNA, wherein the exo some is isolated from a normal skin fibroblast cell that overexpresses CD47, and wherein the exosome comprises CD47 on its surface.

2. The composition of claim 1, wherein the composition is formulated for parenteral administration.

3. The composition of claim 2, wherein the composition is formulated for intravenous, intramuscular, sub-cutaneous, or intraperitoneal injection.

4. The composition of claim 2, further comprising an antimicrobial agent.

5. The composition of claim 4, wherein the antimicrobial agent is selected from the group consisting of benzalkonium chloride, benzethonium chloride, benzyl alcohol, bronopol, centrimide, cetylpyridinium chloride, chlorhexidine, chlorobutanol, chlorocresol, chloroxylenol, cresol, ethyl alcohol, glycerin, exetidine, imidurea, phenol, phenoxyethanol, phenylethl alcohol, phenlymercuric nitrate, propylene glycol, and thimerosal.

6. The composition of claim 1, wherein the inhibitory RNA is an siRNA.

7. The composition of claim 6, wherein the siRNA is about 19 to about 25 nucleotides in length.

8. The composition of claim 6, wherein the siRNA comprises a modified backbone.

9. The composition of claim 8, wherein the siRNA comprises a phosphorothioate backbone or a phosphorodithioate backbone.

10. The composition of claim 6, wherein the siRNA comprises one or more of a modification selected from the group consisting of a 2'-O-methyl ribonucleotide, a 2'-deoxy-2'-fluoro ribonucleotide, a "universal base" nucleotide, a 5-C-methyl nucleotide, a phosphorothioate internucleotide linkage, and an inverted deoxyabasic residue incorporation.

* * * * *